(12) United States Patent
Kusters et al.

(10) Patent No.: US 11,890,399 B2
(45) Date of Patent: Feb. 6, 2024

(54) CENTRIFUGAL SEPARATION AND COLLECTION OF RED BLOOD CELLS, PLASMA, OR BOTH RED BLOOD CELLS AND PLASMA

(71) Applicant: Fenwal, Inc., Lake Zurich, IL (US)

(72) Inventors: Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 270 days.

(21) Appl. No.: 16/878,653

(22) Filed: May 20, 2020

(65) Prior Publication Data

US 2020/0368412 A1 Nov. 26, 2020

Related U.S. Application Data

(60) Provisional application No. 62/851,725, filed on May 23, 2019.

(51) Int. Cl.
*A61M 1/02* (2006.01)
*A61M 1/36* (2006.01)
(Continued)

(52) U.S. Cl.
CPC .......... *A61M 1/029* (2013.01); *A61M 1/3693* (2013.01); *A61M 1/3696* (2014.02);
(Continued)

(58) Field of Classification Search
CPC .. A61M 1/029; A61M 1/3693; A61M 1/3696; A61M 1/265; A61M 1/38;
(Continued)

(56) References Cited

U.S. PATENT DOCUMENTS 3,655,123 A * 4/1972 Judson .................. B04B 5/0442
604/6.11
4,680,025 A * 7/1987 Kruger ................ A61M 1/3693
604/6.02
(Continued)

FOREIGN PATENT DOCUMENTS

EP 1946784 B1 10/2012
WO WO2012/091720 A1 7/2012
(Continued)

OTHER PUBLICATIONS

Extended European Search Report, dated Oct. 21, 2020, for application No. EP20175596.4-1115.

*Primary Examiner* — Liam Royce
(74) *Attorney, Agent, or Firm* — Cook Alex Ltd.

(57) ABSTRACT

Systems and methods are provided for separating blood into two or more components for collection of red blood cells, plasma, or both red blood cells and plasma. A blood separation system includes a blood separation device and a fluid flow circuit configured to be mounted to the blood separation device. The blood separation device includes a centrifugal separator and a spinning membrane separator drive unit, with the blood being separated into its constituents by the centrifugal separator. Separated plasma may be collected following separation by the centrifugal separator or may first be conveyed from the centrifugal separator into the spinning membrane separator drive unit to separate cellular blood components from the plasma prior to collection of the filtered plasma. The cellular blood components filtered from the plasma may be retained in the circuit as a waste product or may be flushed out of the circuit to a recipient.

20 Claims, 53 Drawing Sheets

(51) Int. Cl.
  *B04B 5/04* (2006.01)
  *B04B 11/02* (2006.01)
  *B04B 13/00* (2006.01)
  *A61M 1/26* (2006.01)
  *A61M 1/38* (2006.01)

(52) U.S. Cl.
  CPC .... *A61M 1/36224* (2022.05); *A61M 1/36225* (2022.05); *A61M 1/362227* (2022.05); *A61M 1/362261* (2022.05); *A61M 1/362265* (2022.05); *B04B 5/0442* (2013.01); *A61M 1/265* (2014.02); *A61M 1/38* (2013.01); *A61M 2205/50* (2013.01); *A61M 2205/7545* (2013.01); *B04B 11/02* (2013.01); *B04B 2013/006* (2013.01)

(58) Field of Classification Search
  CPC ...... A61M 2205/50; A61M 2205/7545; B04B 5/0442; B04B 11/02; B04B 2013/006
  See application file for complete search history.

(56) References Cited

U.S. PATENT DOCUMENTS

| | | | |
|---|---|---|---|
| 4,776,964 A * | 10/1988 | Schoendorfer | A61M 1/3696 210/651 |
| 5,194,145 A | 3/1993 | Schoendorfer | |
| 5,632,893 A | 5/1997 | Brown et al. | |
| 5,868,696 A | 2/1999 | Giesler et al. | |
| 6,419,822 B2 | 7/2002 | Muller et al. | |
| 6,471,855 B1 | 10/2002 | Odak et al. | |
| 6,579,219 B2 | 6/2003 | Dolecek et al. | |
| 6,582,386 B2 | 6/2003 | Min et al. | |
| 6,629,919 B2 | 10/2003 | Egozy et al. | |
| 6,706,008 B2 | 3/2004 | Vishnoi et al. | |
| 6,770,883 B2 | 8/2004 | McNeal et al. | |
| 6,808,503 B2 | 10/2004 | Farrell et al. | |
| 6,866,826 B2 | 3/2005 | Moore et al. | |
| 6,884,228 B2 | 4/2005 | Brown et al. | |
| 7,049,622 B1 | 5/2006 | Weiss | |
| 7,081,082 B2 | 7/2006 | Scholz et al. | |
| 7,150,834 B2 | 12/2006 | Mueth et al. | |
| 7,186,230 B2 | 3/2007 | Briggs et al. | |
| 7,186,231 B2 | 3/2007 | Takagi et al. | |
| 7,211,037 B2 | 5/2007 | Briggs et al. | |
| 7,294,513 B2 | 11/2007 | Wyatt | |
| 7,347,948 B2 | 3/2008 | Dolecek et al. | |
| 7,354,515 B2 | 4/2008 | Coull et al. | |
| 7,381,291 B2 | 6/2008 | Tobe et al. | |
| 7,422,693 B2 | 9/2008 | Carter et al. | |
| 7,485,084 B2 | 2/2009 | Borgstrom et al. | |
| 7,563,376 B2 | 7/2009 | Oishi | |
| 7,648,639 B2 | 1/2010 | Holmes et al. | |
| 7,806,845 B2 | 10/2010 | Arm et al. | |
| 7,906,771 B2 | 3/2011 | Carter et al. | |
| 7,951,059 B2 | 5/2011 | Sweat | |
| 8,057,377 B2 | 11/2011 | Holmes et al. | |
| 8,075,468 B2 | 12/2011 | Min et al. | |
| 8,163,276 B2 | 4/2012 | Hedrick et al. | |
| 8,287,742 B2 | 10/2012 | Holmes | |
| 8,317,672 B2 | 11/2012 | Nash et al. | |
| 8,337,379 B2 | 12/2012 | Kolenbrander et al. | |
| 8,535,210 B2 | 9/2013 | Kolenbrander et al. | |
| 8,556,793 B2 | 10/2013 | Foley et al. | |
| 8,758,211 B2 | 6/2014 | Nash et al. | |
| 8,974,362 B2 | 3/2015 | Nash et al. | |
| 9,011,687 B2 | 4/2015 | Swift et al. | |
| 9,156,039 B2 | 10/2015 | Holmes et al. | |
| 9,302,042 B2 | 4/2016 | Pages | |
| 9,302,276 B2 | 4/2016 | Pesetsky et al. | |
| 9,370,615 B2 | 6/2016 | Ragusa et al. | |
| 9,399,182 B2 | 7/2016 | Pesetsky et al. | |
| 9,550,016 B2 | 1/2017 | Gifford | |
| 9,610,590 B2 | 4/2017 | Hamandi | |
| 9,789,235 B2 | 10/2017 | Gifford et al. | |
| 10,086,128 B2 | 10/2018 | Kyle et al. | |
| 10,166,322 B2 | 1/2019 | Sweat et al. | |
| 10,238,787 B2 | 3/2019 | Takuwa | |
| 10,293,097 B2 | 5/2019 | Murphy et al. | |
| 10,399,881 B2 | 9/2019 | Donais et al. | |
| 10,493,467 B2 | 12/2019 | Lundquist et al. | |
| 10,518,007 B2 | 12/2019 | Kimura | |
| 10,561,783 B2 | 2/2020 | Hamandi et al. | |
| 2002/0128583 A1 | 9/2002 | Min et al. | |
| 2004/0195190 A1 | 10/2004 | Min et al. | |
| 2009/0215602 A1 | 8/2009 | Min et al. | |
| 2011/0003675 A1 | 1/2011 | Dolecek | |
| 2011/0294641 A1 | 12/2011 | Dolecek et al. | |
| 2014/0378292 A1 | 12/2014 | Igarashi | |
| 2015/0068959 A1 | 3/2015 | Zheng | |
| 2015/0104824 A1 | 4/2015 | Walker et al. | |
| 2015/0218517 A1 | 8/2015 | Kusters et al. | |
| 2015/0367063 A1 | 12/2015 | Kimura | |
| 2017/0153431 A1 | 6/2017 | Nguyen et al. | |
| 2018/0043374 A1 | 2/2018 | Meinig et al. | |
| 2018/0164141 A1 | 6/2018 | Bordignon et al. | |
| 2018/0185772 A1 | 7/2018 | Karhiniemi et al. | |
| 2019/0003873 A1 | 1/2019 | Araujo et al. | |
| 2019/0030545 A1 | 1/2019 | Hamada et al. | |
| 2019/0083696 A1 | 3/2019 | Igarashi | |

FOREIGN PATENT DOCUMENTS

| | | |
|---|---|---|
| WO | WO2013/043433 A2 | 3/2013 |
| WO | WO2014/039091 A1 | 3/2014 |
| WO | WO2018/053217 A1 | 3/2018 |
| WO | WO2018/154115 A2 | 8/2018 |
| WO | WO2019/047498 A1 | 3/2019 |
| WO | WO2019/165478 A1 | 8/2019 |
| WO | WO2020/002059 A1 | 1/2020 |
| WO | WO2020/055958 A1 | 3/2020 |

* cited by examiner

CENTRIFUGAL SEPARATION AND COLLECTION OF RED BLOOD CELLS, PLASMA, OR BOTH RED BLOOD CELLS AND PLASMA

CROSS-REFERENCE TO RELATED APPLICATIONS

This application claims the benefit of and priority of U.S. Provisional Patent Application Ser. No. 62/851,725, filed May 23, 2019, the contents of which are incorporated by reference herein.

BACKGROUND

Field of the Disclosure

The present disclosure relates to separation and collection of red blood cells, plasma, or both red blood cells and plasma. More particularly, the present disclosure relates to centrifugal separation and collection of red blood cells, plasma, or both red blood cells and plasma.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber.

While many blood separation systems and procedures have employed centrifugal separation principles, there is another class of devices, based on the use of a membrane, that has been used for plasmapheresis (i.e., separating plasma from whole blood). More specifically, this type of device employs relatively rotating surfaces, at least one or which carries a porous membrane. Typically, the device employs an outer stationary housing and an internal spinning rotor covered by a porous membrane.

Well-known plasmapheresis devices include the Autopheresis-C® and Aurora separators sold by Fenwal, Inc. of Lake Zurich, Illinois, which is an affiliate of Fresenius Kabi AG of Bad Homburg, Germany. A detailed description of an exemplary spinning membrane separator may be found in U.S. Pat. No. 5,194,145, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets, and white blood cells, move to the exit region between the spinner and the shell and then may be collected, returned to a blood source, or discarded.

Spinning membrane separators have been found to provide excellent plasma filtration rates, due primarily to the unique flow patterns ("Taylor vortices") induced in the gap between the spinning membrane and the shell. The Taylor vortices help to keep the blood cells from depositing on and fouling or clogging the membrane.

Both types of separators have their advantages, so it would be advantageous to provide an integrated system capable of harnessing the benefits of both centrifugal separation and spinning membrane separation. Such an integrated system is described in PCT Patent Application Publication No. WO 2018/053217 A1, which is hereby incorporated herein by reference. Such a system is very versatile, allowing for any of a number of blood separation procedures to be carried out using one or both of centrifugal and spinning membrane separation techniques. For example, PCT Patent Application Publication No. WO 2018/053217 A1 described procedures for separating blood and collecting red blood cells, plasma, and both red blood cells and plasma using only spinning membrane separation techniques. While spinning membrane separation techniques have been found to be satisfactory for such procedures, it would be advantageous to provide a user with the option of using the same system to separate blood and collect red blood cells, plasma, and both red blood cells and plasma using centrifugal separation techniques instead.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood separation device includes a centrifugal separator, a spinning membrane separator drive unit, a pump system, and a controller. The controller is configured to control the pump system to convey blood into the centrifugal separator, control the centrifugal separator to separate red blood cells from the blood, and control the pump system to collect at least a portion of the separated red blood cells.

In another aspect, a blood separation method includes mounting a fluid flow circuit to a blood separation device including a centrifugal separator and a spinning membrane separator drive unit. Blood is conveyed through the fluid flow circuit, with red blood cells being separated from at least a portion of the blood in the fluid flow circuit using the centrifugal separator. At least a portion of the separated red blood cells is collected.

In yet another aspect, a blood separation device includes a centrifugal separator, a spinning membrane separator drive unit, a pump system, and a controller. The controller is configured to control the pump system to convey blood into the centrifugal separator, control the centrifugal separator to separate red blood cells and plasma from the blood; and control the pump system to collect at least a portion of the separated red blood cells and at least a portion of the separated plasma.

In a further aspect, a blood separation method includes mounting a fluid flow circuit to a blood separation device including a centrifugal separator and a spinning membrane separator drive unit. Blood is conveyed through the fluid flow circuit, with red blood cells and plasma being separated from at least a portion of the blood in the fluid flow circuit using the centrifugal separator. At least a portion of the separated red blood cells is collected, and at least a portion of the separated plasma is also collected.

In another aspect, a blood separation device includes a centrifugal separator, a spinning membrane separator drive unit, a pump system, and a controller. The controller is configured to control the pump system to convey blood into the centrifugal separator, control the centrifugal separator to separate plasma from the blood, and control the pump system to collect at least a portion of the plasma.

In yet another aspect, a blood separation method includes mounting a fluid flow circuit to a blood separation device including a centrifugal separator and a spinning membrane separator drive unit. Blood is conveyed through the fluid flow circuit, with plasma being separated from at least a portion of the blood in the fluid flow circuit using the centrifugal separator. At least a portion of the separated plasma is collected.

Figure 1:
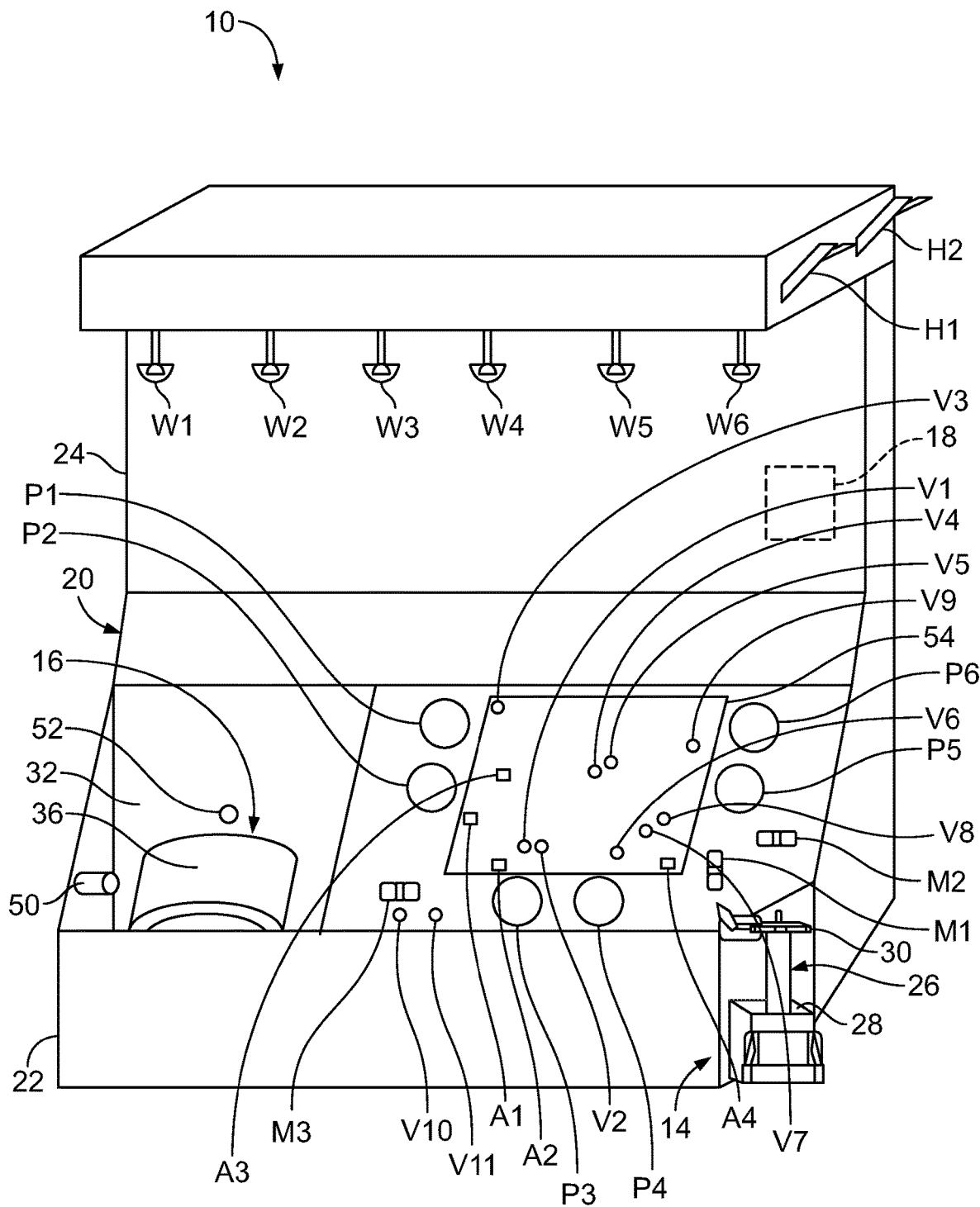
FIG. 1 is a perspective view of an exemplary blood separation device that comprises a component of a blood separation system according to an aspect of the present disclosure.
Figure 2A:
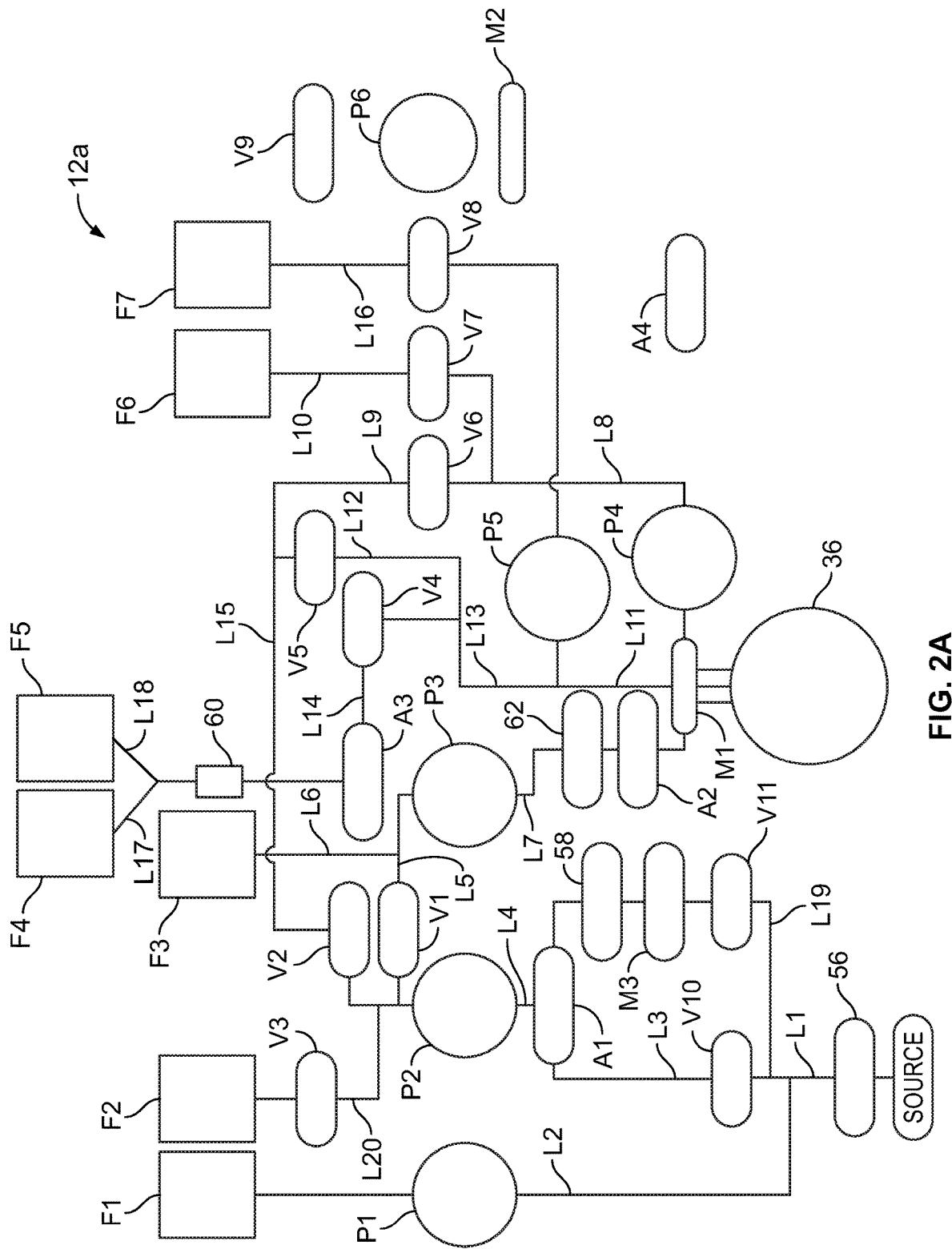
FIGS. 2A-2J are schematic views of different disposable fluid flow circuits that may be mounted to the blood separation device of FIG. 1 to complete a blood separation system according to an aspect of the present disclosure.
Figure 2B:
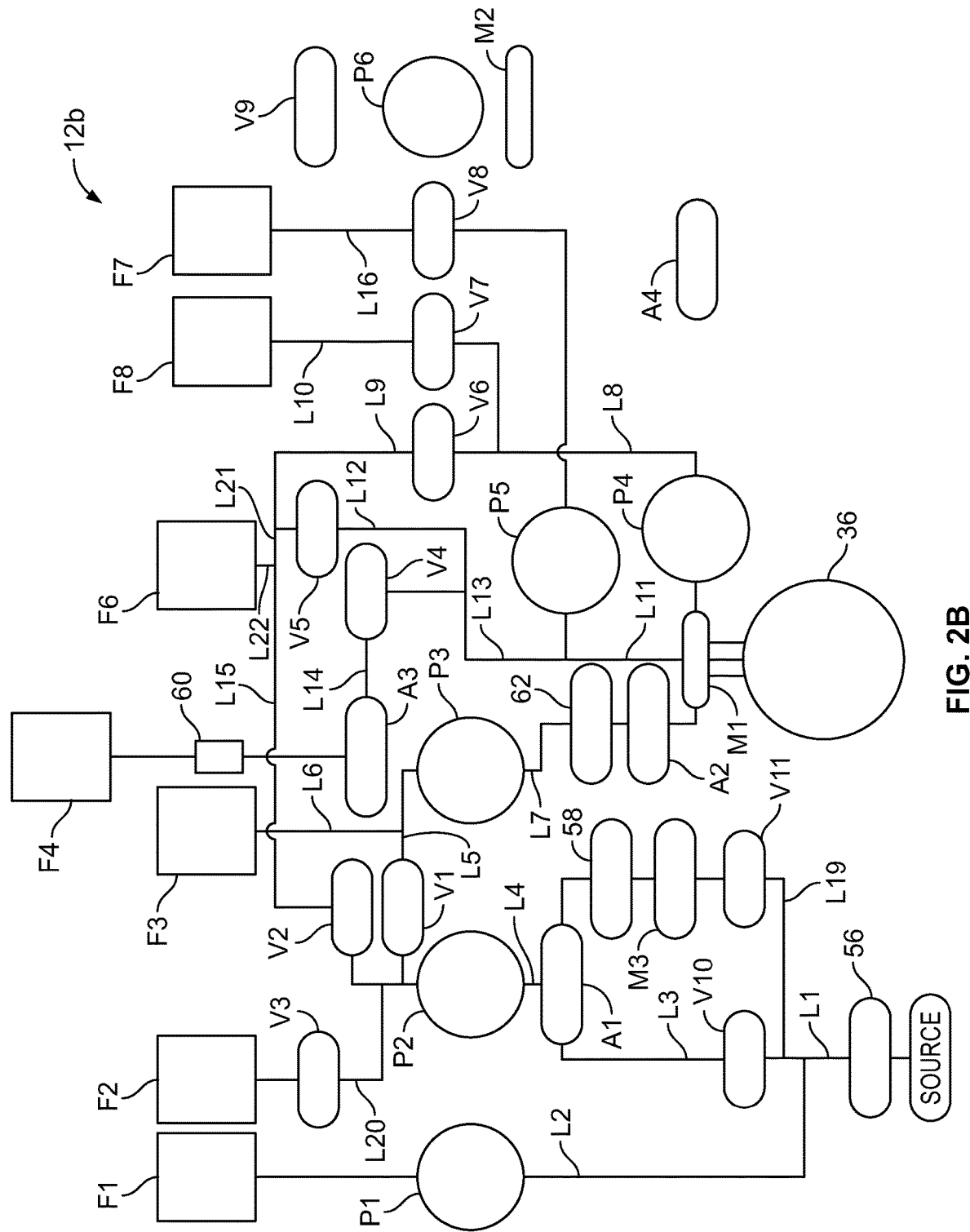
Figure 2C:
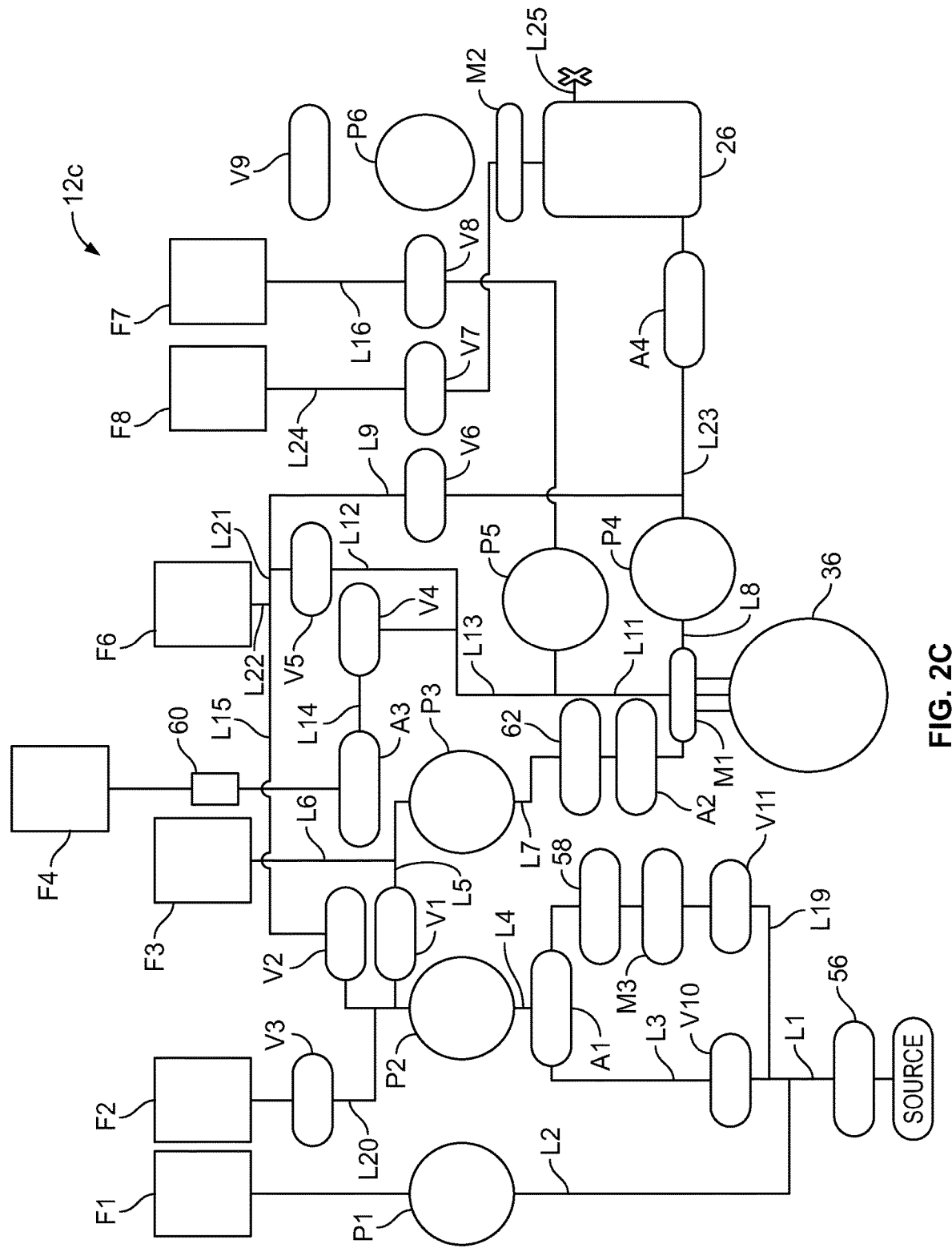
Figure 2D:
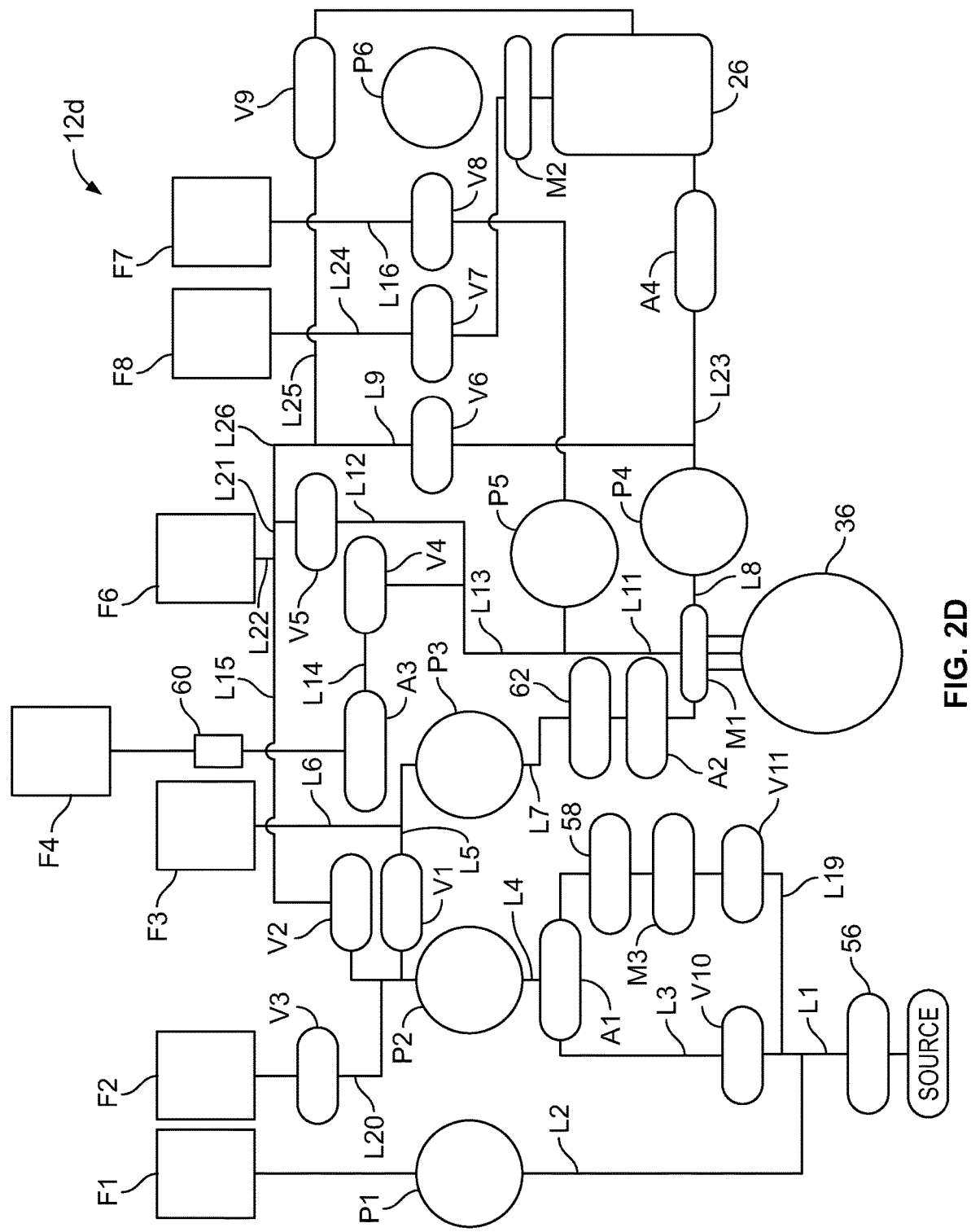
Figure 2E:
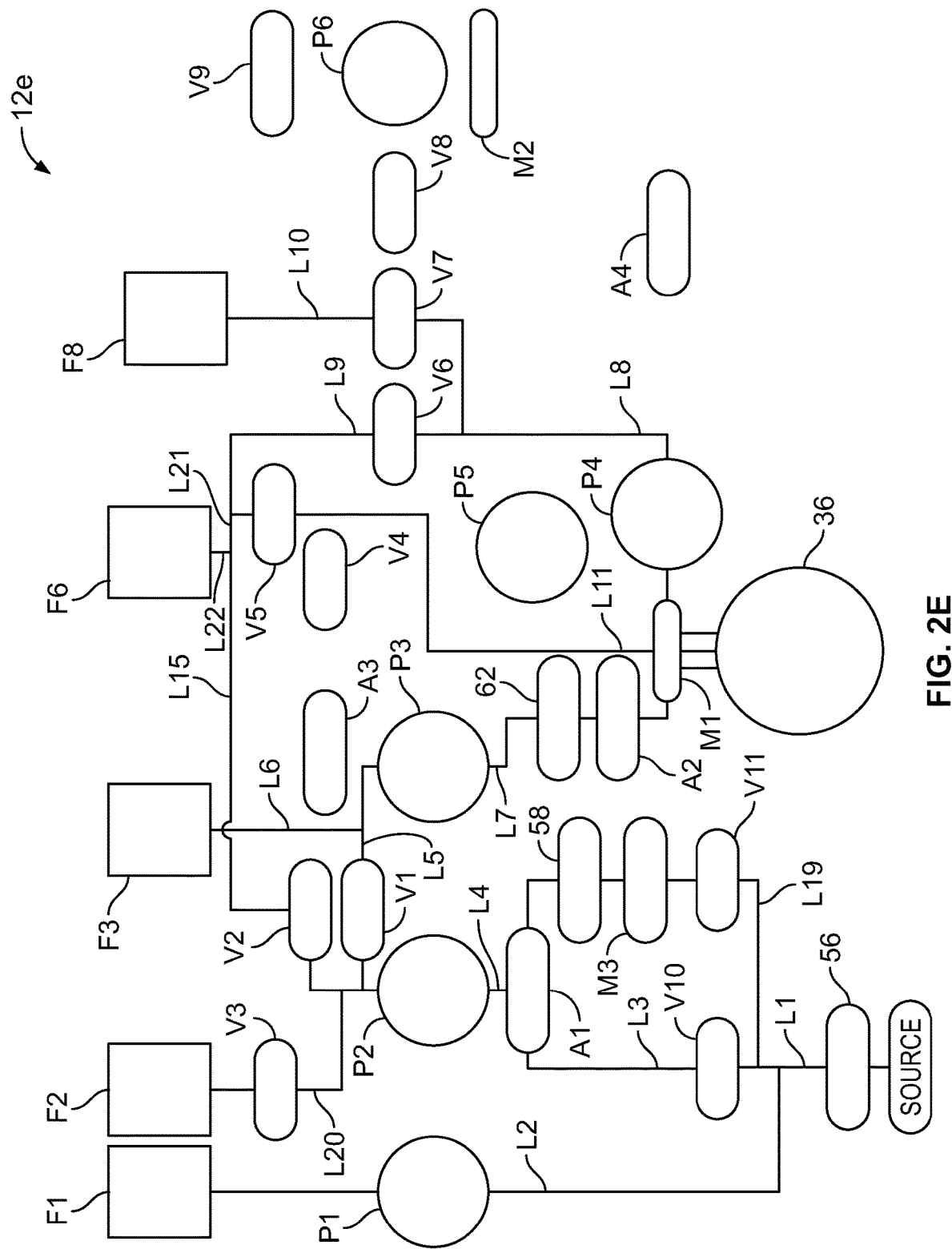
Figure 2F:
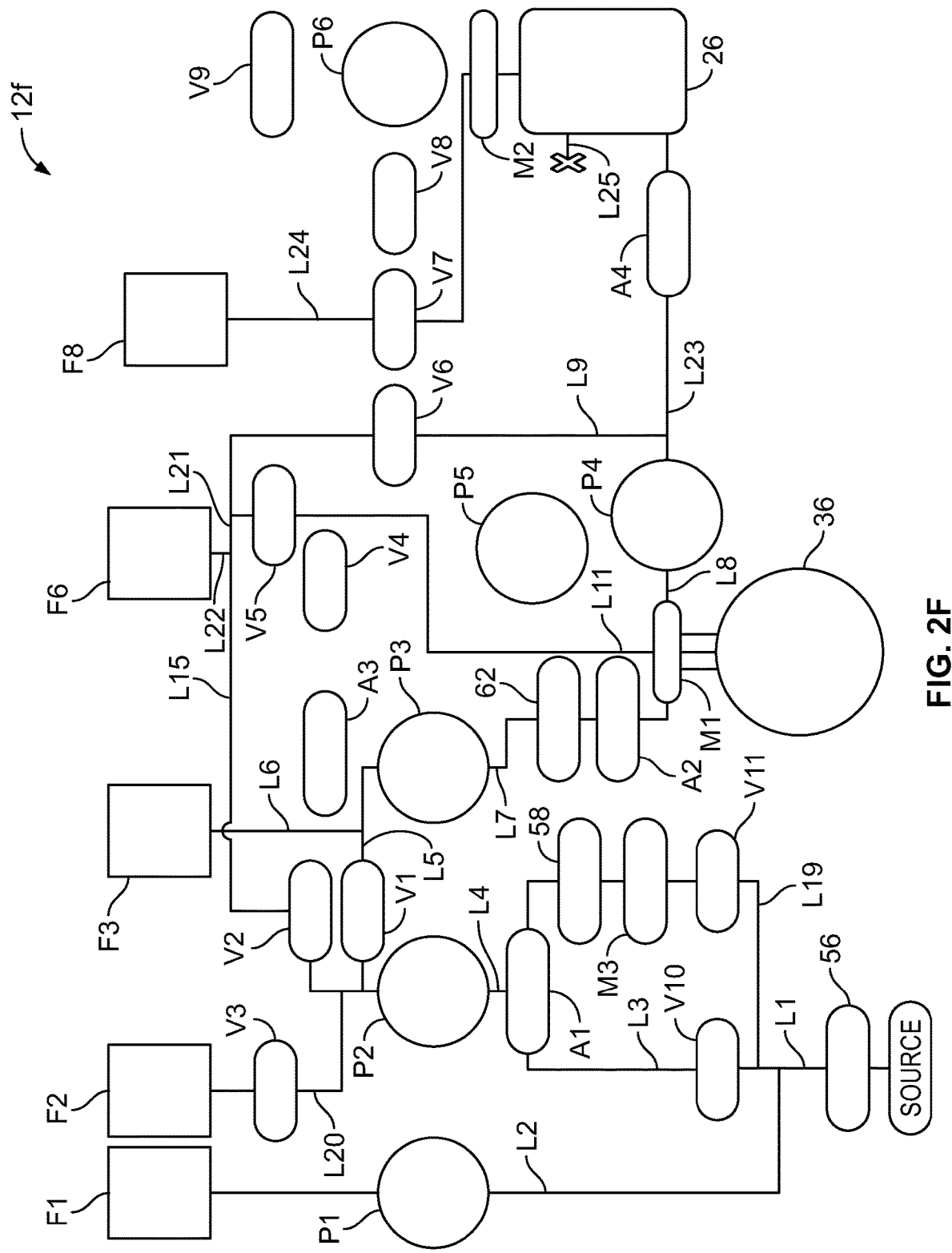
Figure 2G:
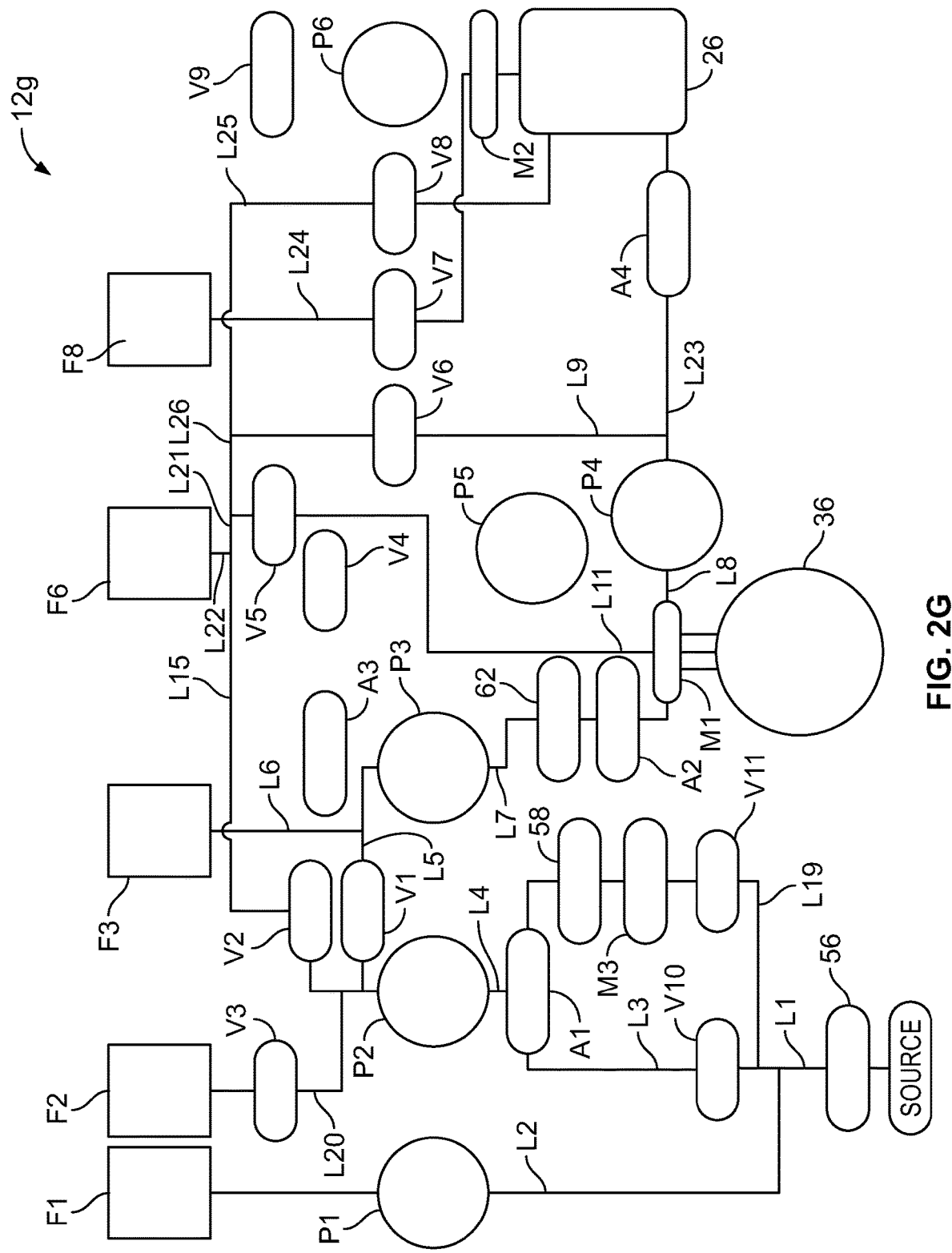
Figure 2H:
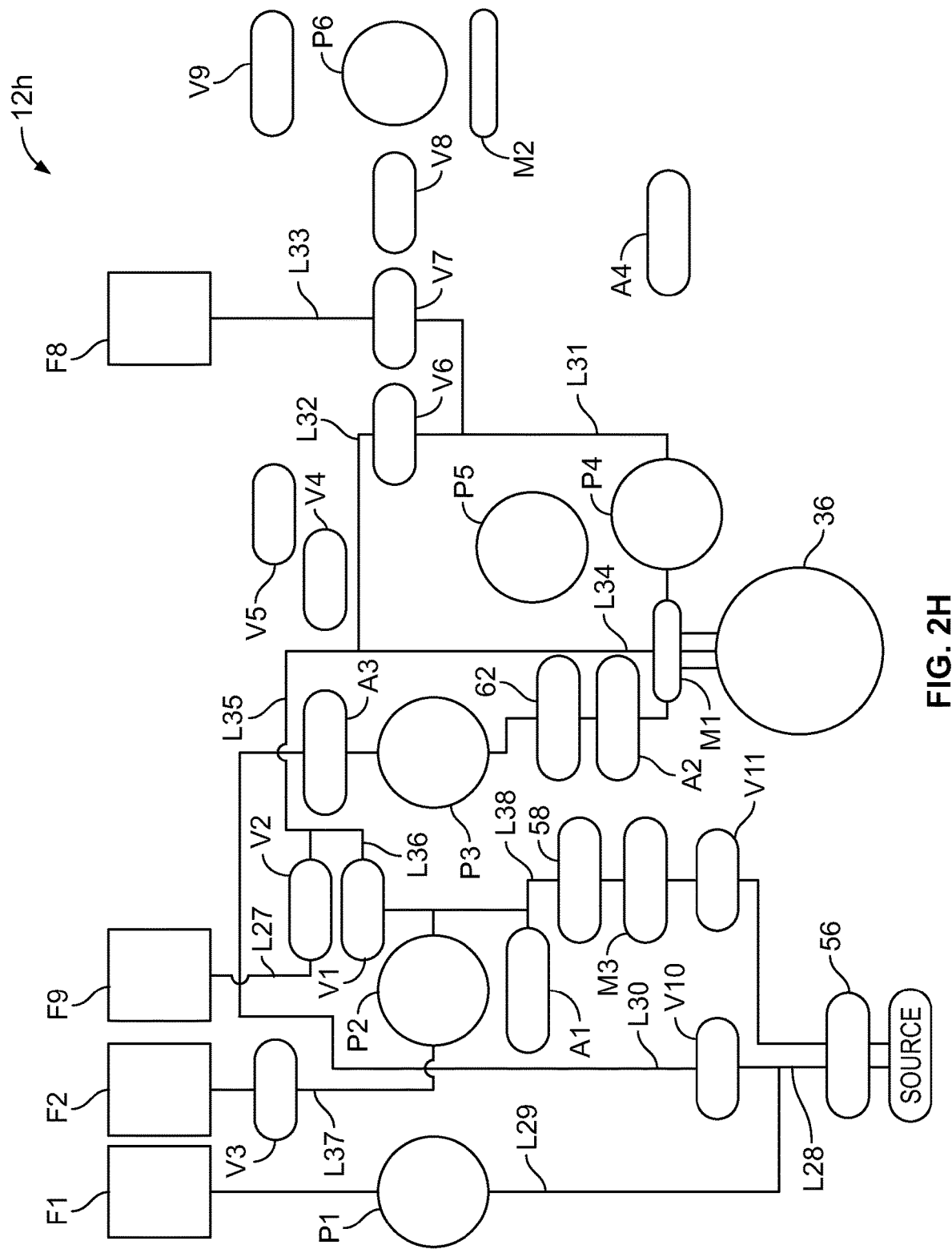
Figure 2I:
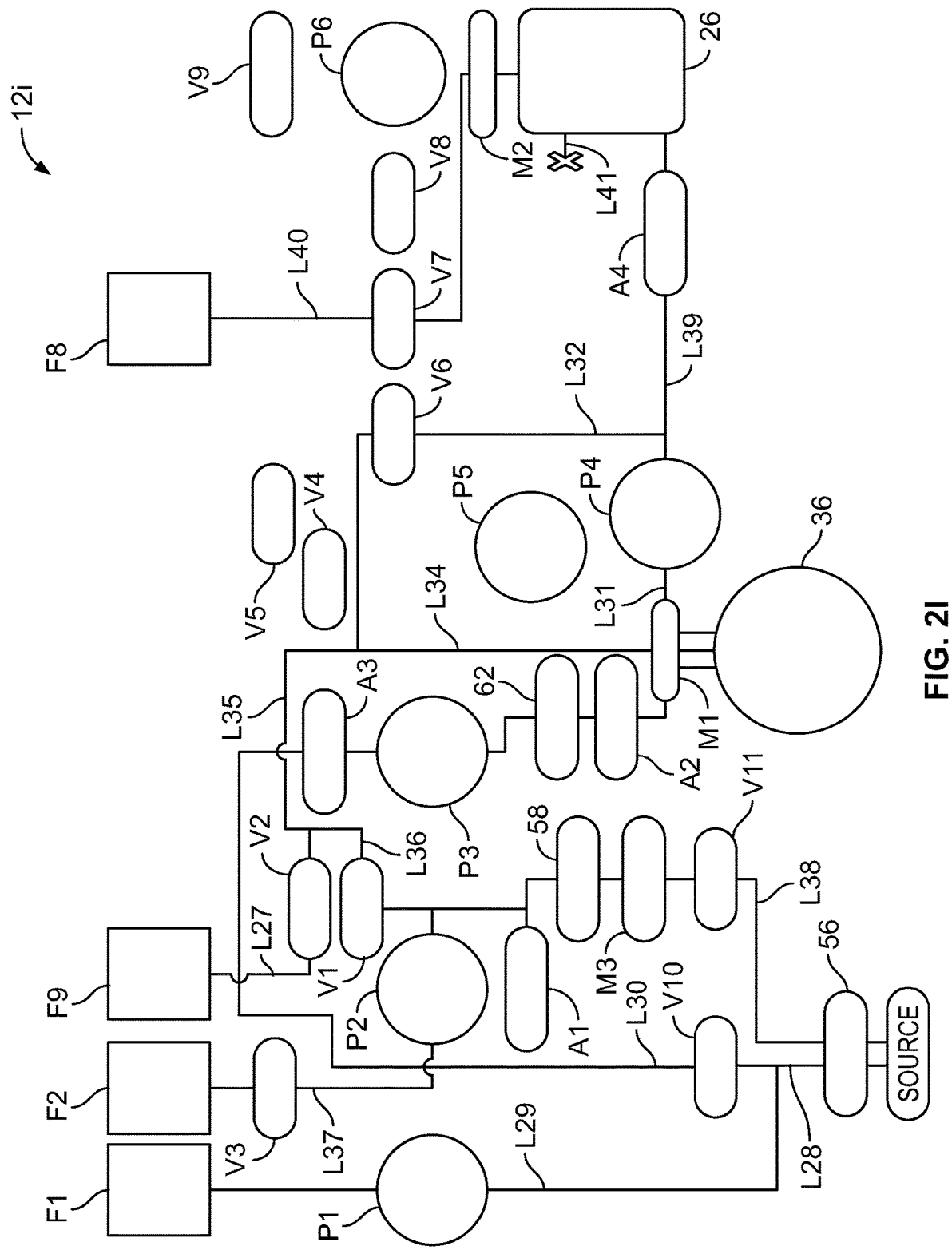
Figure 2J:
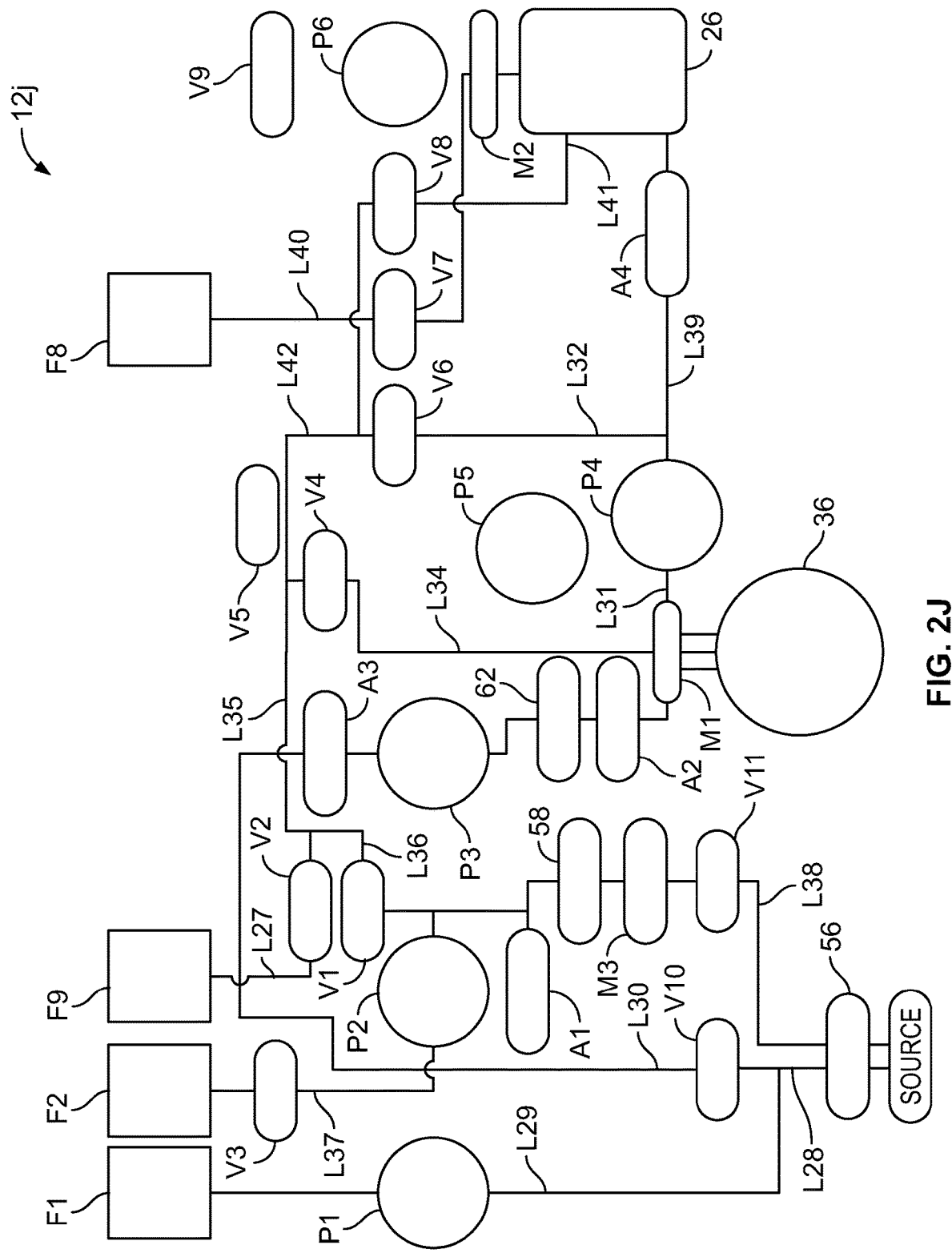
Figure 60:
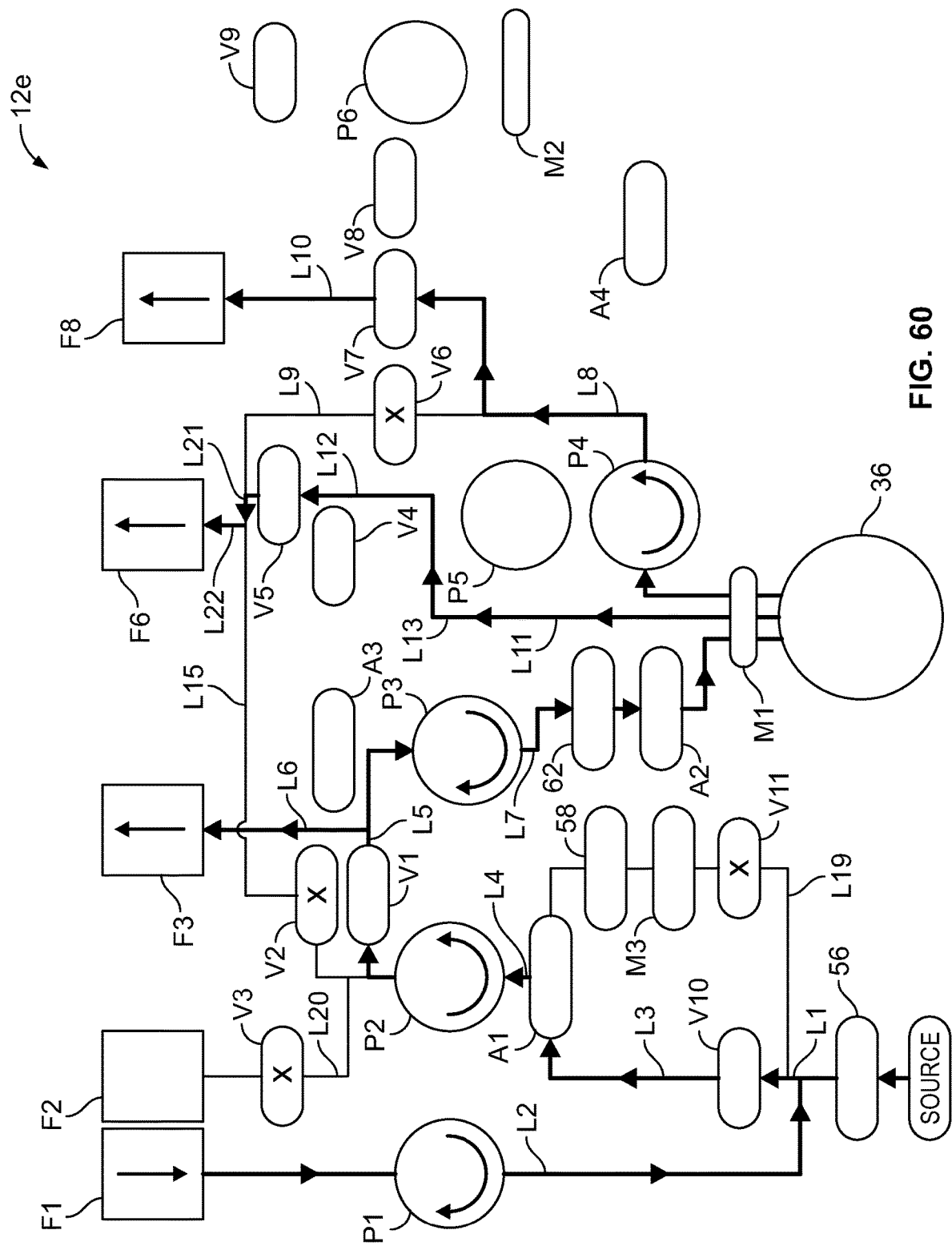
Figure 61:
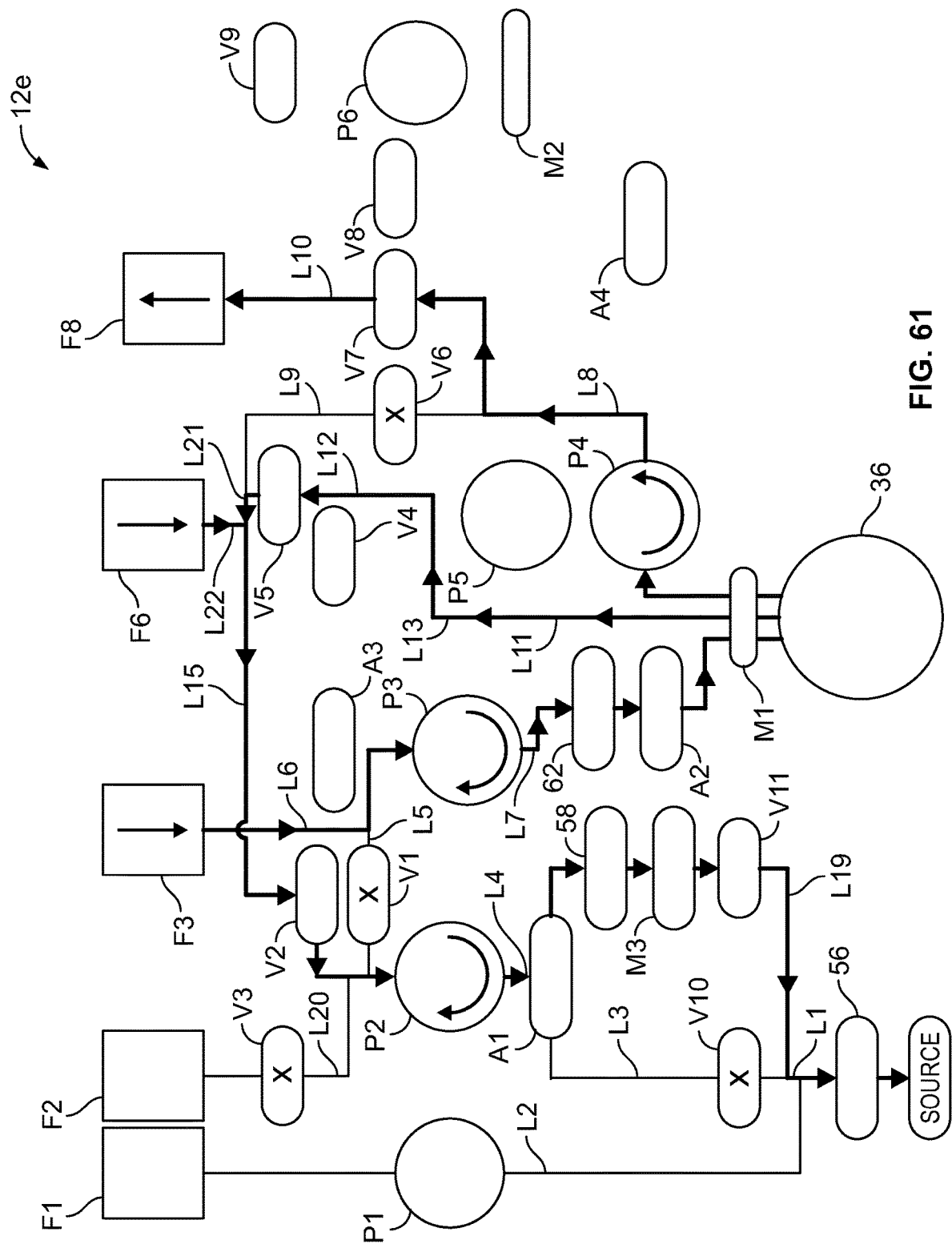
Figure 62:
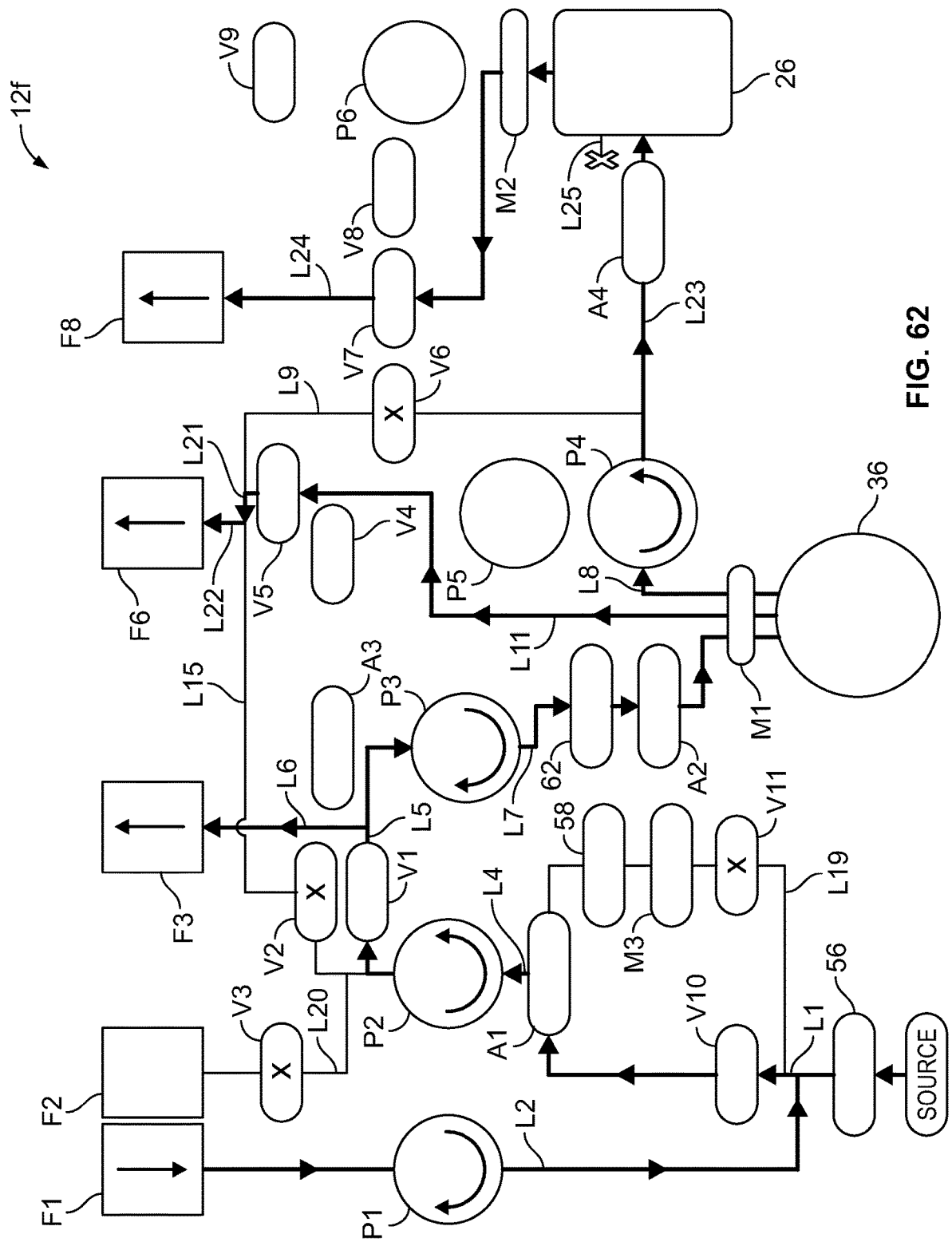
Figure 63:
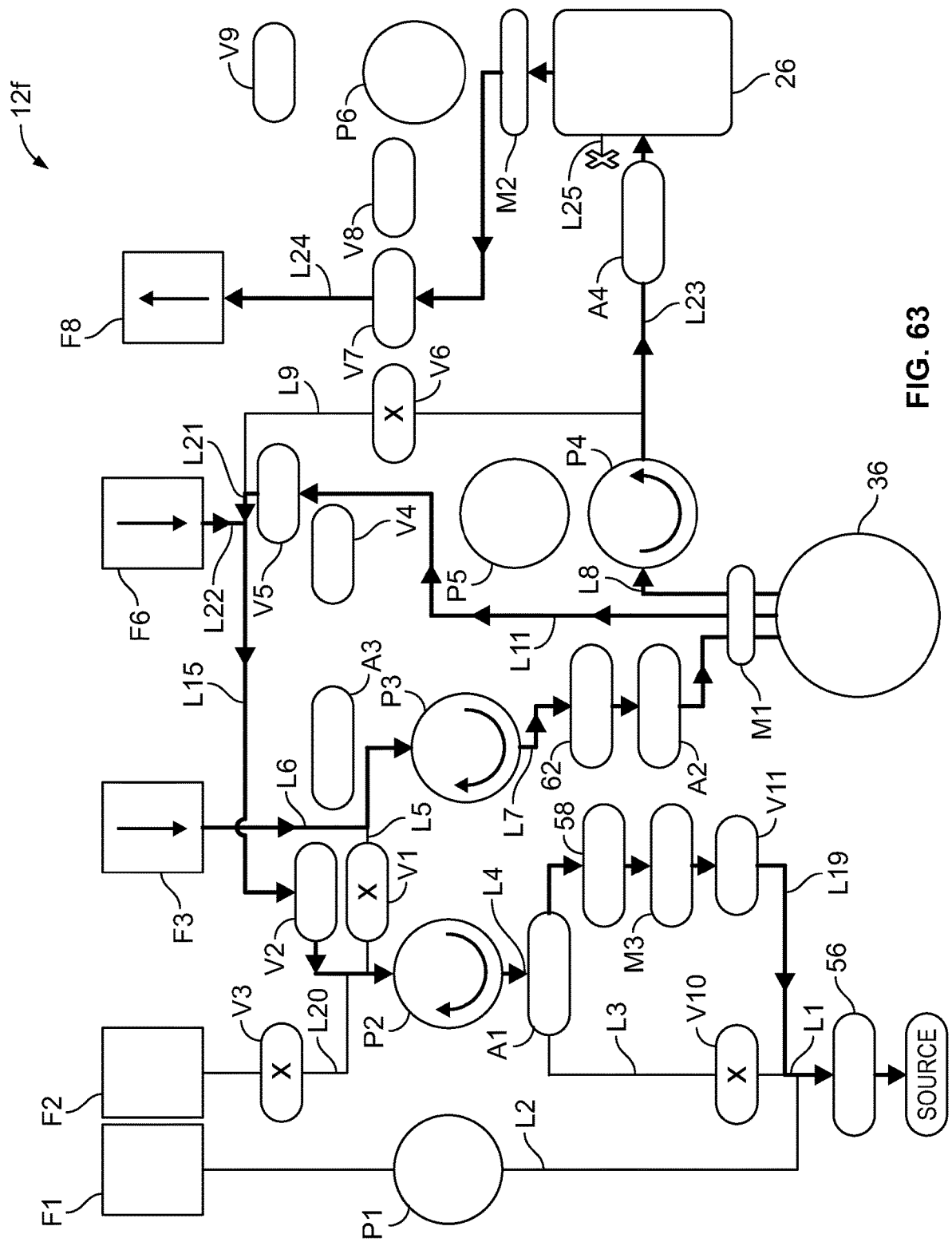
Figure 64:
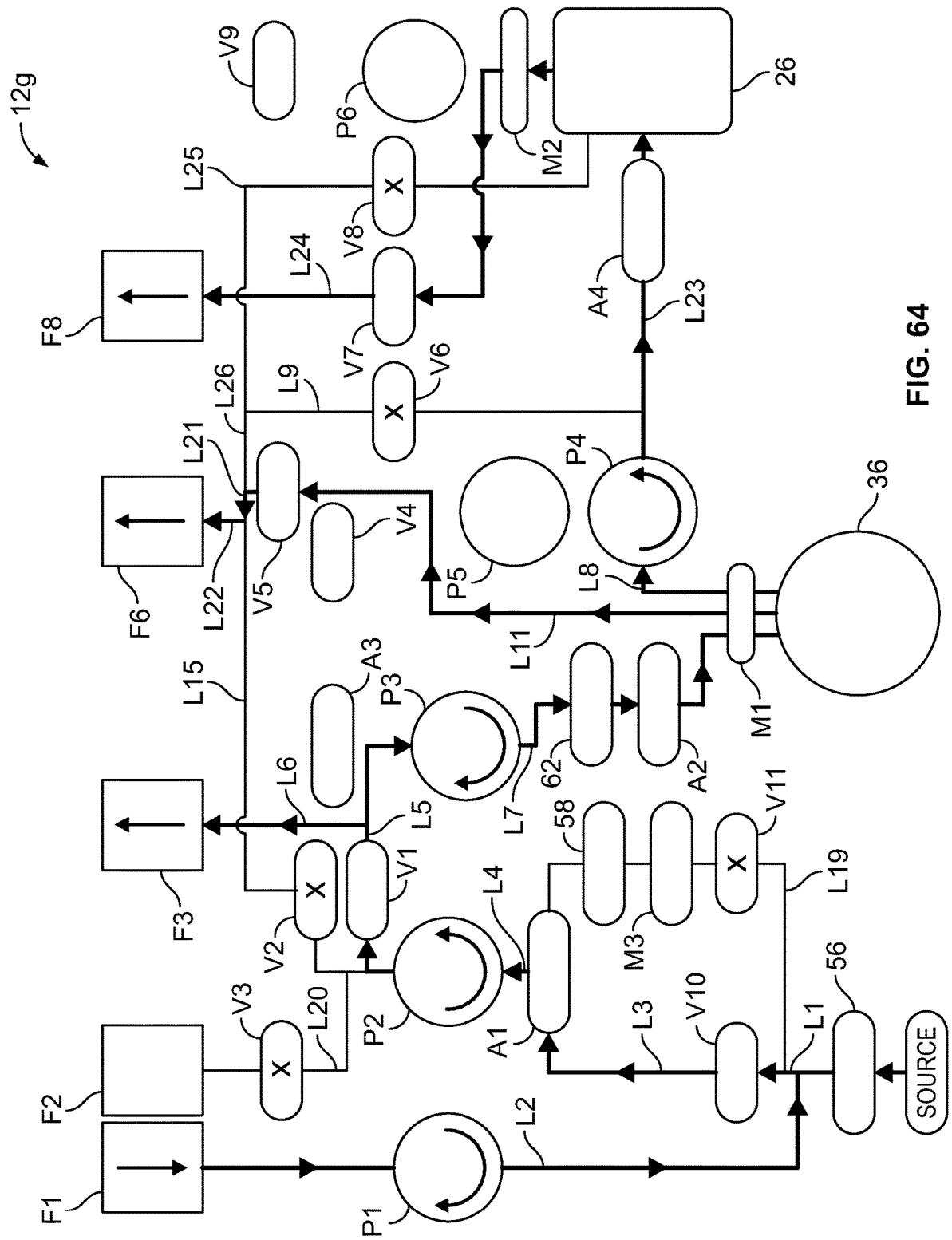
Figure 65:
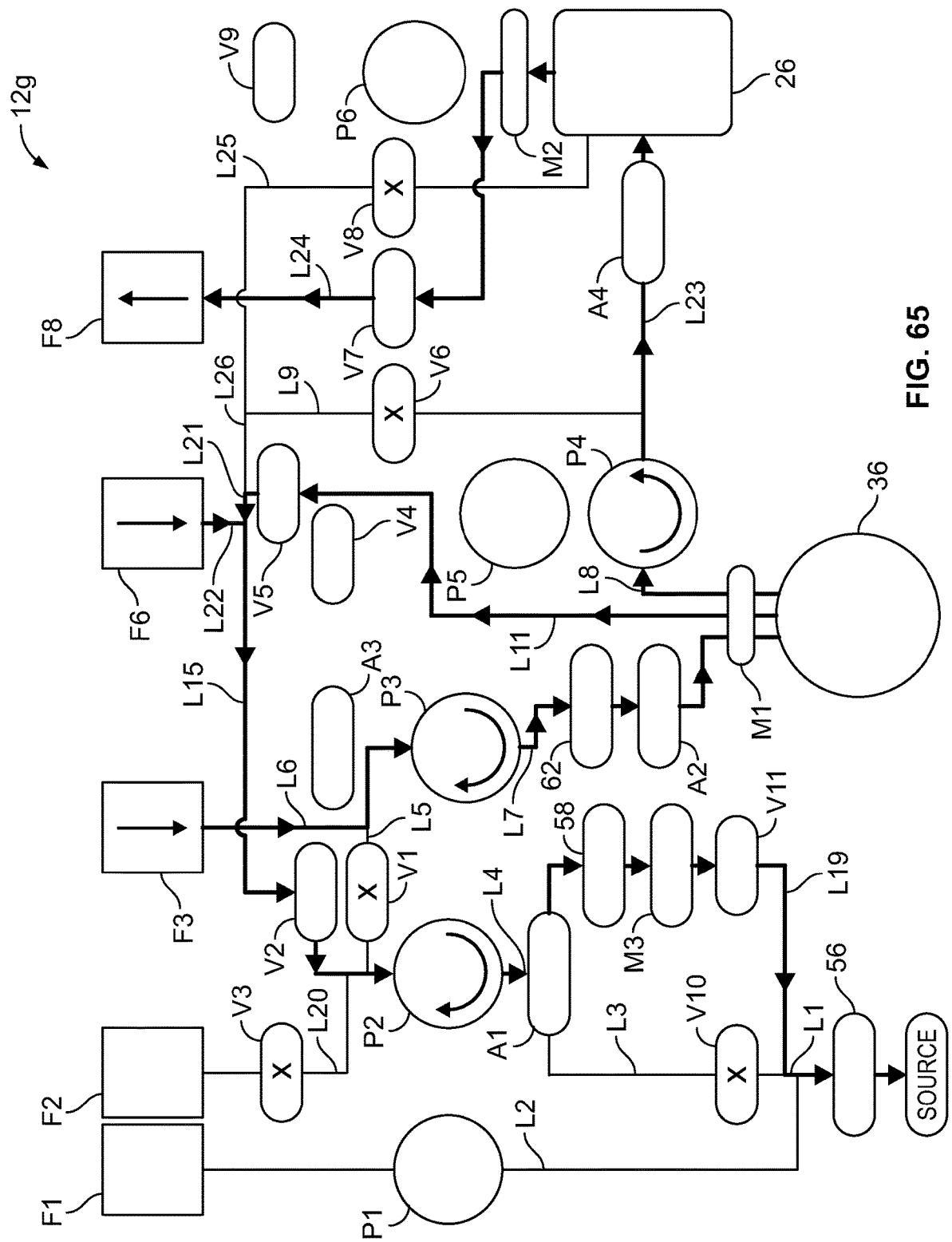
Figure 68:
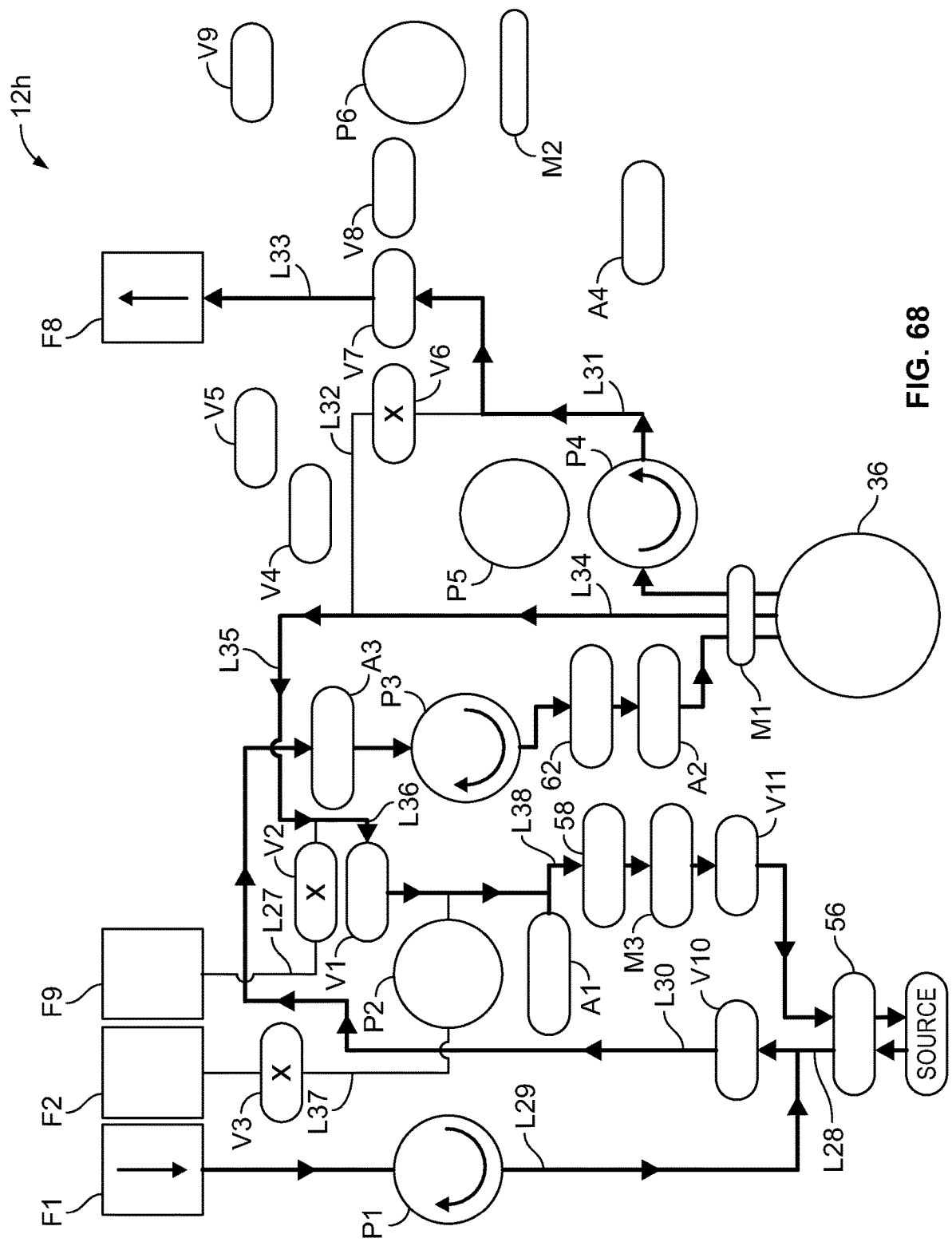
Figure 69:
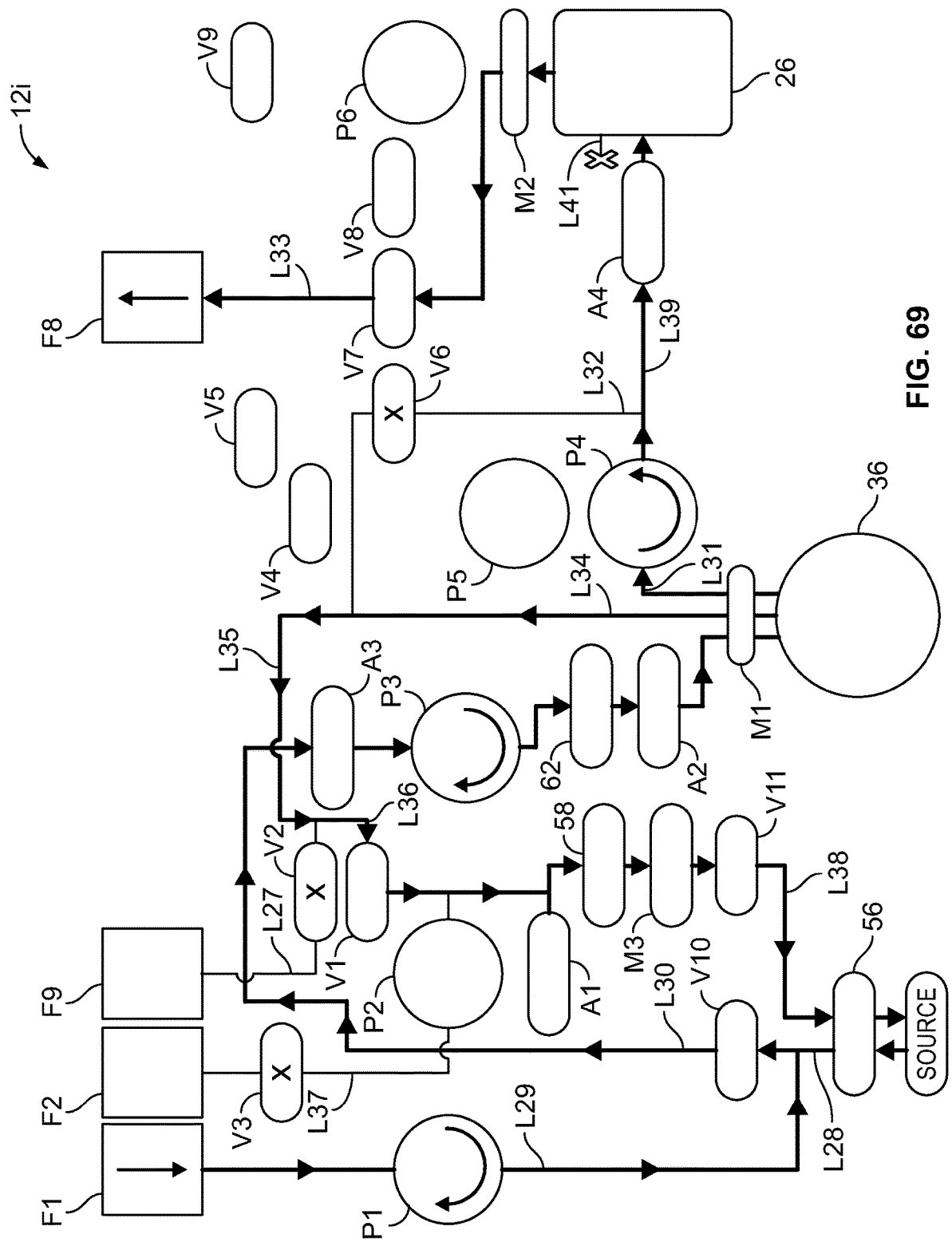
Figure 70:
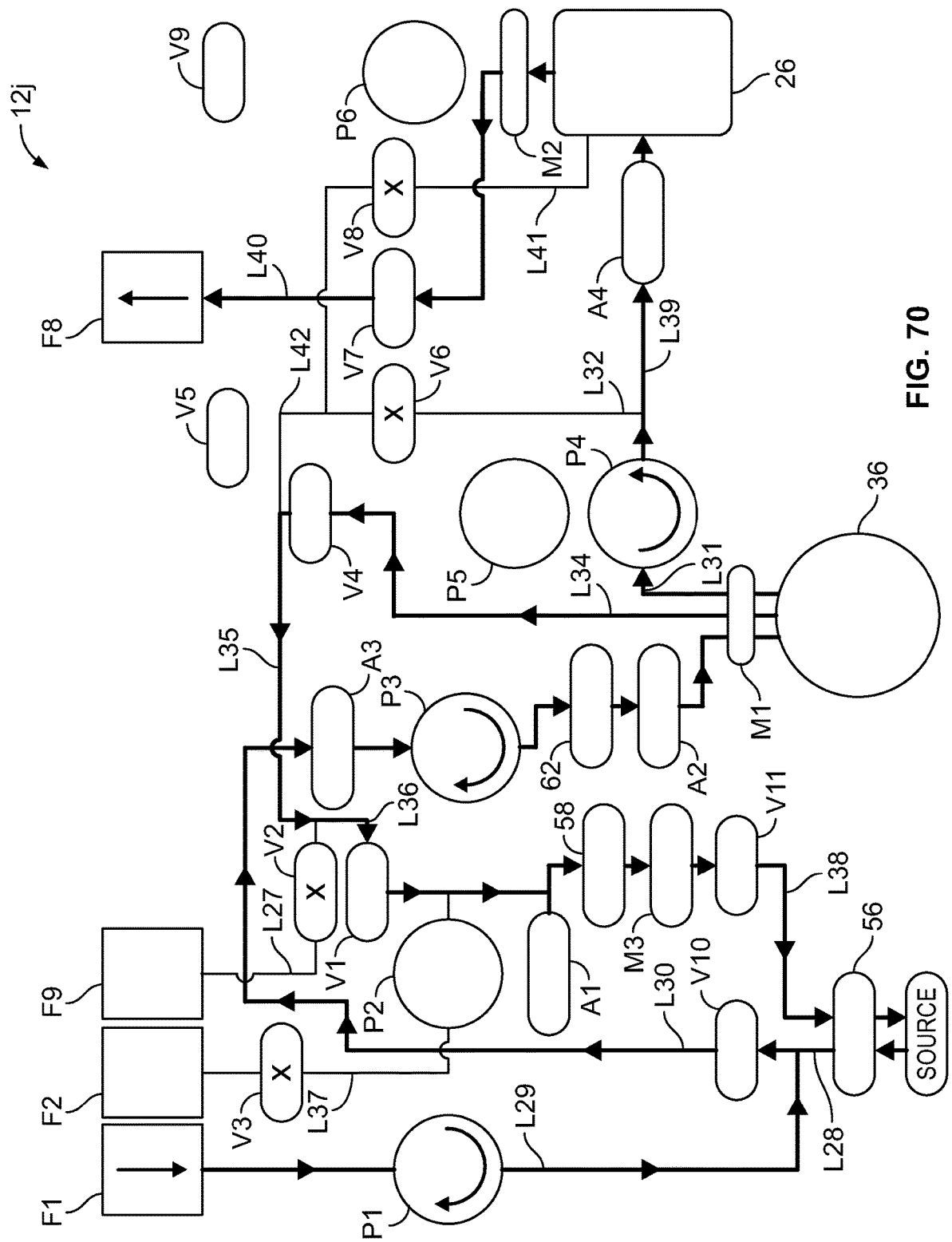
Figure 71:
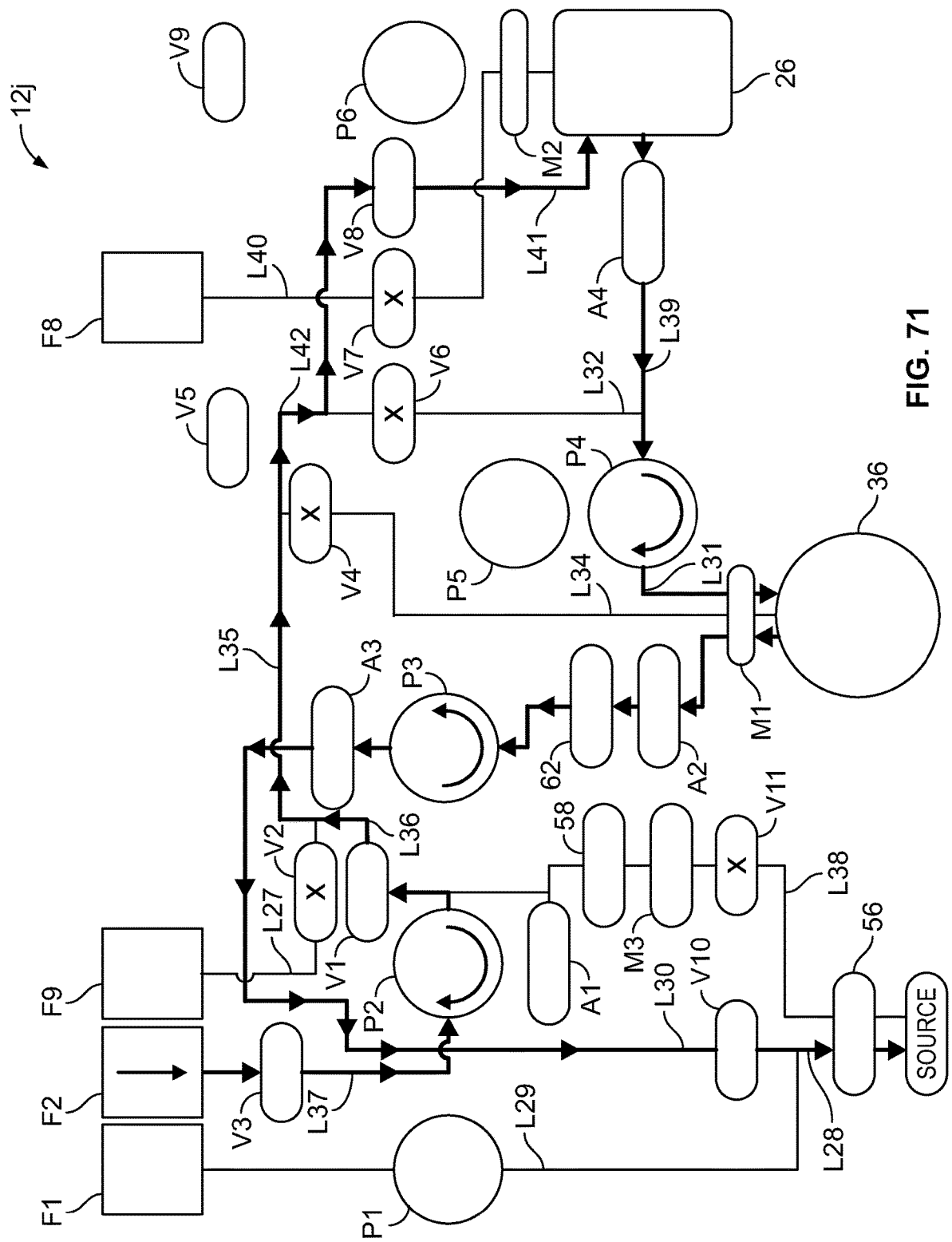

1, showing the system carrying out different fluid flow tasks in connection with separation of blood and collection of red blood cells;

FIGS. 46-49 are schematic views of the fluid flow circuit of FIG. 2B mounted on the blood separation device of FIG. 1, showing the system carrying out different fluid flow tasks in connection with separation of blood and collection of red blood cells and plasma;

FIGS. 50-53 are schematic views of the fluid flow circuit of FIG. 2C mounted on the blood separation device of FIG. 1, showing the system carrying out different fluid flow tasks in connection with separation of blood and collection of red blood cells and filtered plasma;

FIGS. 54-59 are schematic views of the fluid flow circuit of FIG. 2D mounted on the blood separation device of FIG. 1, showing the system carrying out different fluid flow tasks in connection with separation of blood, collection of red blood cells and filtered plasma, and return of cellular blood components filtered from separated plasma;

FIGS. 60 and 61 are schematic views of the fluid flow circuit of FIG. 2E mounted on the blood separation device of FIG. 1, showing the system carrying out different fluid flow tasks in connection with separation of blood and collection of plasma;

FIGS. 62 and 63 are schematic views of the fluid flow circuit of FIG. 2F mounted on the blood separation device of FIG. 1, showing the system carrying out different fluid flow tasks in connection with separation of blood and collection of filtered plasma;

FIGS. 64-67 are schematic view of the fluid flow circuit of FIG. 2G mounted on the blood separation device of FIG. 1, showing the system carrying out different fluid flow tasks in connection with separation of blood, collection of filtered plasma, and return of cellular blood components filtered from separated plasma;

FIG. 68 is a schematic view of the fluid flow circuit of FIG. 2H mounted on the blood separation device of FIG. 1, showing the system carrying out different fluid flow tasks in connection with separation of blood and collection of plasma;

FIG. 69 is a schematic view of the fluid flow circuit of FIG. 2I mounted on the blood separation device of FIG. 1, showing the system carrying out different fluid flow tasks in connection with separation of blood and collection of filtered plasma; and FIGS. 70 and 71 are schematic views of the fluid flow circuit of FIG. 2J mounted on the blood separation device of FIG. 1, showing the system carrying out different fluid flow tasks in connection with separation of blood, collection of filtered plasma; and return of cellular blood components filtered from separated plasma.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-71 show components of a blood or fluid separation system that embodies various aspects of the present subject matter. Generally speaking, the system includes two principal components, a durable and reusable blood separation device 10 (FIG. 1) and a disposable fluid flow circuit 12a-12j (FIGS. 2A-2J, which may be collectively referenced herein as element 12). The blood separation device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the blood separation device 10 to perform a blood processing and collection procedure selected by the operator, as will be described in greater detail

I. The Durable Blood Separation Device

The blood separation device 10 (FIG. 1) is configured as a durable item that is capable of long-term use. It should be understood that the blood separation device 10 of FIG. 1 is merely exemplary of one possible configuration and that blood separation devices according to the present disclosure may be differently configured.

In the illustrated embodiment, the blood separation device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24. The configuration and operation of the spinning membrane separator drive unit 14, the centrifugal separator 16, the controller 18, and selected other components of the blood separation device 10 will be described in greater detail.

In the illustrated embodiment, the generally horizontal portion 22 is intended to rest on an elevated, generally horizontal support surface (e.g., a countertop or a tabletop), but it is also within the scope of the present disclosure for the case 20 to include a support base to allow the case 20 to be appropriately positioned and oriented when placed onto a floor or ground surface. It is also within the scope of the present disclosure for the case 20 to be mounted to a generally vertical surface (e.g., a wall), by either fixedly or removably securing the generally vertical portion 24 of the case 20 to the surface.

The case 20 may be configured to assume only the position or configuration of FIG. 1 or may be configured to move between two or more positions or configurations. For example, in one embodiment, the generally horizontal and vertical portions 22 and 24 are joined by a hinge or pivot, which allows the case 20 to be moved between a functional or open configuration (FIG. 1) in which the generally vertical portion 24 is oriented at approximately 90 degrees to the generally horizontal portion 22 and a transport or closed configuration in which the generally vertical portion 24 is rotated about the hinge to approach the generally horizontal portion 22. In such a reconfigurable embodiment, the generally vertical portion 24 may be considered to be the lid of the case 20, while the generally horizontal portion 22 may be considered to be the base. If the case 20 is so reconfigurable, then it may include a latch for releasably locking the case 20 in its closed configuration and/or a handle, which the operator can grasp for transporting the case 20 in its closed configuration.

While it may be advantageous for the blood separation device 10 to be embodied in a compact, portable case 20, it is also within the scope of the present disclosure for the blood separation device to be embodied in a larger case or fixture that is intended to be installed in a single location and remain in that location for an extended period of time. If the blood separation device is provided as a fixture, it may be provided with more components and functionality than a more portable version.

A. Spinning Membrane Separator Drive Unit

The illustrated blood separation device 10 includes a spinner support or spinning membrane separator drive unit 14 (FIG. 1) for accommodating a generally cylindrical spinning membrane separator 26 of the fluid flow circuit 12 (FIGS. 2C, 2D, 2F, 2G, 2I and 2J). U.S. Pat. No. 5,194,145 describes an exemplary spinning membrane separator drive unit that would be suitable for incorporation into the blood separation device 10, but it should be understood that the spinning membrane separator drive unit 14 may be differently configured without departing from the scope of the present disclosure.

The illustrated spinning membrane separator drive unit 14 has a base 28 configured to receive a lower portion of the spinning membrane separator 26 and an upper end cap 30 to receive an upper portion of the spinning membrane separator 26. Preferably, the upper end cap 30 is positioned directly above the base 28 to orient a spinning membrane separator 26 received by the spinning membrane separator drive unit 14 vertically and to define a vertical axis about which the spinning membrane separator 26 is spun. While it may be advantageous for the spinning membrane separator drive unit 14 to vertically orient a spinning membrane separator 26, it is also within the scope of the present disclosure for the spinning membrane separator 26 to be differently oriented when mounted to the blood separation device 10.

In one embodiment, one of the components of the spinning membrane separator drive unit 14 is movable with respect to the other component, which may allow differently sized spinning membrane separators 26 to be received by the spinning membrane separator drive unit 14. For example, the upper end cap 30 may be translated vertically with respect to the base 28 and locked in a plurality of different positions, with each locking position corresponding to a differently sized spinning membrane separator 26.

At least one of the base 28 and the upper end cap 30 is configured to spin one or more components of the spinning membrane separator 26 about the axis defined by the spinning membrane separator drive unit 14. The mechanism by which the spinning membrane separator drive unit 14 spins one or more components of the spinning membrane separator 26 may vary without departing from the scope of the present disclosure. In one embodiment, a component of the spinning membrane separator 26 to be spun includes at least one element configured to be acted upon by a magnet (e.g., a metallic material), while the spinning membrane separator drive unit 14 includes a magnet (e.g., a series of magnetic coils or semi-circular arcs). By modulating the magnetic field acting upon the aforementioned element of the spinning membrane separator 26, the component or components of the spinning membrane separator 26 may be made to spin in different directions and at varying speeds. In other embodiments, different mechanisms may be employed to spin the component or components of the spinning membrane separator 26.

Regardless of the mechanism by which the spinning membrane separator drive unit 14 spins the component or components of the spinning membrane separator 26, the component or components of the spinning membrane separator 26 is preferably spun at a speed that is sufficient to create Taylor vortices in a gap between the spinning component and a stationary component of the spinning membrane separator 26 (or a component that spins at a different speed). Fluid to be separated within the spinning membrane separator 26 flows through this gap, and filtration may be dramatically improved by the creation of Taylor vortices.

B. Centrifugal Separator

Figure 3:
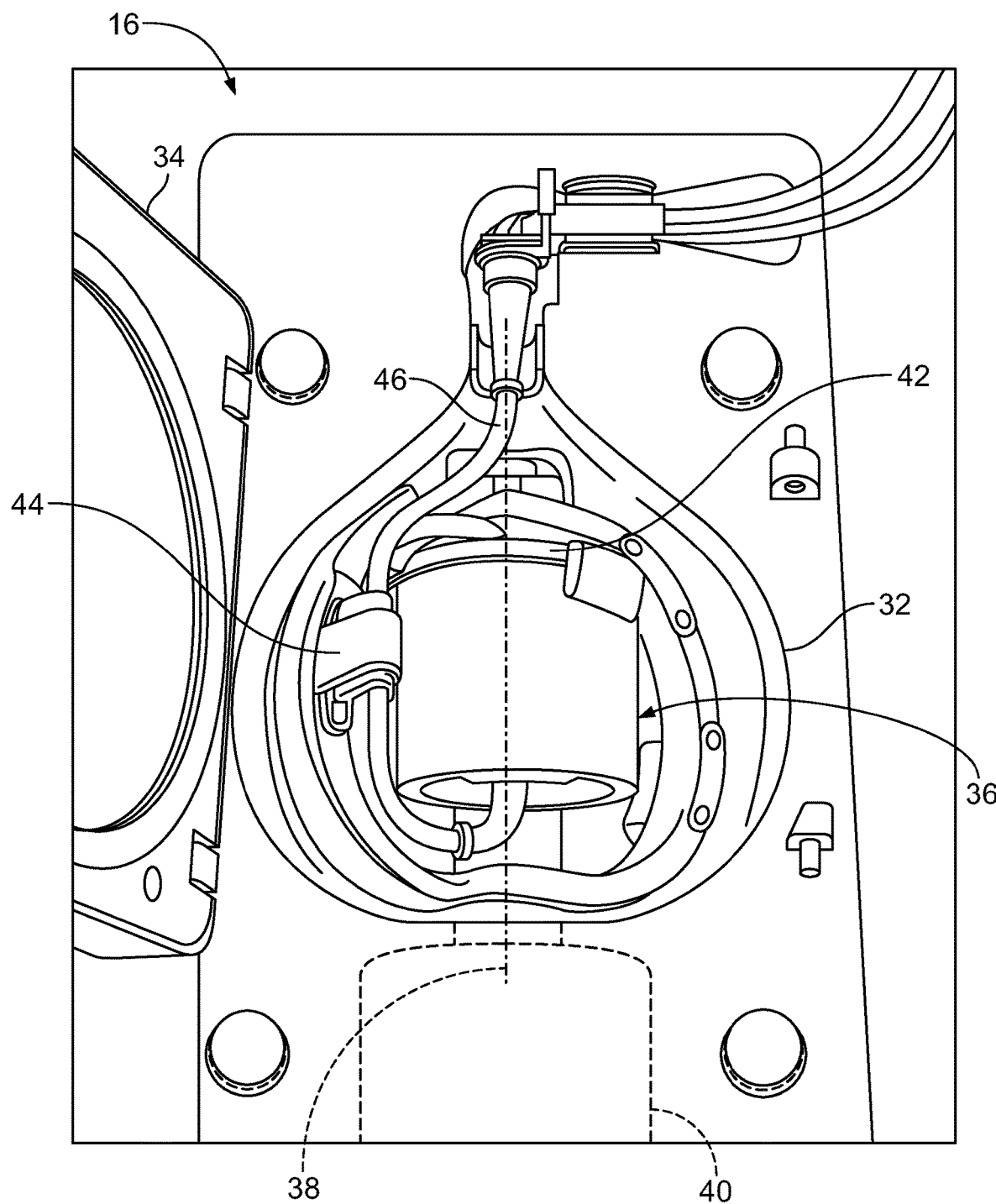
FIG. 3 is a perspective view of an exemplary centrifugal separator of the blood separation device of FIG. 1, with the centrifugal separation chamber of a fluid flow circuit mounted therein.

As for the centrifugal separator 16, it includes a centrifuge compartment 32 that may receive the other components of the centrifugal separator 16 (FIG. 3). The centrifuge compartment 32 may include a lid 34 that is opened to insert and remove a centrifugal separation chamber 36 of the fluid flow circuit 12. During a separation procedure, the lid 34 may be closed with the centrifugal separation chamber 36 positioned within the centrifuge compartment 32, as the centrifugal separation chamber 36 is spun or rotated about an axis 38 under the power of an electric drive motor or rotor 40 of the centrifugal separator 16.

Figure 4:
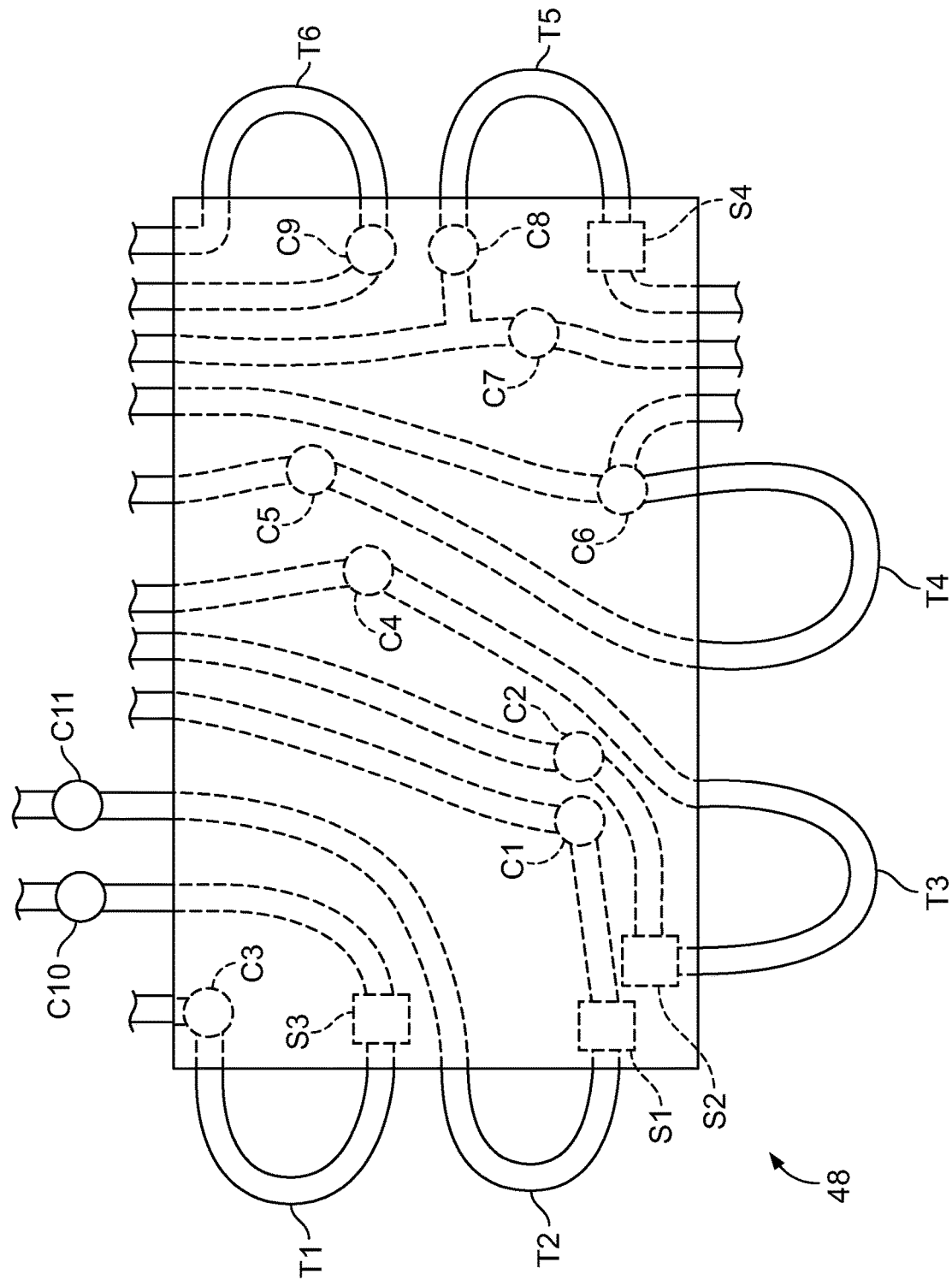
FIG. 4 is a top plan view of an exemplary cassette of a fluid flow circuit, which can be actuated to perform a variety of different blood processing procedures in association with the blood separation device shown in FIG. 1.

The particular configuration and operation of the centrifugal separator 16 depends upon the particular configuration of the centrifugal separation chamber 36 of the fluid flow circuit 12. In one embodiment, the centrifugal separator 16 is similar in structure and operation to that of the ALYX® system manufactured by Fenwal, Inc. of Lake Zurich, Illinois, which is an affiliate of Fresenius Kabi AG of Bad Homburg, Germany, as described in greater detail in U.S. Pat. No. 8,075,468, which is incorporated herein by reference. More particularly, the centrifugal separator 16 may include a carriage or support 42 that holds the centrifugal separation chamber 36 and a yoke member 44. The yoke member 44 engages an umbilicus 46 of the fluid flow circuit 12, which extends between the centrifugal separation chamber 36 and a cassette 48 of the fluid flow circuit 12 (FIG. 4). The yoke member 44 causes the umbilicus 46 to orbit around the centrifugal separation chamber 36 at a one omega rotational speed. The umbilicus 46 twists about its own axis as it orbits around the centrifugal separation chamber 36. The twisting of the umbilicus 46 about its axis as it rotates at one omega with the yoke member 44 imparts a two omega rotation to the centrifugal separation chamber 36, according to known design. The relative rotation of the yoke member 44 at a one omega rotational speed and the centrifugal separation chamber 36 at a two omega rotational speed keeps the umbilicus 46 untwisted, avoiding the need for rotating seals.

Figure 6:
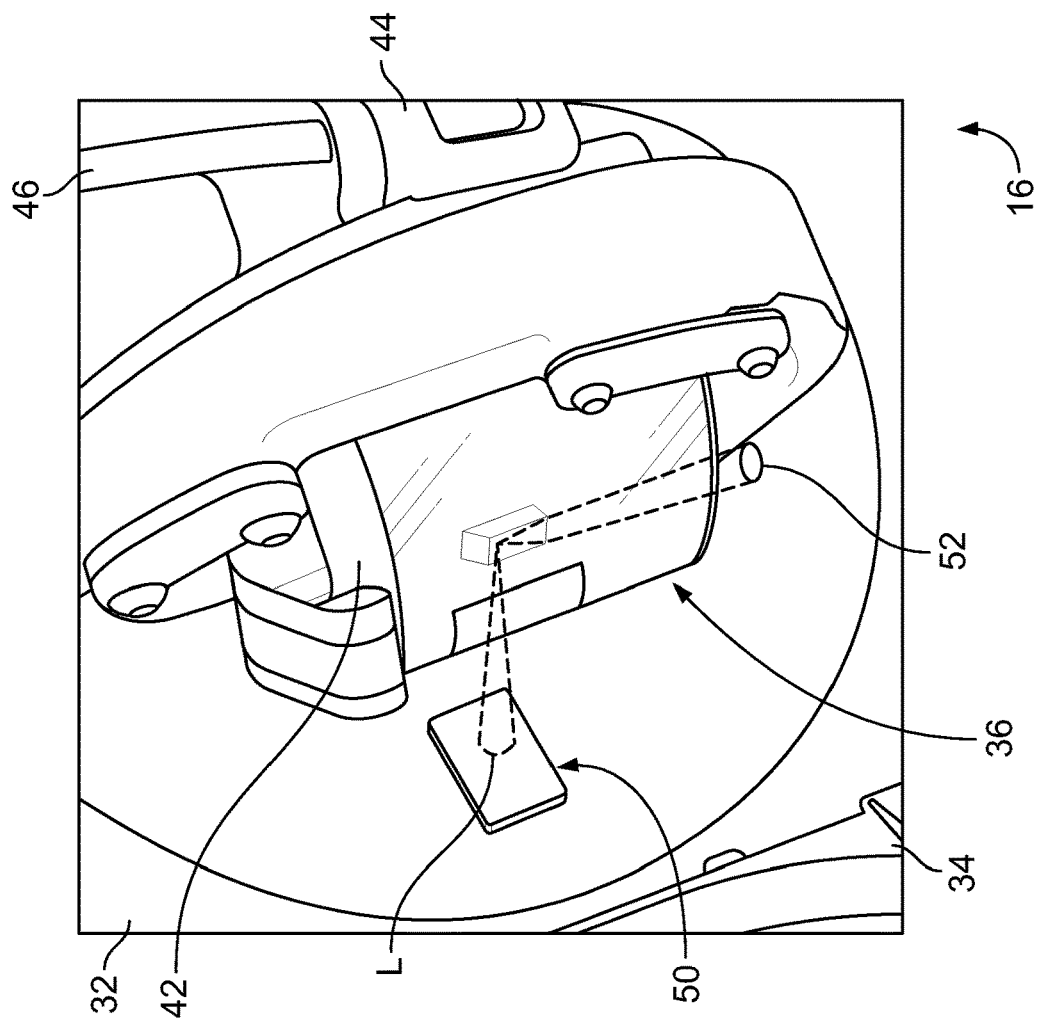
FIG. 6 is a perspective view of the centrifugal separator of FIG. 3, with the light source operating to transmit a light beam to a light detector of the interface monitoring system.
Figure 5:
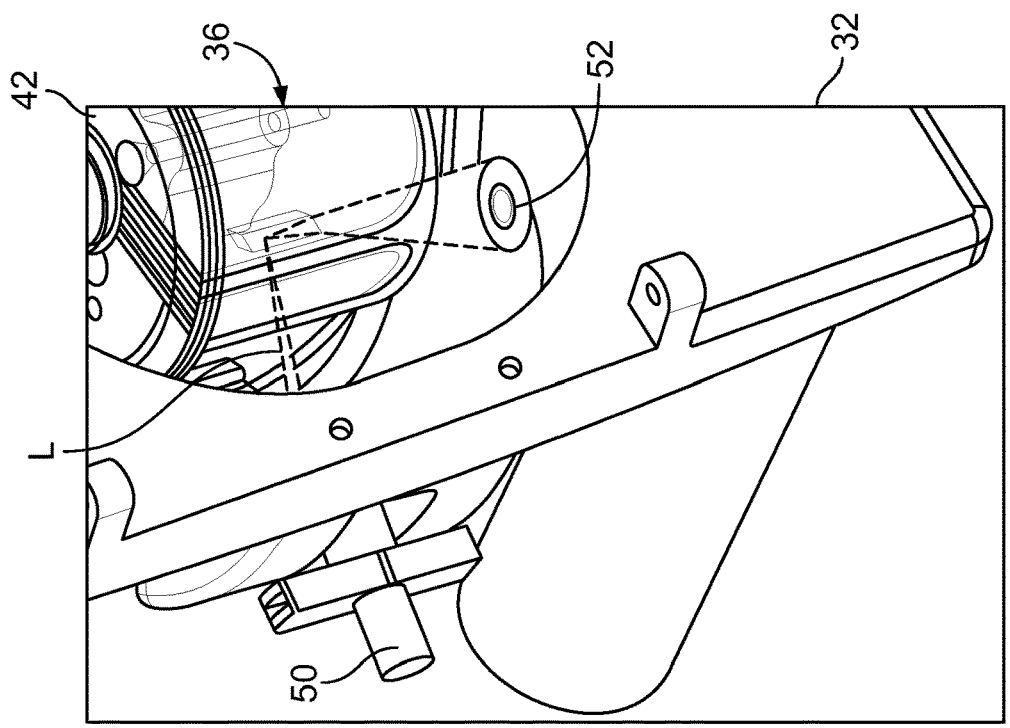
FIG. 5 is a perspective view of the centrifugal separator of FIG. 3, with selected portions thereof broken away to show a light source of an interface monitoring system.
Figure 7:
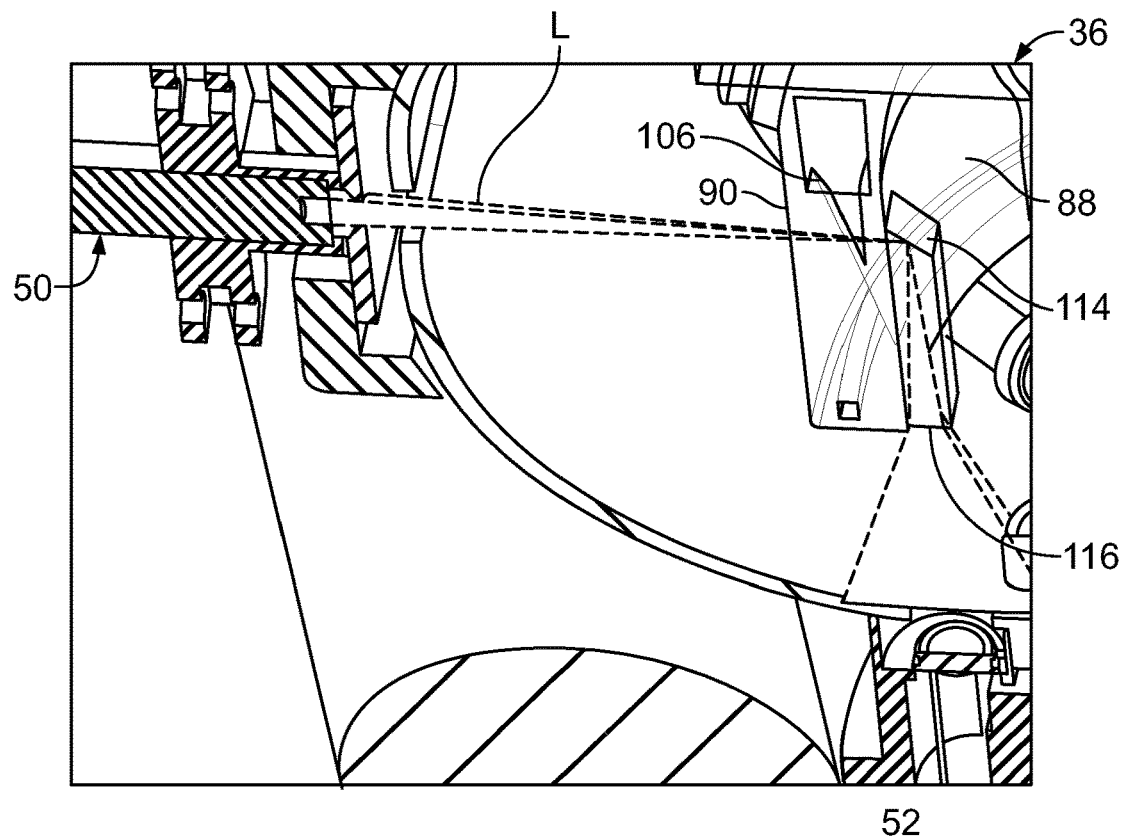
FIG. 7 is a perspective view of the centrifugal separator of FIG. 3, with selected portions thereof broken away to show the light source and light detector of the interface monitoring system.

Blood is introduced into the centrifugal separation chamber 36 by the umbilicus 46, with the blood being separated (e.g., into a layer of less dense components, such as platelet-rich plasma, and a layer of more dense components, such as packed red blood cells) within the centrifugal separation chamber 36 as a result of centrifugal forces as it rotates. Components of an interface monitoring system may be positioned within the centrifuge compartment 32 to oversee separation of blood within the centrifugal separation chamber 36. As shown in FIGS. 5-7, the interface monitoring system may include a light source 50 and a light detector 52, which is positioned and oriented to receive at least a portion of the light emitted by the light source 50. Preferably, the light source 50 and the light detector 52 are positioned on stationary surfaces of the centrifuge compartment 32, but it is also within the scope of the present disclosure for one or both to be mounted to a movable component of the centrifugal separator 16 (e.g., to the yoke member 44, which rotates at a one omega speed).

The orientation of the various components of the interface monitoring system depends at least in part on the particular configuration of the centrifugal separation chamber 36, which will be described in greater detail herein. In general, though, the light source 50 emits a light beam (e.g., a laser light beam) through the separated blood components within the centrifugal separation chamber 36 (which may be formed of a material that substantially transmits the light or at least a particular wavelength of the light without absorbing it). A portion of the light reaches the light detector 52, which transmits a signal to the controller 18 that is indicative of the location of an interface between the separated blood components. If the controller 18 determines that the interface is in the wrong location (which can affect the separation efficiency of the centrifugal separator 16 and/or the quality of the separated blood components), then it can issue commands to the appropriate components of the blood separation device 10 to modify their operation so as to move the interface to the proper location.

C. Other Components of the Blood Separation Device

In addition to the spinning membrane separator drive unit 14 and the centrifugal separator 16, the blood separation device 10 may include other components compactly arranged to aid blood processing.

The generally horizontal portion 22 of the case 20 of the illustrated blood separation device 10 includes a cassette station 54, which accommodates a cassette 48 of the fluid flow circuit 12 (FIG. 4). In one embodiment, the cassette station 54 is similarly configured to the cassette station of U.S. Pat. No. 5,868,696 (which is incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 2 and 4). Depending on the configuration of the fluid flow circuit 12, its cassette 48 may not include a valve station C1-C9 for each valve V1-V9 of the cassette station 54, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 54 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the blood source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifugal separation chamber 36. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The blood separation device 10 may also include a plurality of pumps P1-P6 (which may be collectively referred to as a pump assembly) cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 4) and may be selectively operated under command of the controller 18 to cause fluid to flow through a portion of the fluid flow circuit 12, as will be described in greater detail. In one embodiment, all or a portion of the cassette station 54 may be capable of translational motion in and out of the case 20 to allow for automatic loading of the tubing loops T1-T6 into the associated pump P1-P6.

The illustrated blood separation device 10 also includes a centrifugal separator sensor M1 for determining one or more properties of fluids flowing out of and/or into the centrifugal separator 16. If the fluid flowing out of the centrifugal separator 16 includes red blood cells, the centrifugal separator sensor M1 may be configured to determine the hematocrit of the fluid. If the fluid flowing out of the centrifugal separator 16 is platelet-rich plasma, the centrifugal separator sensor M1 may be configured to determine the platelet concentration of the platelet-rich plasma. The centrifugal separator sensor M1 may detect the one or more properties of a fluid by optically monitoring the fluid as it flows through tubing of the fluid flow circuit 12 or by any other suitable approach. The controller 18 may receive signals from the centrifugal separator sensor M1 that are indicative of the one or more properties of fluid flowing out of the centrifugal separator 16 and use the signals to optimize the separation procedure based upon that property or properties. If the property or properties is/are outside of an acceptable range, then the controller 18 may initiate an alarm or error condition to alert an operator to the condition. A suitable device and method for monitoring hematocrit and/or platelet concentration is described in U.S. Pat. No. 6,419,822 (which is incorporated herein by reference), but it should be understood that a different approach may also be employed for monitoring hematocrit and/or platelet concentration of fluid flowing out of the centrifugal separator 16.

The illustrated blood separation device 10 further includes a spinner outlet sensor M2, which accommodates tubing of the fluid flow circuit 12 that flows a separated substance out of the spinning membrane separator 26. The spinner outlet sensor M2 monitors the substance to determine one or more properties of the substance, and may do so by optically monitoring the substance as it flows through the tubing or by any other suitable approach. In one embodiment, separated plasma flows through the tubing, in which case the spinner outlet sensor M2 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) or by any other suitable device and/or method.

The illustrated blood separation device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F9 of the fluid flow circuit 12 (FIGS. 2A-2J). The containers F1-F9 receive blood components or waste products separated during processing or intravenous fluids or additive fluids. Each weight scale W1-W6 transmits to the controller 18 a signal that is indicative of the weight of the fluid within the associated container F1-F9 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 12 or other suitably sized and configured objects.

D. Controller

According to an aspect of the present disclosure, the blood separation device 10 includes a controller 18, which is suitably configured and/or programmed to control operation of the blood separation device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the blood separation device 10.

The controller 18 is configured and/or programmed to execute at least one blood processing application but, more advantageously, is configured and/or programmed to execute a variety of different blood processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and an MNC collection procedure. Additional or alternative procedure applications can be included without departing from the scope of the present disclosure.

More particularly, in carrying out any one of these blood processing applications, the controller 18 is configured and/or programmed to control one or more of the following tasks: drawing blood into a fluid flow circuit 12 mounted to the blood separation device 10, conveying blood through the fluid flow circuit 12 to a location for separation (i.e., into a spinning membrane separator 26 or centrifugal separation chamber 36 of the fluid flow circuit 12), separating the blood into two or more components as desired, and conveying the separated components into storage containers, to a second location for further separation (e.g., into whichever of the spinning membrane separator 26 and centrifugal separation chamber 36 that was not used in the initial separation stage), or to a recipient (which may be the source from which the blood was originally drawn).

This may include instructing the spinning membrane separator drive unit 14 and/or the centrifugal separator 16 to operate at a particular rotational speed and instructing a pump P1-P6 to convey fluid through a portion of the fluid flow circuit 12 at a particular flow rate. Hence, while it may be described herein that a particular component of the blood separation device 10 (e.g., the spinning membrane separator drive unit 14 or the centrifugal separator 16) performs a particular function, it should be understood that that component is being controlled by the controller 18 to perform that function.

As will be described, a procedure may call for the use of both the centrifugal separator 16 and the spinning membrane separator drive unit 14, in which case a properly programmed controller 18 is especially important to coordinate the operation of these two components, along with the other components of the blood separation device 10 to ensure that flow to and from the centrifugal separator 16 and spinning membrane separator drive unit 14 is at the proper level and that the components are functioning properly to process the blood circulating through the fluid flow circuit 12.

Before, during, and after a procedure, the controller 18 may receive signals from various components of the blood separation device 10 (e.g., the pressure sensors A1-A4) to monitor various aspects of the operation of the blood separation device 10 and characteristics of the blood and separated blood components as they flow through the fluid flow circuit 12. If the operation of any of the components and/or one or more characteristics of the blood or separated blood components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring system. The signals that the controller 18 receives from the light detector 52 are indicative of the location of an interface between the separated blood components within the centrifugal separation chamber 36. If the controller 18 determines that the interface is in the wrong location, then it can issue commands to the appropriate components of the blood separation device 10 to modify their operation so as to move the interface to the proper location. For example, the controller 18 may instruct one of the pumps P1-P6 to cause blood to flow into the centrifugal separation chamber 36 at a different rate and/or for a separated blood component to be removed from the centrifugal separation chamber 36 at a different rate and/or for the centrifugal separation chamber 36 to be spun at a different speed by the centrifugal separator 16. A particular protocol carried out by the interface control module in adjusting the position of the interface within the centrifugal separation chamber 36 will be described in greater detail with respect to an exemplary centrifugal separation chamber 36.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIGS. 2A-2J), it is intended to be a sterile, single use, disposable item. Before beginning a given blood processing and collection procedure, the operator loads various components of the fluid flow circuit 12 in the case 20 in association with the blood separation device 10. The controller 18 implements the procedure based upon preset protocols, taking into account other input from the operator. Upon completing the procedure, the operator removes the fluid flow circuit 12 from association with the blood separation device 10. The portions of the fluid flow circuit 12 holding the collected blood component or components (e.g., collection containers or bags) are removed from the case 20 and retained for storage, transfusion, or further processing. The remainder of the fluid flow circuit 12 is removed from the case 20 and discarded.

A variety of different disposable fluid flow circuits 12a-12j may be used in combination with the blood separation device 10, with the appropriate fluid flow circuit depending on the separation procedure to be carried out using the system.

Accordingly, different fluid flow circuits will be described in connection with particular separation procedures. Generally speaking, though, the fluid flow circuit 12 includes a cassette 48 (FIG. 4), to which the other components of the fluid flow circuit 12 are connected by flexible tubing. The other components may include a plurality of fluid containers F1-F9 (for holding blood, a separated blood component, an intravenous fluid, or an additive solution, for example), one or more blood source access devices (e.g., a connector for accessing blood within a fluid container), and a spinning membrane separator 26 (FIGS. 8 and 9) and/or a centrifugal separation chamber 36 (FIGS. 10-17).

B. Cassette and Tubing

The cassette 48 (FIG. 4) provides a centralized, programmable, integrated platform for all the pumping and many of the valving functions required for a given blood processing procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the blood separation device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the blood separation device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure, as will be described in greater detail. Certain procedures require fewer than all of the sensor stations, valve stations, and/or tubing loops illustrated in the exemplary cassette 48 of FIG. 4, such that it should be understood that the cassettes of different fluid flow circuits 12 may be differently configured (e.g., with fewer sensor stations, valve stations, and/or tubing loops) without departing from the scope of the present disclosure.

Additional tubing extends from the side surface of the cassette 48 to connect to the other components of the fluid flow circuit 12, such as the various fluid containers F1-F9, the spinning membrane separator 26, and the centrifugal separation chamber 36. The number and content of the various fluid containers F1-F9 depends upon the procedure for which the fluid flow circuit 12 is used, so they will be described in greater detail with respect to the particular procedures. If the fluid flow circuit 12 includes a centrifugal separation chamber 36, then the tubing connected to it (which includes one inlet tube and two outlet tubes) may be aggregated into an umbilicus 46 (FIG. 3) that is engaged by the yoke member 44 of the centrifugal separator 16 (as described above) to cause the umbilicus 46 to orbit around and spin or rotate the centrifugal separation chamber 36 during a separation procedure.

Various additional components may be incorporated into the tubing leading out of the cassette 48 or into one of the cavities of the cassette 48. For example, as shown in FIGS. 2A-2J, a manual clamp 56 may be associated with a line or lines leading to the blood source and/or fluid recipient, a return line filter 58 (e.g., a microaggregate filter) may be associated with a line leading to a fluid recipient, filters 60 may be positioned upstream of one or more of the fluid containers to remove a substance (e.g., leukocytes) from a separated component (e.g., red blood cells) flowing into the fluid container, and/or an air trap 62 may be positioned on a line upstream of the centrifugal separation chamber 36.

C. Spinning Membrane Separator

Figure 8:
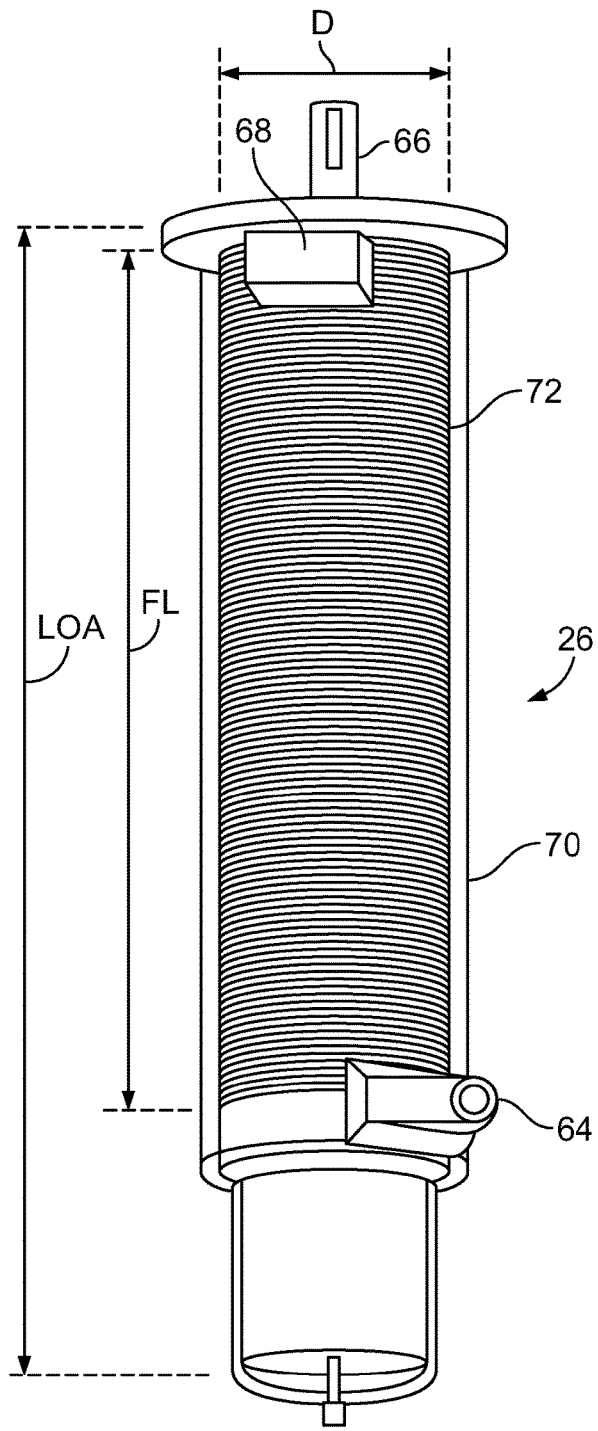
FIG. 8 is a perspective view of an exemplary spinning membrane separator of a fluid flow circuit.
Figure 9:
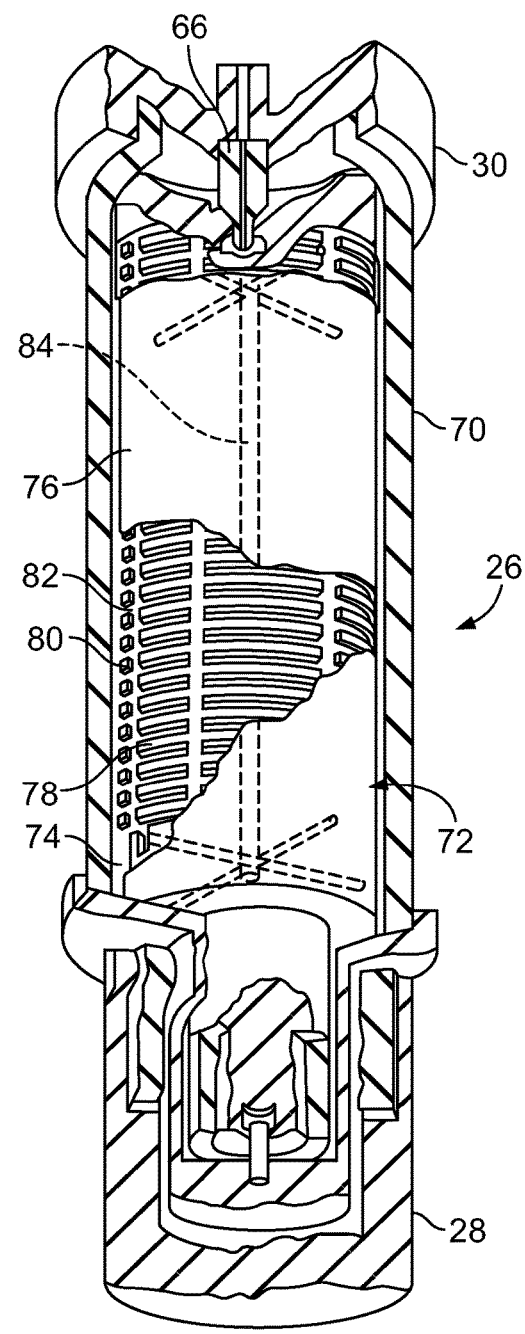
FIG. 9 is a perspective view of the spinning membrane separator of FIG. 8 and a portion of a spinning membrane separator drive unit, with portions of both being cut away for illustrative purposes.

Turning to FIGS. 8 and 9, a spinning membrane separator 26 is shown. As will be described in greater detail, the spinning membrane separator 26 may be used to separate plasma from cellular blood components to produce a filtered plasma product. The spinning membrane separator 26 (if provided) is associated with the remainder of the fluid flow circuit 12 by an inlet port 64 and two outlet ports 66 and 68. The inlet port 64 is shown as being associated with a bottom end or portion of the spinning membrane separator 26, while the outlet ports 66 and 68 are associated with an upper end or portion of the spinning membrane separator 26, but it is within the scope of the present disclosure for the spinning membrane separator 26 to be inverted, with fluid entering an upper end or portion of the spinning membrane separator 26 and fluid exiting a lower end or portion of the spinning membrane separator 26. Certain procedures described herein employ only one of the ports 66 to produce a filtered plasma product, so it is within the scope of the present disclosure for the other outlet port 68 to be omitted or, if the other outlet port 68 is provided, for fluid flow therethrough to be prevented (which may include a line connected to the outlet port 68 being clamped or sealed or otherwise closed to fluid flow therethrough).

The illustrated spinning membrane separator 26 includes a generally cylindrical housing 70 mounted concentrically about a longitudinal vertical central axis. An internal member or rotor 72 is mounted concentrically with the central axis. The housing 70 and rotor 72 are relatively rotatable, as described above with respect to the spinning membrane separator drive unit 14. In a preferred embodiment, the housing 70 is stationary and the rotor 72 is a rotating spinner that is rotatable concentrically within the cylindrical housing 70. In such an embodiment, the housing 70 (or at least its upper and lower ends) are formed of non-magnetic material, while the rotor 72 includes an element (e.g., a metallic material) that interacts with a magnet of the spinning membrane separator drive unit 14 to rotate the rotor 72 within the housing 70, as described above.

The boundaries of the fluid flow path are generally defined by the gap 74 between the interior surface of the housing 70 and the exterior surface of the rotor 72, which is sometimes referred to as the shear gap. The width of the shear gap 74 may be of a uniform dimension along the axis, for example, where the axis of the housing 70 and rotor 72 are coincident. Alternatively, the width of the shear gap 74 also may vary along the axial direction, for example with the width of the gap 74 either increasing in the direction of flow to limit hemolysis or decreasing to increase shear in the gap 74. In one embodiment that may be particularly advantageous for "dead end" filtration of a plasma constituent (which will be described in greater detail herein), the gap width may be approximately 0.0668 cm at the upstream or inlet end of the gap 74 and approximately 0.0584 cm at the downstream end or terminus of the gap 74. The gap width could change linearly or stepwise or in some other manner as may be desired. In any event, the width dimension of the gap 74 is preferably selected so that at the desired relative rotational speed, Taylor-Couette flow, such as Taylor vortices, are created in the gap 74 and hemolysis is limited.

Separated plasma to be filtered is fed into the gap 74 by the inlet port 64 (FIG. 8), which directs the fluid into the fluid flow entrance region at or adjacent to the bottom end of the spinning membrane separator 26. The spinning membrane separator drive unit 14 causes relative rotation of the housing 70 and rotor 72, creating Taylor vortices within the gap 74. The outer surface of the rotor 72 and/or the inner surface of the housing 70 is at least partially (and more preferably, substantially or entirely) covered by a cylindrical, porous membrane 76 (shown in FIG. 9 as being mounted to the outer surface of the rotor 72). It should be, thus, understood that the term "spinning membrane separator" does not necessarily require that the membrane 76 is mounted to a component of the spinning membrane separator 26 that spins, but may also include a device in which the membrane 76 is mounted to a stationary component that includes another component that rotates with respect to the stationary membrane 76.

The membrane 76 has a nominal pore size and composition that may vary without departing from the scope of the present disclosure. However, in one embodiment, the membrane 76 is formed of a polycarbonate material and has a nominal pore size of approximately 0.8 microns, which serves to exclude any residual platelets, red blood cells, or white blood cells remaining in separated plasma following centrifugal separation, thus producing a filtered, virtually cell-free plasma product.

In an embodiment in which the rotor 72 spins within the housing 70 and the membrane 76 is mounted to the outer surface of the rotor 72, the outer surface of the rotor 72 may be shaped to define a series of spaced-apart circumferential grooves or ribs 78 separated by annular lands 80 (FIG. 9). The surface channels defined by the circumferential grooves 78 are interconnected by longitudinal grooves 82. At one or both ends of the rotor 72, these grooves 78 are in communication with a central orifice or manifold 84. Pumping fluid into and out of the spinning membrane separator 26 causes plasma to flow through the membrane 76 and grooves 78, while the cellular blood components remain within the gap 74 as fluid flows from the inlet port 64 at the bottom portion of the spinning membrane separator 26 toward the upper portion. Relative rotation of the rotor 72 and housing 70 causes a particular flow pattern within the gap 74 (described above) that enables filtration of the cellular blood components from the plasma without clogging the membrane 76.

At the upper portion of the spinning membrane separator 26, plasma exits the spinning membrane separator 26 via an outlet port 66 that is concentric with the rotational axis and in fluid communication with the central orifice 84 of the rotor 72 (FIG. 9), with the plasma flowing into a line associated with the outlet port 66. In one embodiment (which will be described herein), the plasma is "dead end" filtered by the spinning membrane separator 26, meaning that the cellular blood components separated from the plasma are prevented from exiting the gap 74 via an outlet port 68 defined in the upper end or portion of the housing 70 and oriented generally tangentially to the gap 74 (FIG. 8). The separated cellular blood components in the gap 74 may ultimately be discarded at the end of a procedure with the used spinning membrane separator 26 as a waste product. Alternatively, the separated cellular blood components in the gap 74 may be conveyed out of the gap 74 for collection or return to a blood source. Procedures according to both of these variations will be described in greater detail herein.

As described above, it may be advantageous to use differently sized spinning membrane separators 26 depending on the particular blood separation procedure being carried out. FIG. 8 shows a spinning membrane separator 26 having a rotor 72 with a spinner diameter D, a filtration length FL, and an overall length LOA. An exemplary smaller spinning membrane separator may have a spinner diameter D of approximately 1.1", a filtration length FL of approximately 3", and an overall length LOA of approximately 5.0". By comparison, an exemplary larger spinning membrane separator may have a spinner diameter D of approximately 1.65", a filtration length FL of approximately 5.52", and an overall length LOA of approximately 7.7". An exemplary smaller spinning membrane separator is described in greater detail in U.S. Pat. No. 5,194,145, while an exemplary larger spinning membrane separator is described in greater detail in U.S. Patent Application Publication No. 2015/0218517, which is incorporated herein by reference.

D. Centrifugal Separation Chamber

Figure 10:
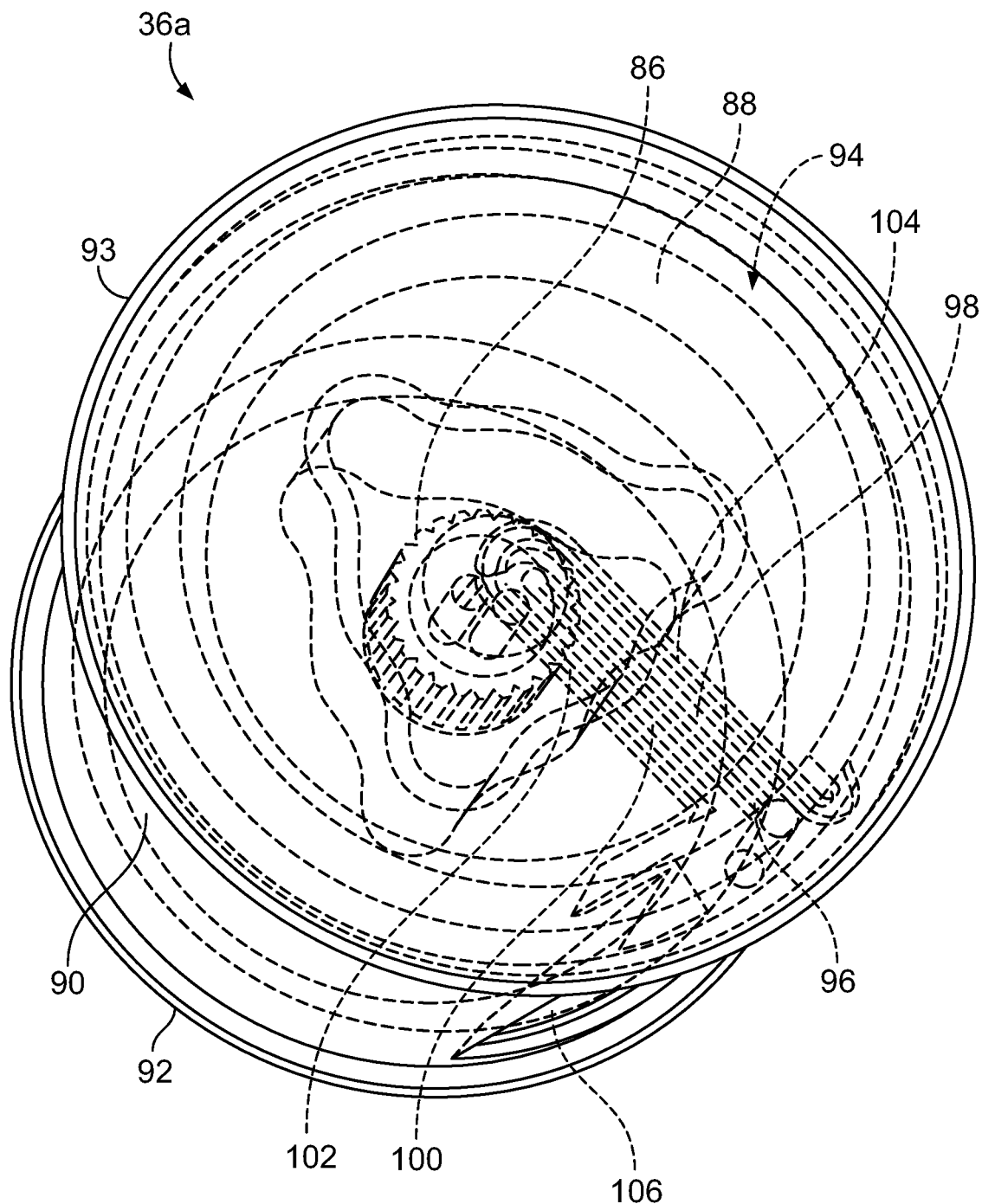
FIG. 10 is a perspective view of an exemplary centrifugal separation chamber of a fluid flow circuit.
Figure 11:
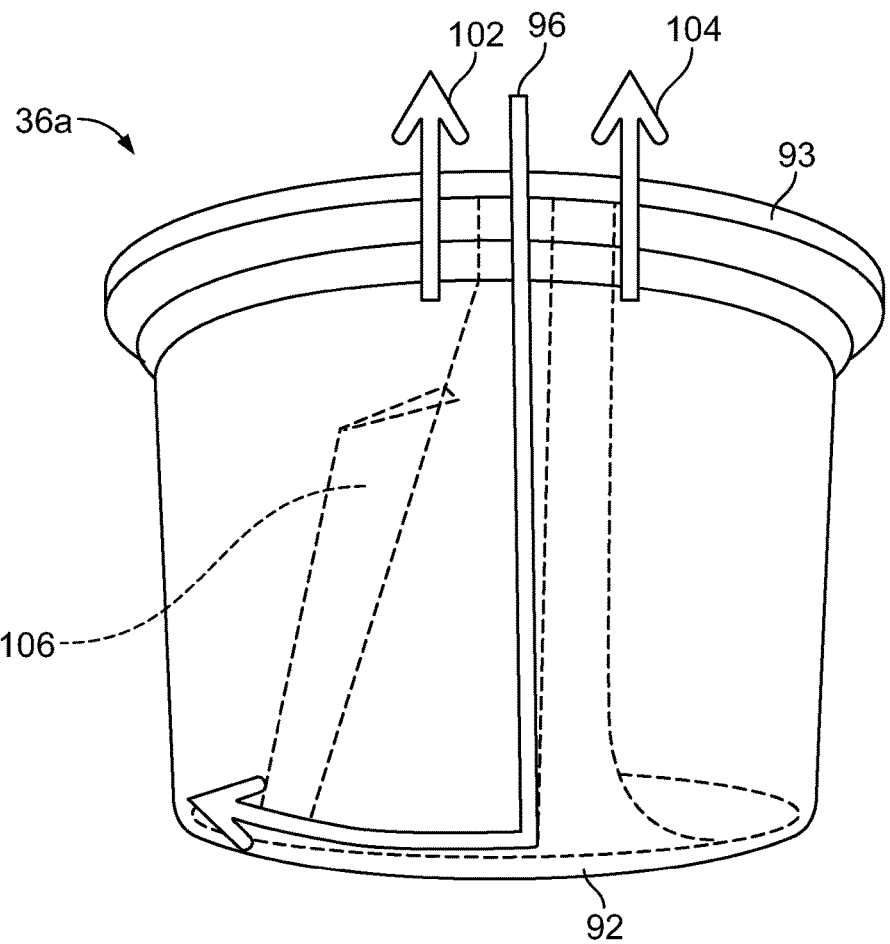
FIG. 11 is a front elevational view of the centrifugal separation chamber of FIG. 10.
Figure 12:
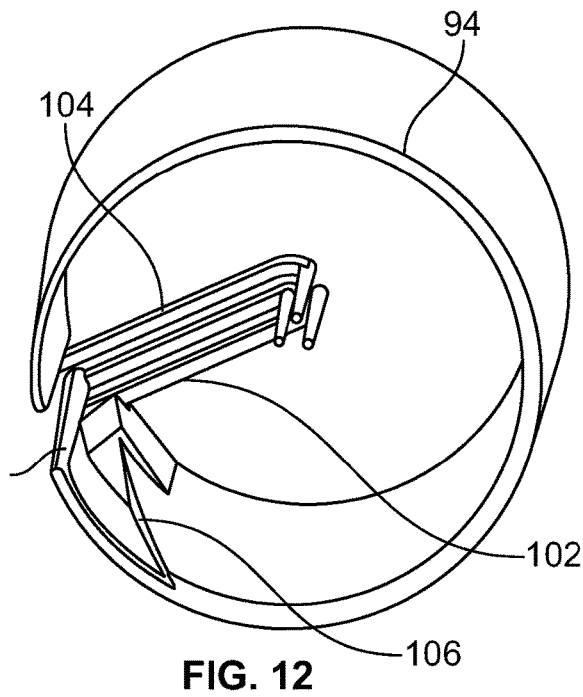
FIG. 12 is a bottom perspective view of the fluid flow path through the centrifugal separation chamber of FIG. 10.

A fluid flow circuit 12 is provided with a centrifugal separation chamber 36. An exemplary centrifugal separation chamber 36a is shown in FIGS. 10 and 11, while FIG. 12 illustrates the fluid flow path defined by the centrifugal separation chamber 36a. In the illustrated embodiment, the body of the centrifugal separation chamber 36a is preformed in a desired shape and configuration (e.g., by injection molding) from a rigid, biocompatible plastic material, such as a non-plasticized medical grade acrylonitrile-butadiene-styrene (ABS). All contours, ports, channels, and walls that affect the blood separation process are preformed in a single, injection molded operation. Alternatively, the centrifugal separation chamber 36a can be formed by separate molded parts, either by nesting cup-shaped subassemblies or two symmetric halves.

The underside of the centrifugal separation chamber 36a includes a shaped receptacle 86 that is suitable for receiving an end of the umbilicus 46 of the fluid flow circuit 12 (FIG. 3). A suitable receptacle 86 and the manner in which the umbilicus 46 may cooperate with the receptacle 86 to deliver fluid to and remove fluid from the centrifugal separation chamber 36a are described in greater detail in U.S. Pat. No. 8,075,468.

The illustrated centrifugal separation chamber 36a has radially spaced apart inner (low-g) and outer (high-g) side wall portions 88 and 90, a bottom or first end wall portion 92, and a cover or second end wall portion 93. The cover 93 comprises a simple flat part that can be easily welded or otherwise secured to the body of the centrifugal separation chamber 36a. Because all features that affect the separation process are incorporated into one injection molded component, any tolerance differences between the cover 93 and the body of the centrifugal separation chamber 36a will not affect the separation efficiencies of the centrifugal separation chamber 36a. The wall portions 88 and 90, the bottom 92, and the cover 93 together define an enclosed, generally annular channel 94 (FIG. 12).

The (whole blood) inlet 96 communicating with the channel 94 is defined between opposing interior radial walls 98 and 100. One of the interior walls 98 joins the outer (high-g) wall portion 90 and separates the upstream and downstream ends of the channel 94. The interior walls 98 and 100 define the inlet passageway 96 of the centrifugal separation chamber 36a which, in one flow configuration, allows fluid to flow from the umbilicus 46 to the upstream end of the channel 94.

The illustrated centrifugal separation chamber 36a further includes first and second outlets 102 and 104, respectively, which may be defined by opposing surfaces of interior radial walls. Both the first and second outlets 102 and 104 extend radially inward from the channel 94. The first (plasma) outlet 102 extends radially inward from an opening which, in the illustrated embodiment, is located at the inner side wall portion 88, while the second (red blood cell) outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

Figure 13:
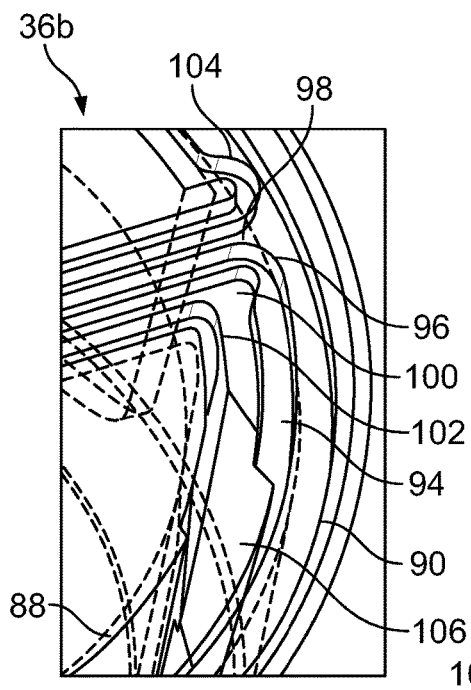
FIG. 13 is a perspective view of another embodiment of a centrifugal separation chamber of a fluid flow circuit.
Figure 14:
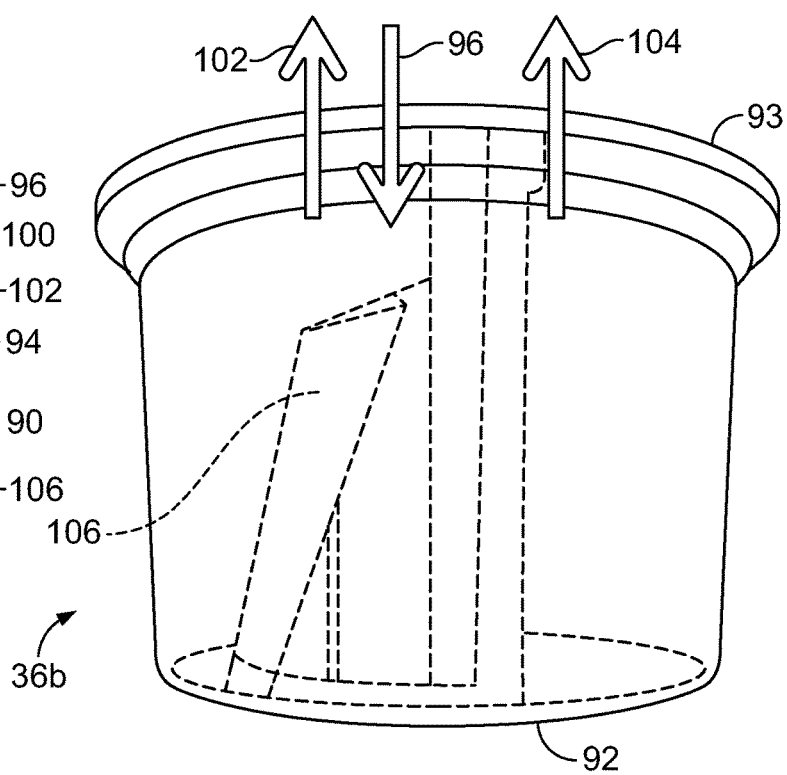
FIG. 14 is a front elevational view of the centrifugal separation chamber of FIG. 13.
Figure 15:
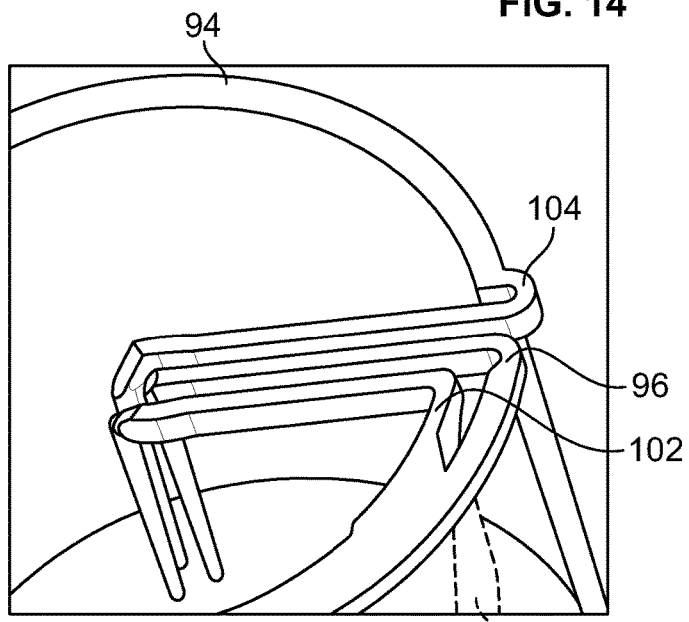
FIG. 15 is a top perspective view of the fluid flow path through the centrifugal separation chamber of FIG. 13.

It should be understood that the centrifugal separation chamber 36a illustrated in FIG. 10 is merely exemplary and that the centrifugal separation chamber 36 may be differently configured without departing from the scope of the present disclosure. For example, FIGS. 13 and 14 show an alternative embodiment of a centrifugal separation chamber 36b, while FIG. 15 illustrates the fluid flow path defined by the centrifugal separation chamber 36b. The centrifugal separation chamber 36b is similar to the centrifugal separation chamber 36a except for the location at which the inlet 96 opens into the channel 94. In the centrifugal separation chamber 36a of FIG. 10, the inlet 96 opens into the channel 94 adjacent to the first end wall portion 92 (while the outlets 102 and 104 open into the channel 94 adjacent to the second end wall portion 93), as best shown in FIGS. 11 and 12. In contrast, the inlet 96 of the centrifugal separation chamber 36b of FIG. 13 opens into the channel 94 adjacent to the second end wall portion 93 (along with the outlets 102 and 104), as best shown in FIGS. 14 and 15. The location at which the inlet 96 opens into the channel 94 may affect the separation of fluid within the channel 94, so the centrifugal separation chamber 36a of FIG. 10 may be preferable for certain procedures or for use in combination with certain blood separation devices, while the centrifugal separation chamber 36b of FIG. 13 may be preferable for other procedures or for use in combination with other blood separation devices.

Figure 16:
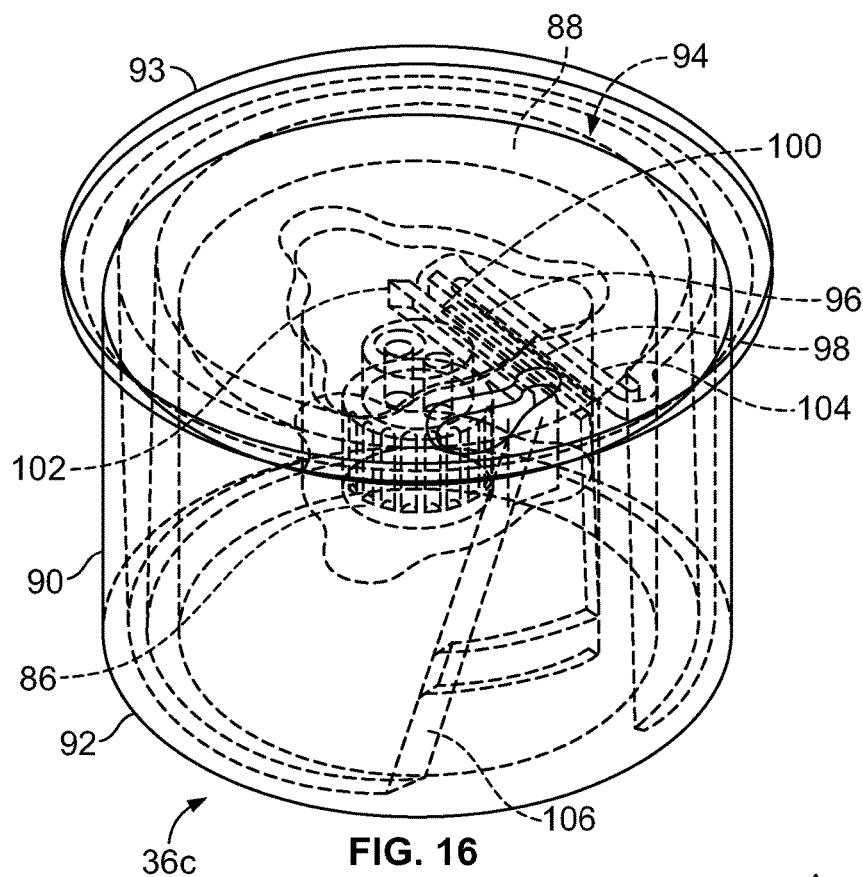
FIG. 16 is a perspective view of a third embodiment of a centrifugal separation chamber of a fluid flow circuit.
Figure 17:
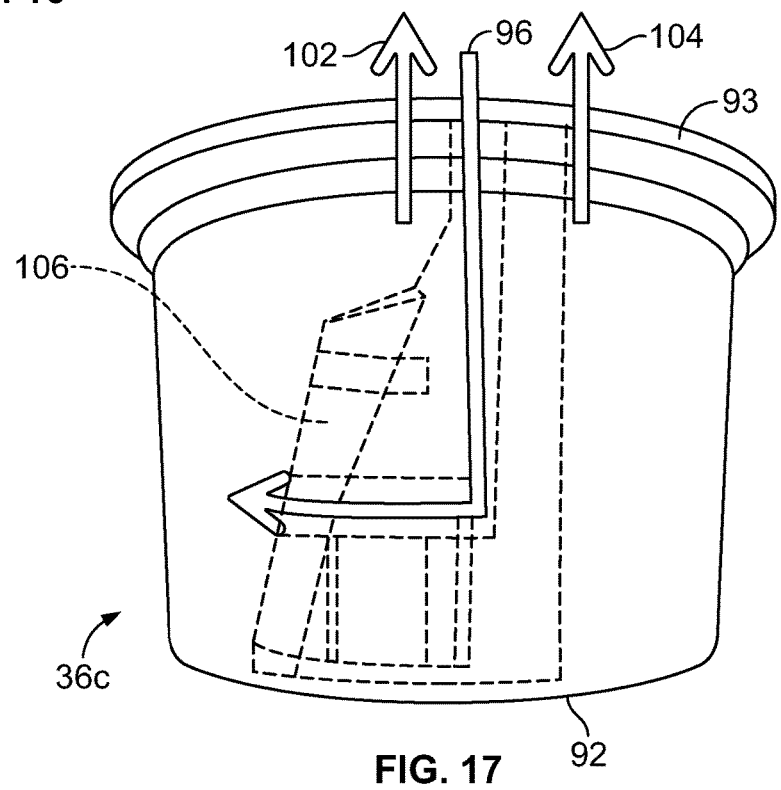
FIG. 17 is a front elevational view of the centrifugal separation chamber of FIG. 16.

FIGS. 16 and 17 show another exemplary embodiment of a centrifugal separation chamber 36c suitable for incorporation into a fluid flow circuit 12. The centrifugal separation chamber 36c is similar to the centrifugal separation chambers 36a and 36b of FIGS. 10 and 13 except for the location at which the inlet 96 opens into the channel 94. In contrast to the inlets 96 of the centrifugal separation chambers 36a and 36b of FIGS. 10 and 13, the inlet 96 of the centrifugal separation chamber 36c of FIG. 16 opens into the channel 94 at an intermediate axial location that is spaced from the first and second end wall portion 92 and 93 (while the outlets 102 and 104 open into the channel adjacent to the second end wall portion 93), as best shown in FIG. 17. The inlet 96 may open into the channel 94 at a location that is closer to the first end wall portion 92 than to the second end wall portion 93, at a location that is closer to the second end wall portion 93 than to the first end wall portion 92, or at a location that is equally spaced between the first and second end wall portions 92 and 93. The axial location at which the inlet 96 opens into the channel 94 may affect the separation of fluid within the channel 94, so the preferred location at which the inlet 96 opens into the channel 94 (which may also depend upon the nature of the blood separation device paired with the centrifugal separation chamber 36c) may be experimentally determined.

1. Centrifugal Separation and Interface Detection Principles

Blood flowed into the channel 94 separates into an optically dense layer RBC and a less optically dense layer PLS (FIGS. 18-20) as the centrifugal separation chamber 36 is rotated about the rotational axis 38. The optically dense layer RBC forms as larger and/or heavier blood particles move under the influence of centrifugal force toward the outer (high-g) wall portion 90. The optically dense layer RBC will typically include red blood cells (and, hence, may be referred to herein as the "RBC layer") but, depending on the speed at which the centrifugal separation chamber 36 is rotated, other cellular components (e.g., larger white blood cells) may also be present in the optically dense layer RBC.

The less optically dense layer PLS typically includes a plasma constituent, such as platelet-rich plasma or platelet-poor plasma (and, hence, will be referred to herein as the "PLS layer"). Depending on the speed at which the centrifugal separation chamber 36 is rotated and the length of time that the blood is resident therein, other components (e.g., smaller white blood cells and anticoagulant) may also be present in the less optically dense layer PLS.

In one embodiment, blood introduced into the channel 94 via the inlet 96 will travel in a generally clockwise direction (in the orientation of FIG. 10) as the optically dense layer RBC separates from the less optically dense layer PLS. The optically dense layer RBC continues moving in the clockwise direction as it travels the length of the channel 94 along the outer side wall portion 90, from the upstream end to the downstream end, where it exits the channel 94 via the second outlet 104. The less optically dense layer PLS separated from the optically dense layer RBC reverses direction, moving counterclockwise along the inner side wall portion 88 to the first outlet 102, adjacent to the inlet 96. The inner side wall portion 88 may be tapered inward as it approaches the second outlet 104 to force the plasma liberated at or adjacent to the downstream end of the channel 94 to drag the interface back towards the upstream end of the channel 94, where the lower surface hematocrit will re-suspend any platelets settled on the interface.

Figure 18:
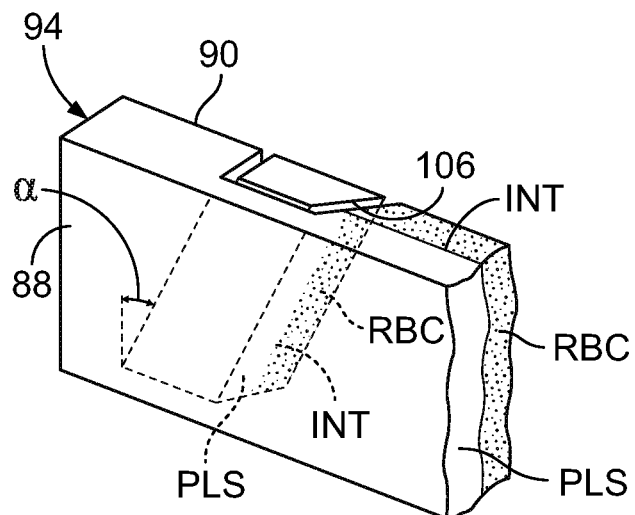
FIG. 18 is an enlarged perspective view of a portion of a channel of any of the centrifugal separation chambers of FIGS. 10-17, with an interface between separated blood components being positioned at a (typically) desired location on a ramp defined within the channel.
Figure 19:
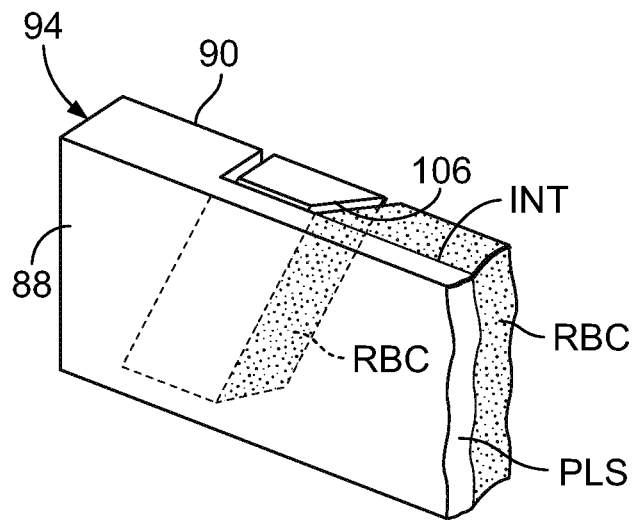
FIG. 19 is an enlarged perspective view of the channel and ramp of FIG. 18, with the interface being at a (typically) undesired high location on the ramp.
Figure 20:
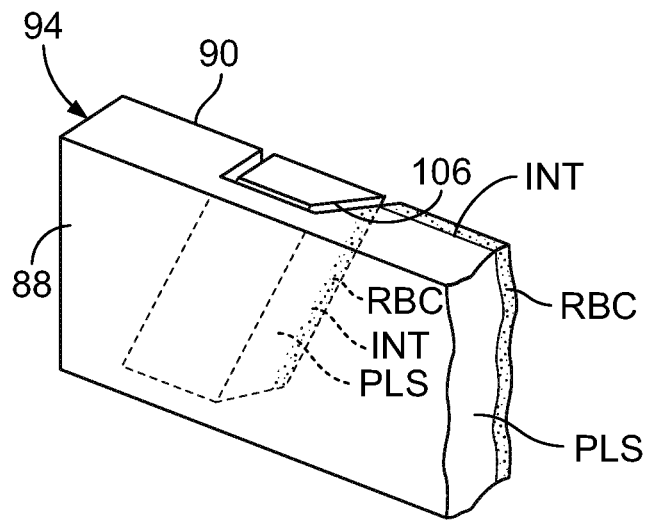
FIG. 20 is an enlarged perspective view of the channel and ramp of FIG. 18, with the interface being at a (typically) undesired low location on the ramp.

As described above, the transition between the optically dense layer RBC and the less optically dense layer PLS may be referred to as the interface INT. The location of the interface INT within the channel 94 of the centrifugal separation chamber 36 can dynamically shift during blood processing, as FIGS. 18-20 show. If the location of the interface INT is too high (that is, if it is too close to the inner side wall portion 88 and the first outlet 102, as in FIG. 19), red blood cells can flow into the first outlet 102, potentially adversely affecting the quality of the low density components (platelet-rich plasma or platelet-poor plasma). On the other hand, if the location of the interface INT is too low (that is, if it resides too far away from the inner wall portion 88, as FIG. 20 shows), the collection efficiency of the system may be impaired. The ideal or target interface INT may be experimentally determined, which may vary depending on any of a number of factors (e.g., the configuration of the centrifugal separation chamber 36, the rate at which the centrifugal separation chamber 36 is rotated about the rotational axis 38, etc.).

As described above, the blood separation device 10 may include an interface monitoring system and a controller 18 with an interface control module to monitor and, as necessary, correct the position of the interface INT. In one embodiment, the centrifugal separation chamber 36 is formed with a ramp 106 extending from the high-g wall portion 90 at an angle α across at least a portion of the channel 94 (FIGS. 10 and 18-20). The angle α, measured with respect to the rotational axis 38 is about 25° in one embodiment. FIGS. 18-20 show the orientation of the ramp 106 when viewed from the low-g side wall portion 88 of the centrifugal separation chamber 36. Although it describes a flexible separation chamber, the general structure and function of the ramp 106 may be better understood with reference to U.S. Pat. No. 5,632,893, which is incorporated herein by reference. The ramp 106 may be positioned at any of a number of locations between the upstream and downstream ends of the channel 94, but in one embodiment, the ramp 106 may be positioned generally adjacent to the first outlet 102, in the path of fluid and/or a fluid component moving from the inlet 96 to the first outlet 102.

The ramp 106 makes the interface INT between the optically dense layer RBC and the less optically dense layer PLS more discernible for detection, displaying the optically dense layer RBC, less optically dense layer PLS, and interface INT for viewing through a light-transmissive portion of the centrifugal separation chamber 36. To that end, the ramp 106 and at least the portion of the centrifugal separation chamber 36 angularly aligned with the ramp 106 may be formed of a light-transmissive material, although it may be advantageous for the entire centrifugal separation chamber 36 to be formed of the same light-transmissive material.

In the illustrated embodiment, the light source 50 of the interface monitoring system is secured to a fixture or wall of the centrifuge compartment 32 and oriented to emit a light that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 88, as shown in FIGS. 5 and 6. The reflector may be a separate piece that is secured to the inner side wall portion 88 (e.g., by being bonded thereto) or may be integrally formed with the body of the centrifugal separation chamber 36.

Figures 21, 22:
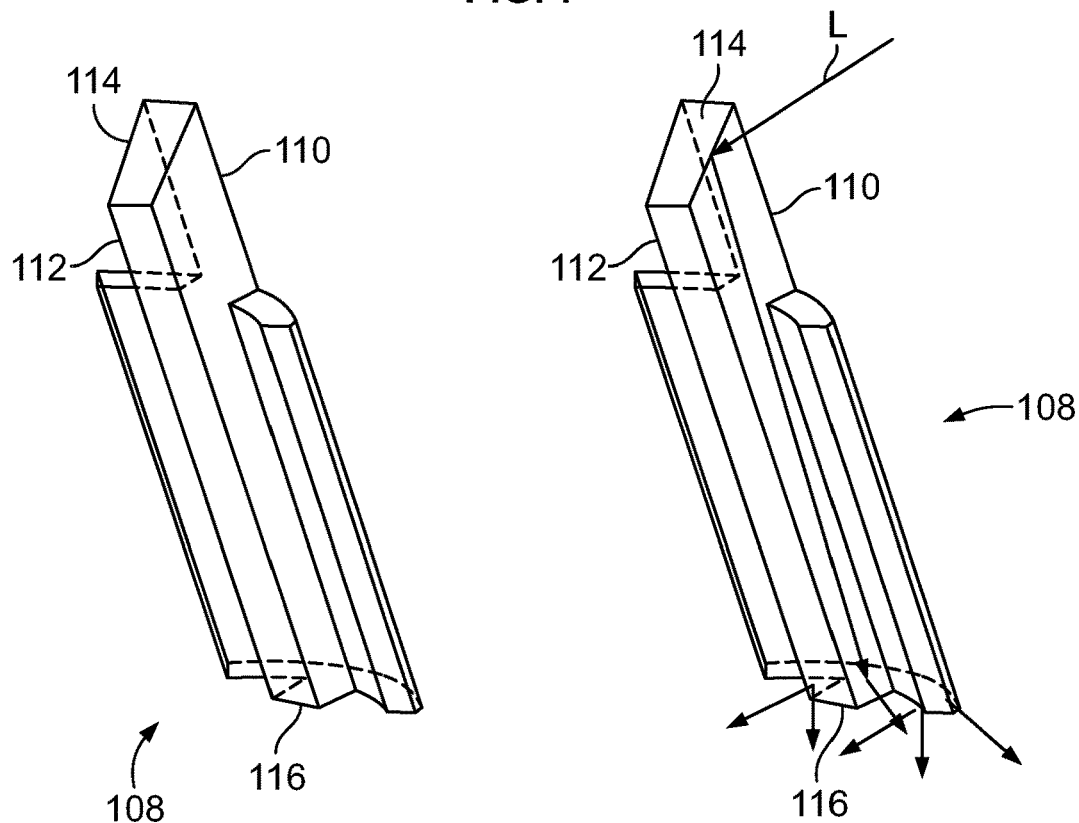
FIG. 21 is a perspective view of a prismatic reflector used in combination with any of the centrifugal separation chambers of FIGS. 10-17.
FIG. 22 is a perspective view of the prismatic reflector of FIG. 21, showing light being transmitted therethrough.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 108 (FIGS. 7, 21, and 22), which is formed of a light-transmissive material (e.g., a clear plastic material) and has inner and outer walls 110 and 112 and first and second end walls 114 and 116 (FIG. 21). The inner wall 110 is positioned against the inner side wall portion 88 of the centrifugal separation chamber 36 and is oriented substantially perpendicular to the initial path of the light L from the light source 50. This allows light L from the light source 50 to enter into the prismatic reflector 108 via the inner wall 110 while continuing along its initial path. The light L continues through the prismatic reflector 108 along its initial path until it encounters the first end wall 114. The first end wall 114 is oriented at an angle (e.g., an approximately 45° angle) with respect to the first surface 110 and the second end wall 116, causing the light to be redirected within the prismatic reflector 108, rather than exiting the prismatic reflector 108 via the first end wall 114.

The first end wall 114 directs the light L at an angle to its initial path (which may be an approximately 90° angle, directing it from a path toward the rotational axis 38 to a path that is generally parallel to the rotational axis 38) toward the second end wall 116 (FIG. 22). The first end wall 114 and the inner and outer walls 110 and 112 of the prismatic reflector 108 may be configured to transmit the redirected light L from the first end wall 114 to the second end wall 116 by total internal reflection. The second end wall 116 is oriented substantially perpendicular to the redirected path of the light L through the prismatic reflector 108, such that the light L will exit the prismatic reflector 108 via the second end wall 116, continuing along its redirected path. In one embodiment, the second end wall 116 is roughened or textured or otherwise treated or conditioned to diffuse the light L as it exits the prismatic reflector 108, which may better ensure that the light L reaches the light detector 52 (FIG. 7).

Figure 23:
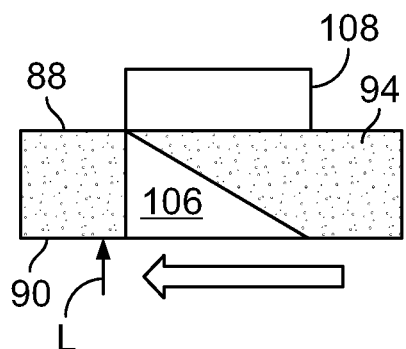
FIGS. 23-26 are diagrammatic views of the ramp and prismatic reflector of the centrifugal separation chamber passing through the path of light from the light source during a calibration phase.
Figure 27:
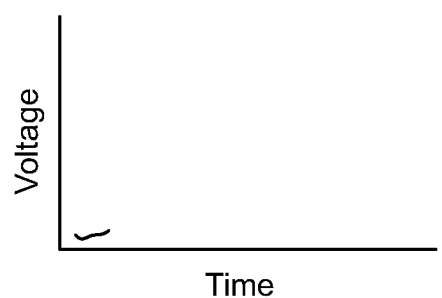
FIGS. 27-30 are diagrammatic views of the voltage output or signal transmitted by the light detector during the conditions shown in FIGS. 23-26, respectively.
Figure 24:
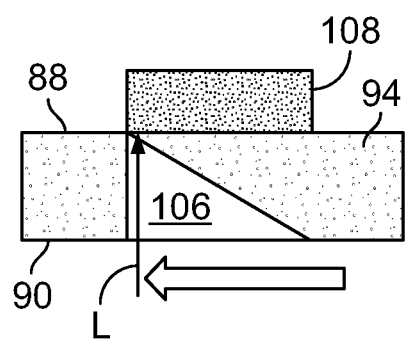

The prismatic reflector 108 may be angularly aligned with the ramp 106, such that the light L from the light source 50 will only enter into the prismatic reflector 108 when the ramp 106 has been rotated into the path of the light L. At all other times (when the ramp 106 is not in the path of the light L), the light L will not reach the prismatic reflector 108 and, thus, will not reach the light detector 52. This is illustrated in FIGS. 23-26, which show the ramp 106 and prismatic reflector 108 as the centrifugal separation chamber 36 is rotated about the rotational axis 38 (while the light source 50 remains in a fixed location). In FIG. 23, the ramp 106 and prismatic reflector 108 have not yet been rotated into the initial path of the light L from the light source 50. At this time, no light is transmitted to the light detector 52, such that the output voltage of the light detector 52 (i.e., the signal transmitted from the light detector 52 to the controller 18) is in a low- or zero-state (FIG. 27).

Figure 28:
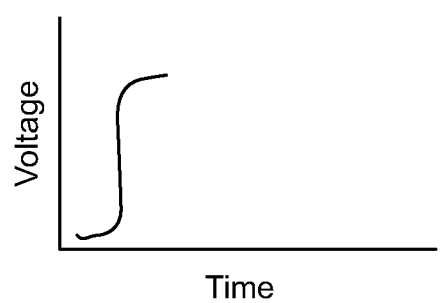

Upon the ramp 106 first being rotated into the initial path of the light L from the light source 50 (FIG. 24), the light L will begin to reach the prismatic reflector 108, which directs the light L to the light detector 52. This causes the voltage output of the light detector 52 (i.e., the signal transmitted from the light detector 52 to the controller 18) to increase to a non-zero value or state, as shown in FIG. 28.

Figure 25:
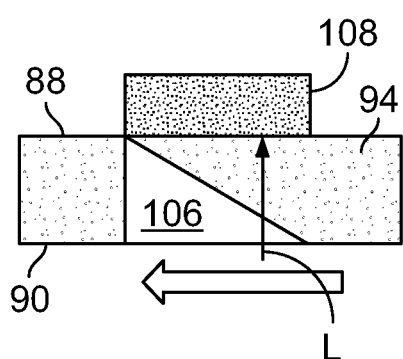
Figure 29:
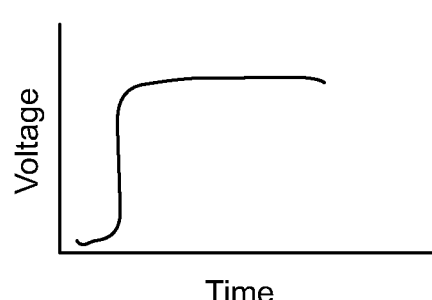
Figure 26:
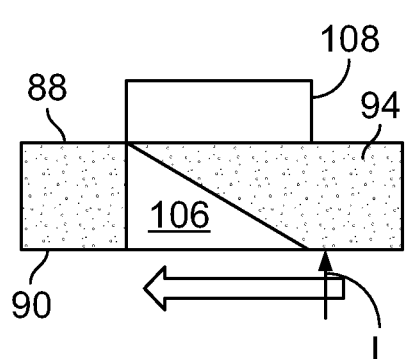

During a calibration phase, the channel 94 is filled with a fluid that will transmit the light L rather than absorbing or reflecting the light or otherwise preventing the light L from reaching the prismatic reflector 108, such that the voltage output of the light detector 52 will remain generally constant as the ramp 106 and prismatic reflector 108 are rotated through the initial path of the light L from the light source 50 (FIGS. 25 and 29). Such a calibration phase may coincide with a priming phase during which saline is pumped through the fluid flow circuit 12 to prime the fluid flow circuit 12 or may comprise a separate phase. A calibration phase may be useful in ensuring the proper operation of the light source 50 and the light detector 52, standardizing the readings taken during a separation procedure in case of any irregularities or imperfections of the centrifugal separation chamber 36, and establishing a baseline value for the signal transmitted from the light detector 52 to the controller 18 when the ramp 106 and prismatic reflector 108 are aligned with the light source 50. As will be described in greater detail, the voltage output of the light detector 52 will typically not remain constant as the ramp 106 and prismatic reflector 108 are rotated through the initial path of the light L from the light source 50 because the different fluid layers displayed on the ramp 106 will allow different amounts of light L to reach the prismatic reflector 108.

Figure 30:
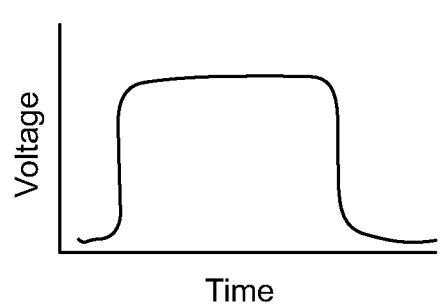
Figure 31:
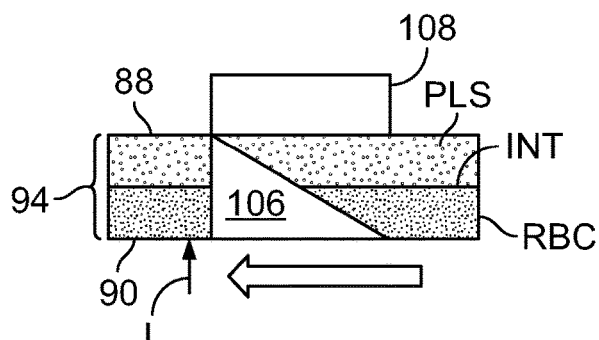
FIGS. 31-34 are diagrammatic views of the ramp and prismatic reflector passing through the path of light from the light source during a separation procedure.

The ramp 106 and prismatic reflector 108 are eventually rotated out of alignment with the light source 50 (FIG. 26), at which time no light L will reach the prismatic reflector 108 and the voltage output of the light detector 52 will return to its low- or zero-state (FIG. 30).

It may be advantageous for the light L to have a relatively small diameter for improved resolution of the signal that is generated by the light detector 52.

2. Exemplary Interface Detection and Correction Procedure

During separation of blood within the channel 94, the light L from the light source 50 travels through a light-transmissive portion of the outer side wall portion 90 and the ramp 106 to intersect the separated blood components thereon when the ramp 106 has been rotated into the initial path of the light L. After passing through the ramp 106, the light continues through the channel 94 and the fluids in the channel 94. At least a portion of the light L (i.e., the portion not absorbed or reflected by the fluids) exits the channel 94 by striking and entering a light-transmissive portion of the inner side wall portion 88. The light L passes through the inner side wall portion 88 and enters the prismatic reflector 108, which redirects the light L from its initial path to the light detector 50, as described above. Thus, it will be seen that the light L reaches the light detector 52 after intersecting and traveling through the separated blood components in the channel 94 only once, in contrast to known systems in which light from a light source travels through a ramp and a fluid-filled channel before being reflected back through the channel to reach a light detector. Requiring the light L to traverse the fluid-filled channel 94 only once before reaching the light detector 52 instead of twice may be advantageous in that it tends to increase the intensity of the light L that reaches the light detector 52, which may improve monitoring and correction of the interface location.

The light detector 52 generates a signal that is transmitted to the interface control module of the controller 18, which can determine the location of the interface INT on the ramp 106. In one embodiment, the location of the interface INT is associated with a change in the amount of light L that is transmitted through the less optically dense layer PLS and the optically dense layer RBC. For example, the light source 50 may be configured to emit a light L that is more readily transmitted by platelet-rich plasma or platelet-poor plasma than by red blood cells, such as red visible light (from a laser or a differently configured light source 50), which is substantially absorbed by red blood cells. The less optically dense layer PLS and the optically dense layer RBC each occupy a certain portion of the ramp 106, with the light detector 52 receiving different amounts of light L depending on whether the light L travels through the less optically dense layer PLS on the ramp 106 or the optically dense layer RBC on the ramp 106. The percentage of the ramp 106 occupied by each layer is related to the location of the interface INT in the channel 94. Thus, by measuring the amount of time that the voltage output or signal from the light detector 52 is relatively high (corresponding to the time during which the light L is passing through only the less optically dense layer PLS on the ramp 106), the controller 18 may determine the location of the interface INT and take steps to correct the location of the interface INT, if necessary.

Figure 32:
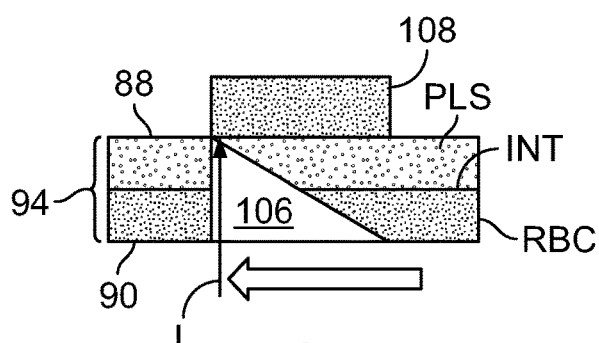
Figure 33:
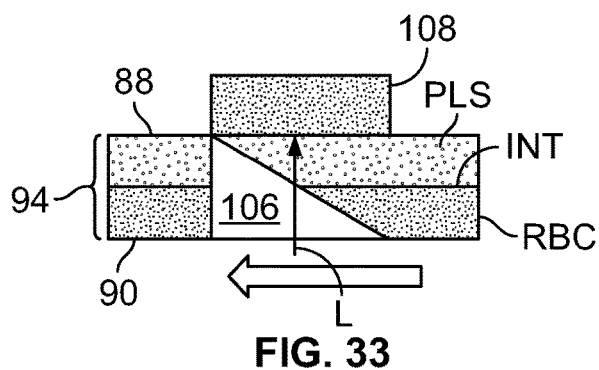
Figure 34:
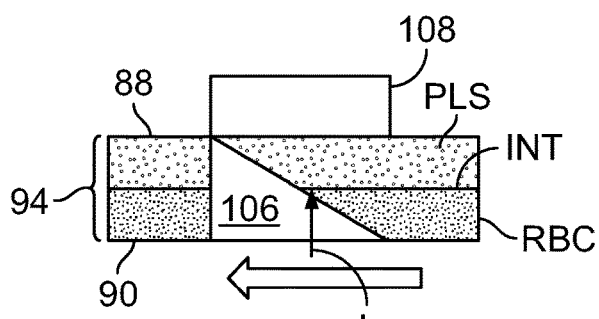

FIGS. 31-34 show a portion of the ramp 106 being rotated into and through the initial path of the light L from the light source 50. Four specific events are shown: just before the ramp 106 is rotated into the path of the light L (FIG. 31), the ramp 106 first being rotated into the path of the light L (FIG. 32), just before the interface INT displayed on the ramp 106 is rotated into the path of the light L (FIG. 33), and just after the interface INT is rotated into the path of the light L (FIG. 34). FIGS. 35-38 respectively illustrate the voltage output of the light detector 52 (corresponding to the signal that it transmits to the controller 18) during each of these events.

Figure 35:
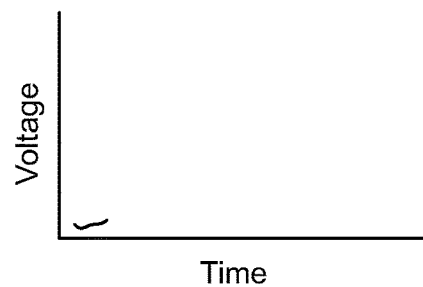
FIGS. 35-38 are diagrammatic views of the voltage output or signal transmitted by the light detector during the conditions shown in FIGS. 31-34, respectively.

As described above, the light detector 52 will receive no light L from the light source 50 when the prismatic reflector 108 is out of alignment with the initial path of the light L from the light source 50, as shown in FIG. 29. FIG. 35 shows that the output voltage of the light detector 52 (i.e., the signal transmitted from the light detector 52) to the controller 18) at this time is in a low- or zero-state.

When the ramp 106 is first rotated into the path of light L from the light source 50 (FIG. 32), the light detector 52 may begin receiving light L. The amount of light L received by the light detector 52 depends upon the fluid on the ramp 106 encountered by the light L (i.e., the fluid in the channel 94 between the ramp 106 and the inner side wall portion 88 that the light L must traverse before being directed to the light detector 52). As described above, the less optically dense layer PLS occupies a certain percentage of the channel 94 adjacent to the inner side wall portion 88, while the optically dense layer RBC occupies a certain percentage of the channel 94 adjacent to the outer side wall portion 90 (with the interface INT positioned at the transition between the two separated blood component layers). The illustrated ramp 106 is closest to the inner side wall portion 88 at its left end (in the orientation of FIGS. 31-34), while being farther spaced from the inner side wall portion 88 at its right end. At and adjacent to its left end, the ramp 106 will display only the fluid positioned closest to the inner side wall portion 88 (i.e., the less optically dense layer PLS), while the ramp 106 will display only the fluid positioned closest to the outer side wall portion 90 (i.e., the optically dense layer RBC) at and adjacent to its right end, as shown in FIGS. 31-34. At some point between its ends, the angled ramp 106 will be at a radial position where it will display the transition between the less optically dense layer PLS and the optically dense layer RBC (i.e., the interface INT). Hence, the location of the interface INT on the ramp 106 is dependent upon the percentage of the width of the ramp 106 that displays the less optically dense layer PLS (which is indicative of the percentage of the channel 94 occupied by the less optically dense layer PLS) and the percentage of the width of the ramp 106 that displays the optically dense layer RBC (which is indicative of the percentage of the channel 94 occupied by the optically dense layer RBC). It should be understood that the percentage of the ramp 106 occupied by the less optically dense layer PLS and by the optically dense layer RBC is not necessarily equal to the percentage of the channel 94 occupied by the less optically dense layer PLS and by the optically dense layer RBC, but that the percentage of the ramp 106 occupied by a separated blood component layer may be merely indicative of the percentage of the channel 94 occupied by that separated blood component layer.

Figure 36:
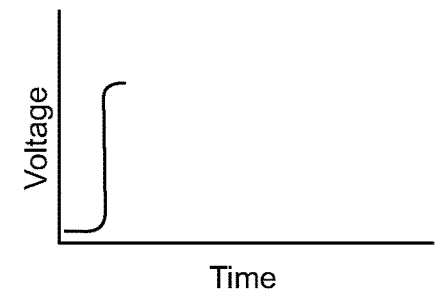

In such an embodiment, as the ramp 106 is rotated into the path of the light L from the light source 50, the light L will first encounter the portion of the ramp 106 that is positioned closest to the inner side wall portion 88 (i.e., the section of the ramp 106 that most restricts the channel 94), as shown in FIG. 32. As described above, the less optically dense layer PLS will be positioned adjacent to the inner side wall portion 88 as it separates from the optically dense layer RBC, such that the fluid displayed on this radially innermost section of the ramp 106 (i.e., the fluid present in the channel 94 between the ramp 106 and the inner side wall portion 88) will be the less optically dense layer PLS. The light is substantially transmitted through the less optically dense layer PLS to the inner side wall portion 88, and through the light-transmissive inner side wall portion 88 to the prismatic reflector 108, which redirects the light L to the light detector 52. This causes the voltage output of the light detector 52 (i.e., the signal transmitted from the light detector 52 to the controller 18) to increase to a non-zero value or state, as shown in FIG. 36. Depending on the nature of the light L, the amount of light L received by the light detector 52 (and, hence, the magnitude of the voltage output) after the light L has passed through the less optically dense layer PLS may be greater than, less than, or equal to the amount of light L received by the light detector 52 after passing through saline during the calibration phase described above.

Figure 37:
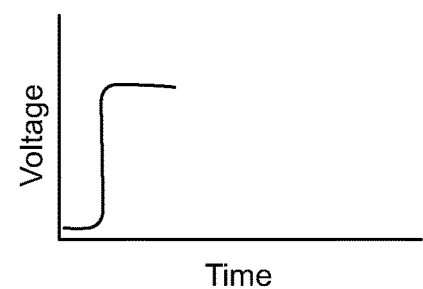

Further rotation of the ramp 106 through the path of light L from the light source 50 exposes the light L to portions of the ramp 106 that are increasingly spaced from the inner side wall portion 88 (i.e., the light L travels through portions of the channel 94 that are less restricted by the ramp 106 as the ramp 106 is rotated through the path of the light L). Up until the time that the interface INT on the ramp 106 is rotated into the path of the light L (as shown in FIG. 33), the only fluid in the channel 94 that the light L will have passed through will be the less optically dense layer PLS, such that a generally uniform level of light reaches the light detector 52 between the conditions shown in FIGS. 32 and 33. Accordingly, the voltage output of the light detector 52 will be generally uniform (at an elevated level) the whole time that the ramp 106 passes through the path of the light L before being exposed to the interface INT, as shown in FIG. 37. The controller 18 may be programmed and/or configured to consider a signal that deviates from a maximum signal level (e.g., a 10% decrease) to be part of the elevated signal for purposes of calculating the pulse width of the signal. The controller 18 will treat a greater deviation (i.e., a greater decrease in the magnitude of the signal) as the end of the elevated signal for purposes of calculating the pulse width of the signal.

Just after the interface INT has been rotated into the path of light L from the light source 50, the light L will begin to encounter the optically dense layer RBC in the channel 94, as shown in FIG. 34). As described above, the optically dense layer RBC will be positioned adjacent to the outer side wall portion 90 as it separates from the less optically dense layer PLS, such that the optically dense layer RBC will not be displayed on the ramp 106 until the ramp 106 is spaced a greater distance away from the inner side wall portion 88 (i.e., toward the right end of the ramp 106 in the orientation of FIGS. 31-34). Less light L is transmitted through the optically dense layer RBC than through the less optically dense layer PLS (which may include all or substantially all of the light L being absorbed by the optically dense layer RBC), such that the amount of light L that reaches the light detector 52 will decrease compared to the amount of light L that reaches the light detector 52 while traveling through only the less optically dense layer PLS in the channel 94 (FIGS. 32 and 33).

Figure 38:
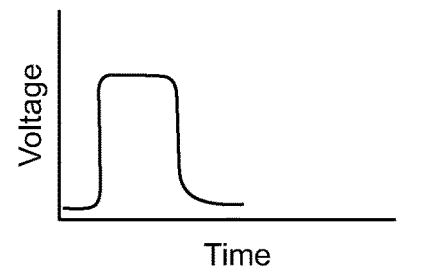

When receiving less light L, the voltage output or signal from the light detector 52 will decrease to a lower level than when the light L was passing through only the less optically dense layer PLS in the channel 94, as shown in FIG. 38. When the light L encounters the optically dense layer RBC in the channel 94, the light detector 52 may be generating a signal or voltage output that is approximately equal to its zero-state (as in FIG. 35, when the light detector 52 is receiving no light L) or a signal or voltage output that is some degree less than the magnitude of the signal or voltage output generated while the light L encounters only the less optically dense layer PLS in the channel 94. The controller 18 may be programmed and/or configured to recognize this lower level signal as representing the presence of the optically dense layer RBC on the ramp 106 (and in the portion of the channel 94 being traversed by the light L) and treat this lower level signal as the end point of the elevated signal generated by the light detector 52 while light L passes through only the less optically dense layer PLS in the channel 94.

Figure 39:
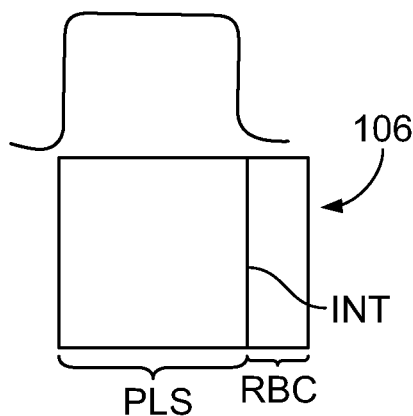
FIGS. 39 and 40 are diagrammatic views of separated blood components on the ramp and the pulse widths of a signal generated by the light detector for each condition.
Figure 40:
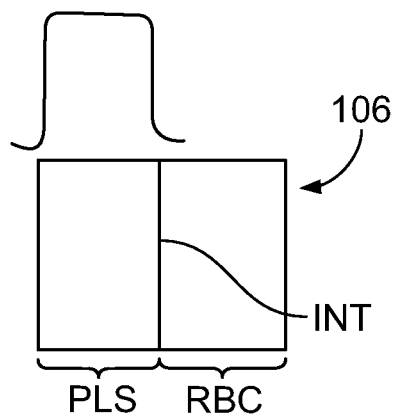

Thus, the pulse width of the elevated signal from the light detector 52 to the controller 18 (i.e., the time during which light L is traversing only the less optically dense layer PLS in the channel 94) is determined by the percentages of the ramp 106 that are occupied by the less optically dense layer PLS and the optically dense layer RBC. Accordingly, a greater pulse width of the signal from the light detector 52 to the controller 18 is associated with the less optically dense layer PLS occupying a larger portion of the ramp 106 (as shown in FIG. 39 from the point of view of the light source 50, which may correspond to the condition shown in FIG. 19) and will be indicative of a thinner optically dense layer RBC on the ramp 106 (and in the channel 94). Conversely, a signal from the light detector 52 to the controller 18 having a narrower pulse width is associated with the less optically dense layer PLS occupying a smaller portion of the ramp 106 (as shown in FIG. 40) and will be indicative of a thicker optically dense layer RBC on the ramp 106 (and in the channel 94).

Figure 41:
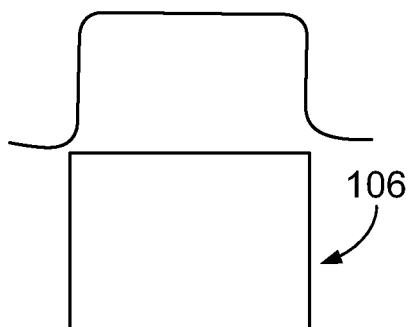
FIG. 41 is a diagrammatic view of saline on the ramp and the pulse width of a signal generated by the light detector for such a condition.

The controller 18 may compare the pulse width of the signal to the pulse width generated during the calibration phase (described above and shown in FIG. 41), which corresponds to the pulse width when light L is transmitted to the light detector 52 over the entire width of the ramp 106. The pulse width of the signal generated by the light detector 52 during the calibration phase may be referred to as the saline calibration signal. Comparing these two pulse widths will indicate the percentage of the ramp 106 that is occupied by the less optically dense layer PLS and by the optically dense layer RBC, which information the controller 18 may use to determine the location of the interface INT within the channel 94. In particular, the interface position may be calculated as follows:

Interface position (%)=((saline calibration pulse width−current plasma pulse width)/saline calibration pulse width)*100    [Equation 1]

It will be seen that Equation 1 effectively calculates the percentage of the ramp 106 that is occupied by the optically dense layer RBC, as the difference between the two pulse widths corresponds to the length of time that the ramp 106 is rotated through the path of the light L without the light detector 52 received an elevated level of light L (i.e., the amount of time that the ramp 106 is rotated through the path of the light L while the optically dense layer RBC is present on the ramp 106).

Figure 42:
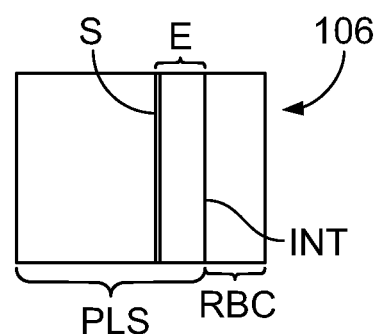
FIG. 42 is a diagrammatic view of the position of an interface between separated blood components on the ramp compared to a target interface position.

When the location of the interface INT on the ramp 106 has been determined, the interface control module compares the actual interface location with a desired interface location, which may be referred to as the setpoint S. The difference between the setpoint S and the calculated interface position may be referred to as the error signal E, which is shown in FIG. 42. It should be understood that so expressing the error signal E in terms of a targeted red blood cell percentage value (i.e., the percentage of the ramp 106 that is actually occupied by the optically dense layer RBC vs. the percentage of the ramp 106 which should be occupied by the optically dense layer RBC) is merely exemplary, and that the error signal E may be expressed or calculated in any of a number of other ways.

When the control value is expressed in terms of a targeted red blood cell percentage value, a negative error signal E indicates that the optically dense layer RBC on the ramp 106 is too large (as FIG. 19 shows). The interface control module of the controller 18 generates a signal to adjust an operational parameter accordingly, such as by reducing the rate at which the plasma constituent is removed through the first outlet 102 under action of a pump of the blood separation device 10. The interface INT moves toward the desired control position (as FIG. 18 shows), where the error signal is zero.

A positive error signal indicates that the optically dense layer RBC on the ramp 106 is too small (as FIGS. 20 and 42 show). The interface control module of the controller 18 generates a signal to adjust an operational parameter accordingly, such as by increasing the rate at which the plasma constituent is removed through the first outlet 102 under action of a pump of the blood separation device 10. The interface INT moves toward the desired control position (FIG. 18), where the error signal is again zero.

It should be understood that this system for controlling the location of the interface INT is merely exemplary and that differently configured and/or functioning systems may be employed without departing from the scope of the present disclosure.

III. Exemplary Separation Procedures

Exemplary blood separation procedures that may be carried out using systems and techniques according to the present disclosure will now be described.

Depending on the blood separation objectives, there is a suitable procedure for separating and collecting any of a variety of different blood components, either alone or in combination with other blood components. Accordingly, prior to processing, an operator selects the desired protocol (e.g., using an operator interface station, if provided), which informs the controller 18 of the manner in which it is to control the other components of the blood separation device 10 during the procedure.

The operator may also proceed to enter various parameters, such as information regarding the blood source. In one embodiment, the operator also enters the target yield for the various blood components (which may also include entering a characteristic of the blood, such as a platelet pre-count) or some other collection control system (e.g., the amount of whole blood to be processed).

If there are any fluid containers (e.g., a storage solution container) that are not integrally formed with the fluid flow circuit 12, they may be connected to the fluid flow circuit 12 (e.g., by piercing a septum of a tube of the fluid flow circuit 12 or via a luer connector), with the fluid flow circuit 12 then being mounted to the blood separation device 10 (including the fluid containers F1-F9 being hung from the weight scales W1-W6 and the hooks or supports H1 and H2, as appropriate). An integrity check of the fluid flow circuit 12 may be executed by the controller 18 to ensure the various components are properly connected and functioning. Following a successful integrity check, the blood source is connected to the fluid flow circuit 12 and the fluid flow circuit 12 may be primed (e.g., by saline pumped from a saline bag F2 by operation of one or more of the pumps P1-P6 of the blood separation device 10).

When the fluid flow circuit 12 has been primed, blood separation may begin. The stages of blood separation vary depending on the particular procedure, and will be described in greater detail below.

A. Red Blood Cell Collection

According to one aspect of the present disclosure, the blood separation device 10 may be used to separate and collect red blood cells from blood. If the blood source is a donor, it is typically safe to collect two units of red blood cells (a total of approximately 400 ml), but it is also within the scope of the present disclosure for a different amount of red blood cells to be collected.

1. Fluid Flow Circuit

FIG. 2A is a schematic view of an exemplary fluid flow circuit 12a having a single blood access device (e.g., a needle) for separating and collecting red blood cells from blood. The fluid flow circuit 12a includes a cassette 48 of the type described above and illustrated in FIG. 4, which connects the various components of the fluid flow circuit 12a. The various connections amongst the components of the fluid flow circuit 12 are shown in FIG. 2A, which also shows the fluid flow circuit 12a mounted to the blood separation device 10.

Components of the fluid flow circuit 12a interact with many of the components of the blood separation device 10, as will be described, but there are selected components of the blood separation device 10 that are not used in separating and collecting red blood cells using the fluid flow circuit 12a of FIG. 2A. Most notably, the spinning membrane separator drive unit 14 is not used, but only the centrifugal separator 16. There is also a valve V9, a pump P6, a spinner outlet sensor M2, and a pressure sensor A4 of the blood separation device 10 that are not used in the procedure described herein.

2. Draw Phase

Figure 43:
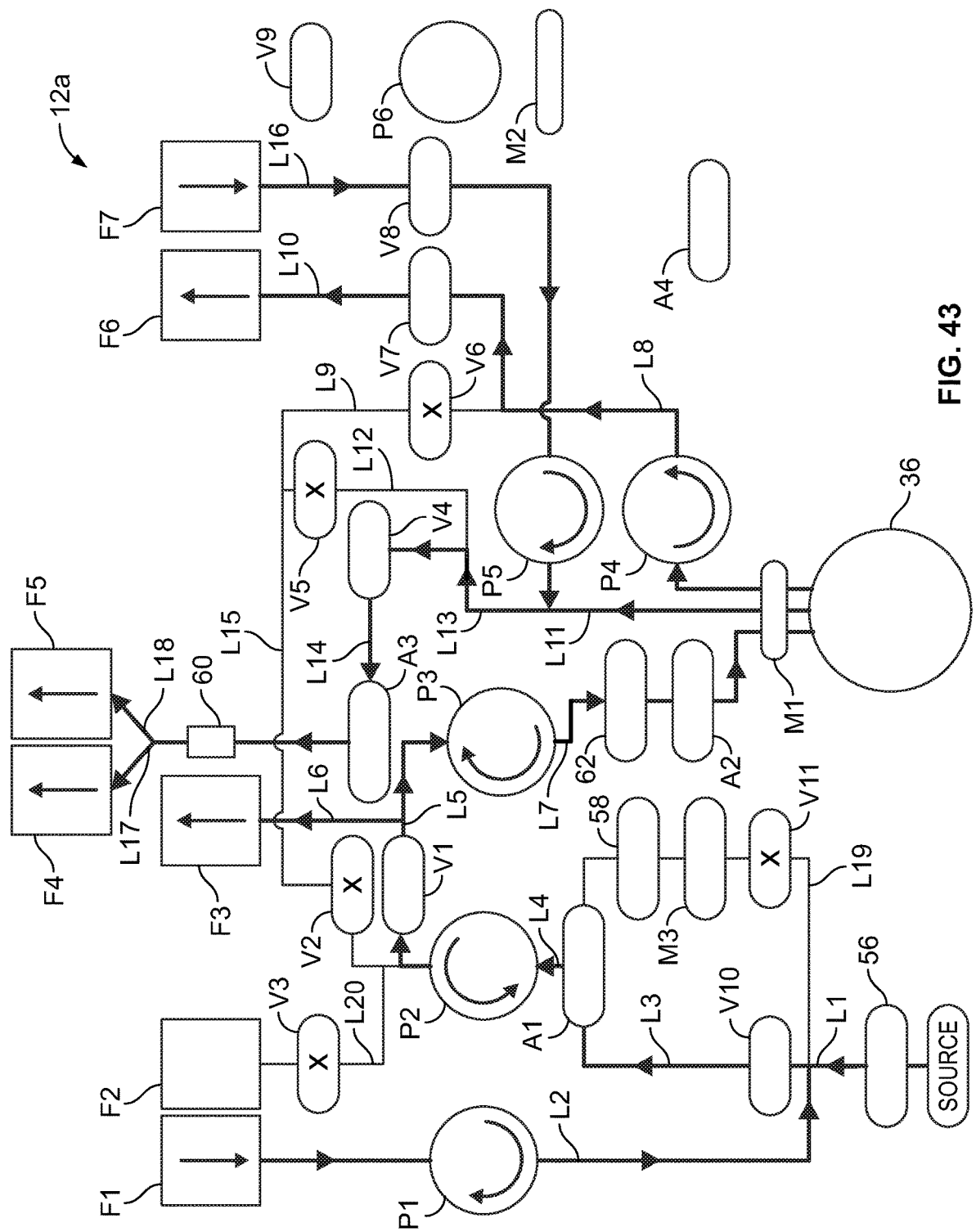
FIGS. 43-45 are schematic views of the fluid flow circuit of FIG. 2A mounted on the blood separation device of FIG.

In a first phase (FIG. 43), blood is drawn into the fluid flow circuit 12a from a blood source. If the blood source is a donor, then blood may be drawn into the fluid flow circuit 12a through a single needle that is connected to the cassette 48 by line L1. The line L1 may include a manual clamp 56 that may initially be in a closed position to prevent fluid flow through the line L1. When processing is to begin, an operator may move the manual clamp 56 from its closed position to an open position to allow fluid flow through the line L1. The term "line" is used herein to refer to any fluid flow conduit, whether a flexible tube that is connected to the cassette 48 or a rigidly defined flow path of the cassette 48, and a particular line is not limited to a flexible conduit or a rigidly defined conduit unless stated to the contrary.

The blood is drawn into the line L1 by a pump P2 of the blood separation device 10, which may be referred to as the source pump. As described above, the source pump P2 may be a peristaltic pump that interacts with a tubing loop T2 extending from the cassette 48 of the fluid flow circuit 12a. Anticoagulant may be added to the blood (such that the term "blood" as used herein should be understood to encompass blood with or without anticoagulant added thereto) via line L2 under action of a pump P1 of the blood separation device 10 (which may be referred to as the anticoagulant pump). The anticoagulant pump P1 may be a peristaltic pump that interacts with a tubing loop T1 of the fluid flow circuit 12a to draw anticoagulant from a fluid container F1 (which may be referred to as an anticoagulant bag), through line L2, and through a junction of lines L1 and L2, where it is mixed with blood flowing into the fluid flow circuit 12a.

In the illustrated embodiment, the valve station C10 associated with valve V10 is open to allow blood to flow through lines L3 and L4 and a sensor station S1 associated with pressure sensor A1 of the blood separation device 10. If the blood source is a living body (e.g., a donor), the pressure sensor A1 may communicate with the controller 18 to monitor the pressure within the vein of the blood source.

The cassette 48 includes two valve stations C1 and C2 downstream of the source pump P2, which are associated with valves V1 and V2 (respectively) of the blood separation device 10. One valve V2 is closed to prevent fluid flow through the associated valve station C2, while the other valve V1 is open to allow fluid flow through the associated valve station C1. The blood flows through the line L5 associated with the open valve V1 to a junction, where a portion of the blood is directed through line L6 to a fluid container F3 (which may be referred to as an in-process bag) and the remainder is directed through line L7 toward the centrifugal separation chamber 36. The line L7 is associated with a pump P3 (which may be referred to as a centrifuge pump), which controls the amount of blood that is directed to the centrifugal separation chamber 36 instead of the in-process bag F3. In particular, the flow rate of the source pump P2 is greater than the flow rate of the centrifuge pump P3, with the difference therebetween being equal to the flow rate of blood into the in-process bag F3. The flow rates may be selected such that the in-process bag F3 is partially or entirely filled with blood at the end of the draw phase.

The blood flowing through line L7 toward the centrifugal separation chamber 36 passes through an air trap 62, a sensor station S2 associated with pressure sensor A2, and a centrifugal separator sensor M1 (which monitors the pressure of the centrifugal separation chamber 36). The centrifugal separator sensor M1 may detect the hematocrit of the blood entering the centrifugal separation chamber 36.

The centrifugal separator 16 of the blood separation device 10 manipulates the centrifugal separation chamber 36 to separate red blood cells from a plasma constituent, which may be platelet-rich plasma or platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and a plasma constituent (as described above).

The plasma constituent is pumped out of the centrifugal separation chamber 36 via line L8 under action of a pump P4 of the blood separation device 10 (which may be referred to as the plasma pump). Valve V6 is closed to prevent fluid flow through associated valve station C6 and line L9, while valve V7 is open to allow fluid flow through associated valve station C7 and line L10, thereby directing the flow of the plasma constituent through line L10 and into a fluid container F6, which may be referred to as a return bag.

The red blood cells flow out of the centrifugal separation chamber 36 via line L11. There is no pump associated with line L11, so instead the flow rate at which the red blood cells exit the centrifugal separation chamber 36 is equal to the difference between the flow rates of the centrifuge pump P3 and plasma pump P4. Valve V5 is closed to prevent fluid flow through associated valve station C5 and line L12, while valve V4 associated with valve station C4 is open to direct the flow of red blood cells from line L11 through lines L13 and L14 and toward a leukocyte removal filter 60. While a majority of the white blood cells in the blood may be separated from the red blood cells and allowed to build up in the centrifugal separation chamber 36 during the procedure (for optional return to the blood source following collection of the red blood cells), the leukocyte removal filter 60 may remove any white blood cells (e.g., granulocytes) that exit the centrifugal separation chamber 36 with the red blood cells. Pressure sensor A3 may interact with sensor station S3 of the cassette 48 to monitor the pressure of the leukocyte removal filter 60. The valve V5 associated with valve station C5 may be selectively opened to allow fluid flow through line L12 and into line L15. This may be advantageous if the controller 18 determines that sufficient red blood cells have been collected and that further red blood cells may be conveyed to a recipient.

Prior to the red blood cells reaching the leukocyte removal filter 60, they may be mixed with an additive solution, such as Adsol. The additive solution may be drawn out of a fluid container F7 (which may be referred to as an additive bag) via line L16 (with open valve V8) under action of a pump P5 (which may be referred to as an additive pump). The additive pump P5 conveys additive solution through line L16 and open valve station C8 to a junction where it is mixed with the red blood cells flowing through line L11. The additive pump P5 may operate at a rate that is based on the hematocrit of the blood entering the centrifugal separation chamber 36 (as detected by the centrifugal separator sensor M1), with additive solution being added to the red blood cells at a rate configured to produce a mixture having a predetermined or preselected hematocrit (which may be in a range of approximately 55% to approximately 75% in one exemplary embodiment and in a range of approximately 60% to approximately 65% in another exemplary embodiment). More particularly, the hematocrit of the red blood cells exiting the centrifugal separation chamber 36 may be calculated as follows:

Hematocrit of RBC (%)=(rate of centrifuge pump P3*hematocrit of blood entering centrifugal separation chamber 36)/(rate of centrifuge pump P3−rate of plasma pump P4)  [Equation 2]

When the hematocrit of the red blood cells exiting the centrifugal separation chamber 36 is known, it can be reduced to a target level by operating the additive pump P5 at a suitable rate.

The mixture of red blood cells and additive solution is conveyed through lines L13 and L14 and the leukocyte removal filter 60, which removes the majority of the white blood cells and residual platelets from the mixture. The leukoreduced red blood cells are conveyed through lines L17 and L18 to fluid containers F4 and F5 (which may be referred to as red blood cell bags), respectively.

The draw phase may continue until the amount of blood drawn from the blood source reaches a target amount or the in-process bag F3 is filled to a particular level (as determined by a weight scale from which the in-process bag F3 is hung) or until some other condition is satisfied.

3. Return Phase

When the system transitions to the return phase (FIG. 44), the anticoagulant pump P1 will stop drawing anticoagulant from the anticoagulant bag F1. The valve V10 associated with valve station C10 will close to prevent fluid flow through line L3, and valve V11 associated with valve station C11 is opened to allow fluid flow through line L19. The valve V2 associated with valve station C2 also opens to allow flow through line L15, while the valve V1 associated with valve station C1 closes to prevent flow through line L5. The valve V6 associated with valve station C6 will also open, allowing fluid flow through line L9.

With the valves so situated, the source pump P2 will reverse direction to allow the contents of the return bag F6 (typically plasma) to be conveyed to a recipient (which may be the same blood source) via the same needle used to draw blood into the fluid flow circuit 12a. The return fluid is pumped through line L10, the valve station C7 associated with open valve V7, and line L9 and the valve station C6 associated with open valve V6. Valve V5 associated with valve station C5 remains closed, thereby directing the return fluid through line L15 and the valve station V2 associated with open valve V2. As described above, the valve V1 associated with valve station C1 is closed, thereby directing the return fluid through line L4, the sensor station S1 associated with pressure sensor A1, a return line filter 58, air detector M3, the valve station C11 associated with open valve V11, and lines L19 and L1 on its way to the recipient.

Depending on user preference, the valve V3 associated with valve station C3 may be opened (as in FIG. 45) to cause saline or another replacement fluid to be drawn from the saline bag F2 via line L20 by the source pump P2 to a junction, where it mixes with fluid being conveyed to a recipient. As shown in FIG. 45, this may include closing the valve V7 associated with valve station C7 to prevent fluid flow through line L10, in which case replacement fluid from the saline bag F2 and not return fluid from the return bag F6 will be conveyed to the recipient. In one embodiment, the stages shown in FIGS. 44 and 45 may be alternated during the return phase to allow for plasma and replacement fluid to be alternately conveyed to the blood source. In yet another embodiment, the valve V7 associated with valve station C7 may remain open, such that a mixture of replacement fluid from the saline bag F2 and return fluid from the return bag F6 will be conveyed to the recipient. In a further embodiment, the valve V6 associated with valve station C6 may be closed, while the valve V7 associated with valve station C7 and the valve V3 associated with valve station C3 are open, which allows for replacement fluid from the saline bag F2 to be conveyed to the recipient while plasma exiting the centrifugal separation chamber 36 (as will be described in greater detail) is directed into the return bag F6. The return phase of a single procedure may include one or more of these stages, carried out in any order, without departing from the scope of the present disclosure.

While fluid is being conveyed to the recipient, the blood in the in-process bag F3 acts as the blood supply for the centrifugal separation chamber 36. When the system transitions to the return phase, the centrifuge pump P3 remains unchanged and separation continues in the same manner as described for the draw phase (i.e., with blood being separated into red blood cells and a plasma constituent, the plasma constituent flowing out of the centrifugal separation chamber 36, and the red blood cells being diluted, filtered, and collected as leukoreduced red blood cells) until the in-process bag F3 is emptied. Therefore, the system components downstream from the centrifuge pump P3 are "blinded" as to whether the system is in a draw or return phase. It will be appreciated that a method as described herein is preferable to a batch process (by which blood is only separated during a draw phase and not during a return phase) because separation and collection may be continuous, thereby decreasing the time required to complete the procedure.

Figure 44:
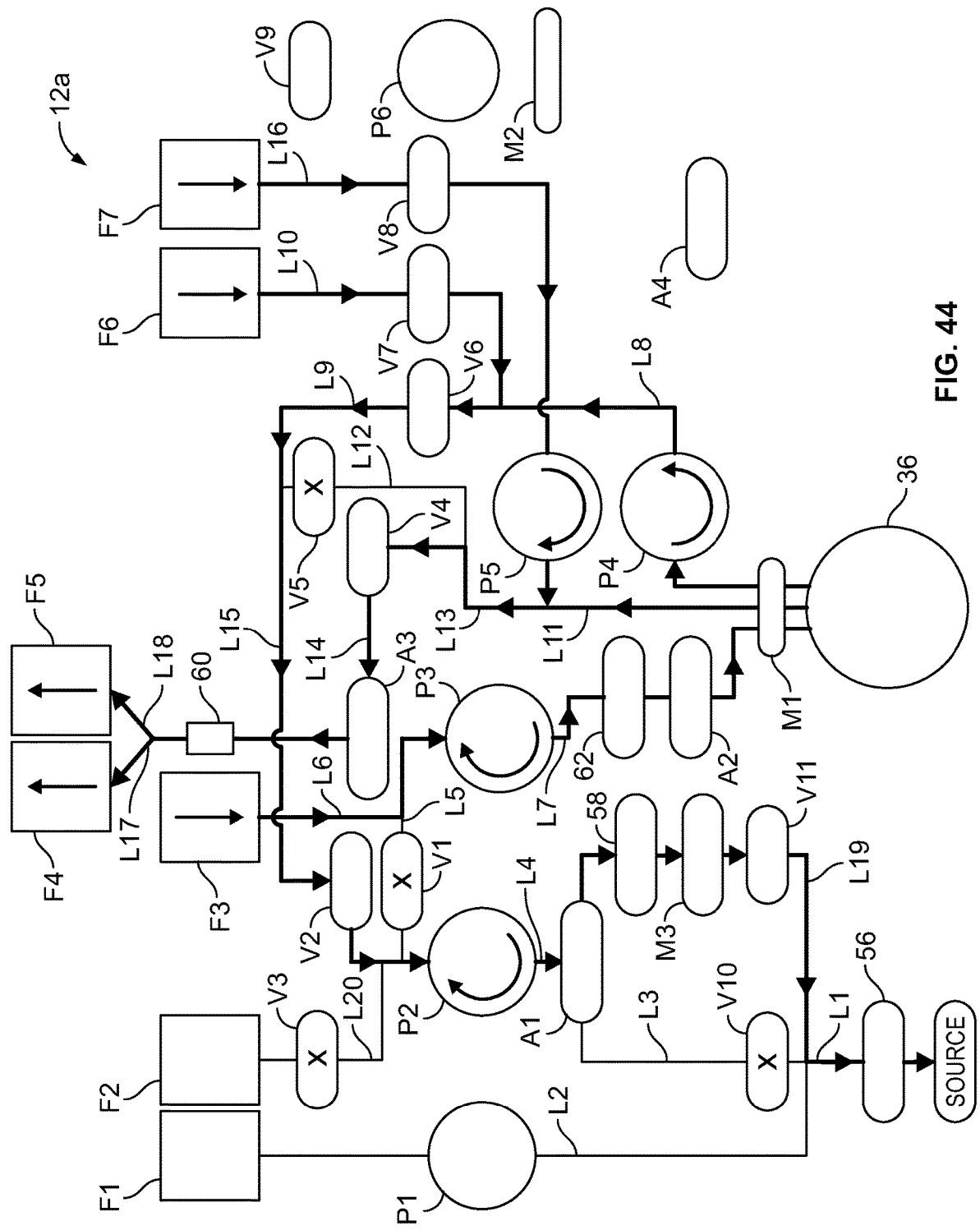
Figure 45:
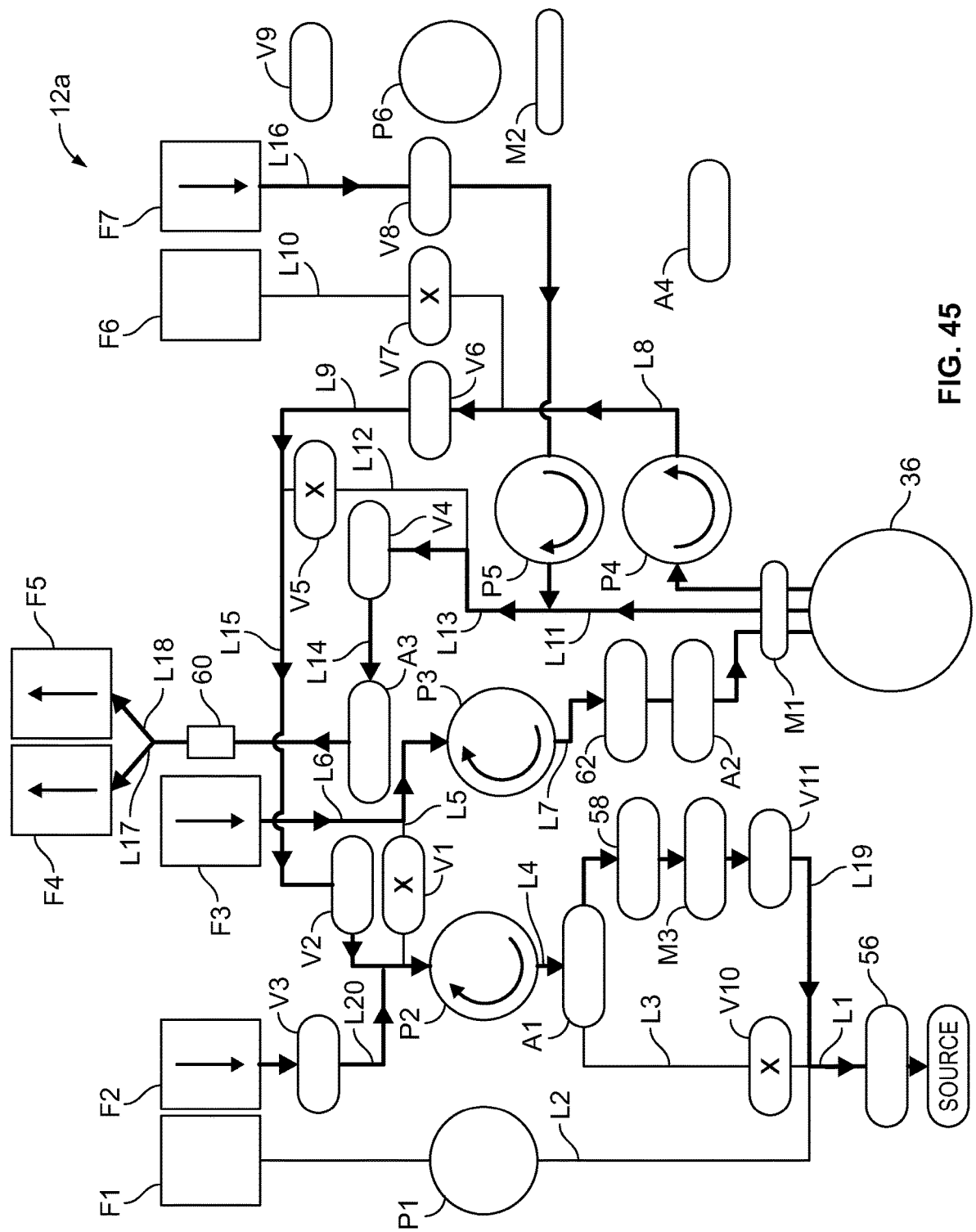
Figure 46:
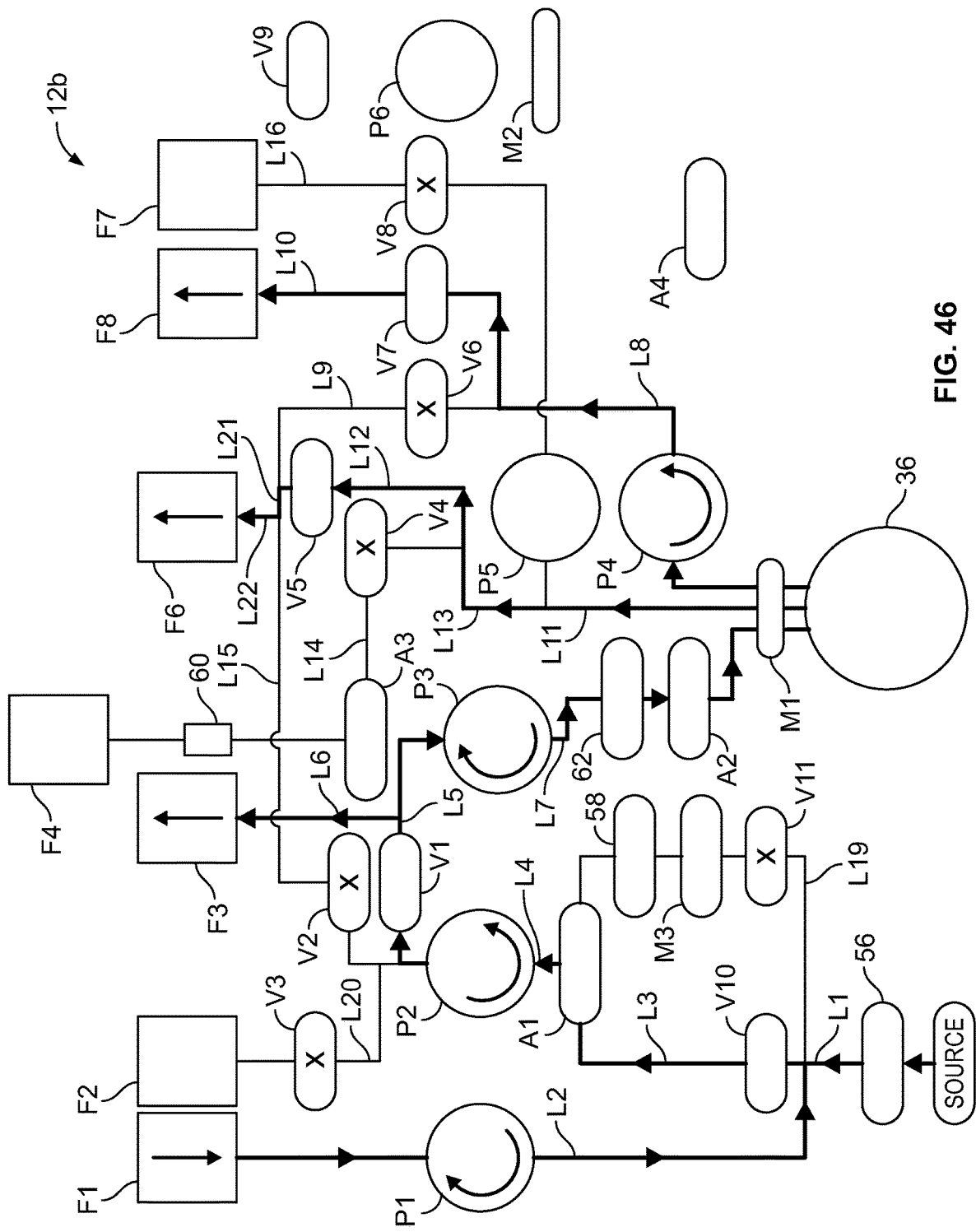

As shown in FIGS. 44 and 45, due to the valve V6 associated with valve station C6 being open, the plasma constituent will flow into and through lines L9 and L15 for conveyance to the recipient, along with return fluid from the return bag F6 (FIG. 44) or replacement fluid from the saline bag F2 (FIG. 45) or both. It will be seen in FIG. 44 that the plasma constituent may be conveyed toward the return bag F6 at the same time that the contents of the return bag F6 are being conveyed to the recipient. The rate at which the source pump P2 operates may be greater than the rate at which the plasma pump P4 operates to allow the return bag F6 to empty during the return phase, even as separation continues. Once the return bag F6 and/or in-process bag F3 is empty, the system may transition back to the draw phase if the target amount of red blood cells has not yet been collected.

B. Red Blood Cell and Plasma Collection

According to one aspect of the present disclosure, the blood separation device 10 may be used to separate and collect red blood cells and plasma from blood. In contrast to the preceding procedure in which only red blood cells are collected, it is typical for only a single unit of red blood cells to be collected, along with a target amount of plasma. However, other amounts of red blood cells and plasma may be separated and collected without departing from the scope of the present disclosure.

A blood separation device 10 according to the present disclosure may be used in combination with a fluid flow circuit 12 configured to produce an unfiltered or a filtered plasma product. Exemplary fluid flow circuits and procedures will be described for each arrangement.

1. Unfiltered Plasma Product Fluid Flow Circuit and Procedure a. Fluid Flow Circuit FIG. 2B is a schematic view of an exemplary fluid flow circuit 12b having a single blood access device (e.g., a needle) for separating and collecting red blood cells and plasma from blood. The fluid flow circuit 12c includes a cassette 48 of the type described above and illustrated in FIG. 4, which connects the various components of the fluid flow circuit 12b. The various connections amongst the components of the fluid flow circuit 12c are shown in FIG. 2B, which also shows the fluid flow circuit 12b mounted to the blood separation device 10. Due to similarities between the fluid flow circuit 12b of FIG. 2B and the fluid flow circuit 12a of FIG. 2A, similarly configured fluid lines will be identified with the same reference labels in FIGS. 2A and 2B, while lines that are differently configured and/or not employed in the fluid flow circuit 12a of FIG. 2A will be identified in FIG. 2B with different reference labels.

Components of the fluid flow circuit 12b interact with many of the components of the blood separation device 10, as will be described, but there are selected components of the blood separation device 10 that are not used in separating and collecting red blood cells and plasma using the fluid flow circuit 12b of FIG. 2B. Most notably, the spinning membrane separator drive unit 14 is not used, but only the centrifugal separator 16. There is also a valve V9, a pump P6, a spinner outlet sensor M2, and a pressure sensor A4 of the blood separation device 10 that are not used in the procedure described herein.

b. Draw Phase—Plasma Collection Only

The volume of blood required to produce typical plasma product volumes is more than the volume of blood required to produce the corresponding red blood cell product volumes and, thus, there may be two draw phases. One phase only collects plasma (while conveying red blood cells to a recipient) and the other phase collects plasma and red blood cells. Plasma-only collection occurs for a majority of the draw phases while plasma and red blood cell collection occurs near the end of the procedure. The plasma-only draw phase will continue until the collected plasma volume is within a specific amount of the target product volume and then the system will collect both plasma and red blood cells. The transition will occur when the collected plasma volume is within the volume of plasma that will be produced in order to obtain the target red blood cell product volume, typically 200 ml of red blood cells. For example, for blood having a hematocrit of 40%, 500 ml of blood will have to be processed in order to collect 200 ml of red blood cells. Assuming the separated red blood cells exiting the centrifugal separation chamber 36 has a hematocrit of 80%, then 250 ml of plasma will be produced when processing the 500 ml of blood. Therefore, plasma-only collection would continue from the start of a procedure until the collected plasma volume is within 250 ml of the target plasma product volume.

In the plasma-only draw phase (FIG. 46), blood is drawn into the fluid flow circuit 12b from a blood source. If the blood source is a donor, then blood may be drawn into the fluid flow circuit 12b through a single needle that is connected to the cassette 48 by line L1. The line L1 may include a manual clamp 56 that may initially be in a closed position to prevent fluid flow through the line L1. When processing is to begin, an operator may move the manual clamp 56 from its closed position to an open position to allow fluid flow through the line L1.

The blood is drawn into the line L1 by the source pump P2 of the blood separation device 10. Anticoagulant may be drawn from the anticoagulant bag F1 by the anticoagulant pump P1, which conveys the anticoagulant through line L2 to a junction, where it is mixed with blood flowing through line L1 into the fluid flow circuit 12b.

In the illustrated embodiment, the valve V10 associated with valve station C10 is open to allow blood to flow through line L3 and a sensor station S1 associated with pressure sensor A1. If the blood source is a living body (e.g., a donor), the pressure sensor A1 may communicate with the controller 18 to monitor the pressure within the vein of the blood source.

The cassette 48 includes two valve stations C1 and C2 downstream of the source pump P2 and line L4, with the valve V2 of one valve station C2 being closed and the valve V1 of the other valve station C1 being open. The blood flows through the line L5 associated with the open valve V1 to a junction, where a portion of the blood is directed through line L6 to the in-process bag F3 and the remainder is directed through line L7 toward the centrifugal separation chamber 36. The centrifuge pump P3 is associated with line L7 and controls the amount of blood that is directed to the centrifugal separation chamber 36 instead of the in-process bag F3. In particular, the flow rate of the source pump P2 is greater than the flow rate of the centrifuge pump P3, with the difference therebetween being equal to the flow rate of blood into the in-process bag F3. The flow rates may be selected such that the in-process bag F3 is partially or entirely filled with blood at the end of this draw phase.

The blood flowing through line L7 toward the centrifugal separation chamber 36 passes through an air trap 62, a sensor station S2 associated with pressure sensor A2 (which monitors the pressure of the centrifugal separation chamber 36), and a centrifugal separator sensor M1. The centrifugal separator sensor M1 may detect the hematocrit of the blood entering the centrifugal separation chamber 36.

The centrifugal separator 16 of the blood separation device 10 manipulates the centrifugal separation chamber 36 to separate red blood cells from a plasma constituent, which may be platelet-rich plasma or (more preferably) platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and a plasma constituent (as described above).

The plasma constituent is pumped out of the centrifugal separation chamber 36 via line L8 under action of the plasma pump P4. Valve V6 is closed to prevent fluid flow through associated valve station C6 and line L9, while valve V7 is open to allow fluid flow through associated valve station C7 and line L10, thereby directing the flow of the plasma constituent through line L10 and into a fluid container F8, which may be referred to as a plasma bag. The valve V6 associated with valve station C6 may be selectively opened to allow fluid flow through line L9, L21, and L22 and into the return bag F6. This may be advantageous if the controller 18 determines that a sufficient amount of plasma has been collected and that further plasma may be conveyed to a recipient.

The red blood cells flow out of the centrifugal separation chamber 36 via line L11. There is no pump associated with line L11, so instead the flow rate at which the red blood cells exit the centrifugal separation chamber 36 is equal to the difference between the flow rates of the centrifuge pump P3 and plasma pump P4. Valve V4 associated with valve station C4 and valve V8 associated with valve station C8 are closed to prevent fluid flow through associated lines L14 and L16 (respectively), while valve V5 associated with valve station C5 is open to direct the flow of red blood cells from line L11 through lines L13 and L12. As described above, valve V2 associated with valve station C2 and valve V6 associated with valve station C6 are closed, thereby directing the red blood cells through lines L21 and L22 and into the return bag F6.

As described above, the plasma-only draw phase may continue until the amount of blood drawn from the blood source reaches a target amount or the in-process bag F3 is filled to a particular level (as determined by a weight scale from which the in-process bag F3 is hung) or until some other condition is satisfied.

c. Return Phase

When the system transitions to the return phase (FIG. 47), the anticoagulant pump P1 will stop drawing anticoagulant from the anticoagulant bag F1. The valve V10 associated with valve station C10 will close to prevent fluid flow through line L3, and the valve V11 associated with valve station C11 is opened to allow fluid flow through line L19. The valve V2 associated with valve station C2 also opens to allow flow through line L15, while the valve V1 associated with valve station C1 closes to prevent flow through line L5.

With the valves so situated, the source pump P2 will reverse direction to allow the contents of the return bag F6 (typically red blood cells) to be conveyed to a recipient (which may be the same blood source) via the same needle used to draw blood into the fluid flow circuit 12b. The return fluid is pumped through lines L22 and L15, the valve station C2 associated with open valve V2, line L4, the sensor station S1 associated with pressure sensor A1, line L19, a return line filter 58, air detector M3, the valve station C11 associated with open valve V11, and line L1 on its way to the recipient. Saline or another replacement fluid may be drawn from the saline bag F2 via line L20 by the source pump P2 to a junction, where it mixes with fluid being conveyed to the recipient, although it may be more typical for replacement fluid to not be conveyed to the recipient until plasma collection is complete.

While fluid is being conveyed to the recipient, the blood in the in-process bag F3 acts as the blood supply for the centrifugal separation chamber 36. When the system transitions to the return phase, the centrifuge pump P3 remains unchanged and separation continues in the same manner as described for the plasma-only draw phase (i.e., with blood being separated into a plasma constituent and red blood cells, the red blood cells flowing out of the centrifugal separation chamber 36, and the plasma being collected in the plasma bag F8) until the in-process bag F3 is emptied. Therefore, the system components downstream from the centrifuge pump P3 are "blinded" as to whether the system is in the plasma-only draw phase or the return phase.

Figure 47:
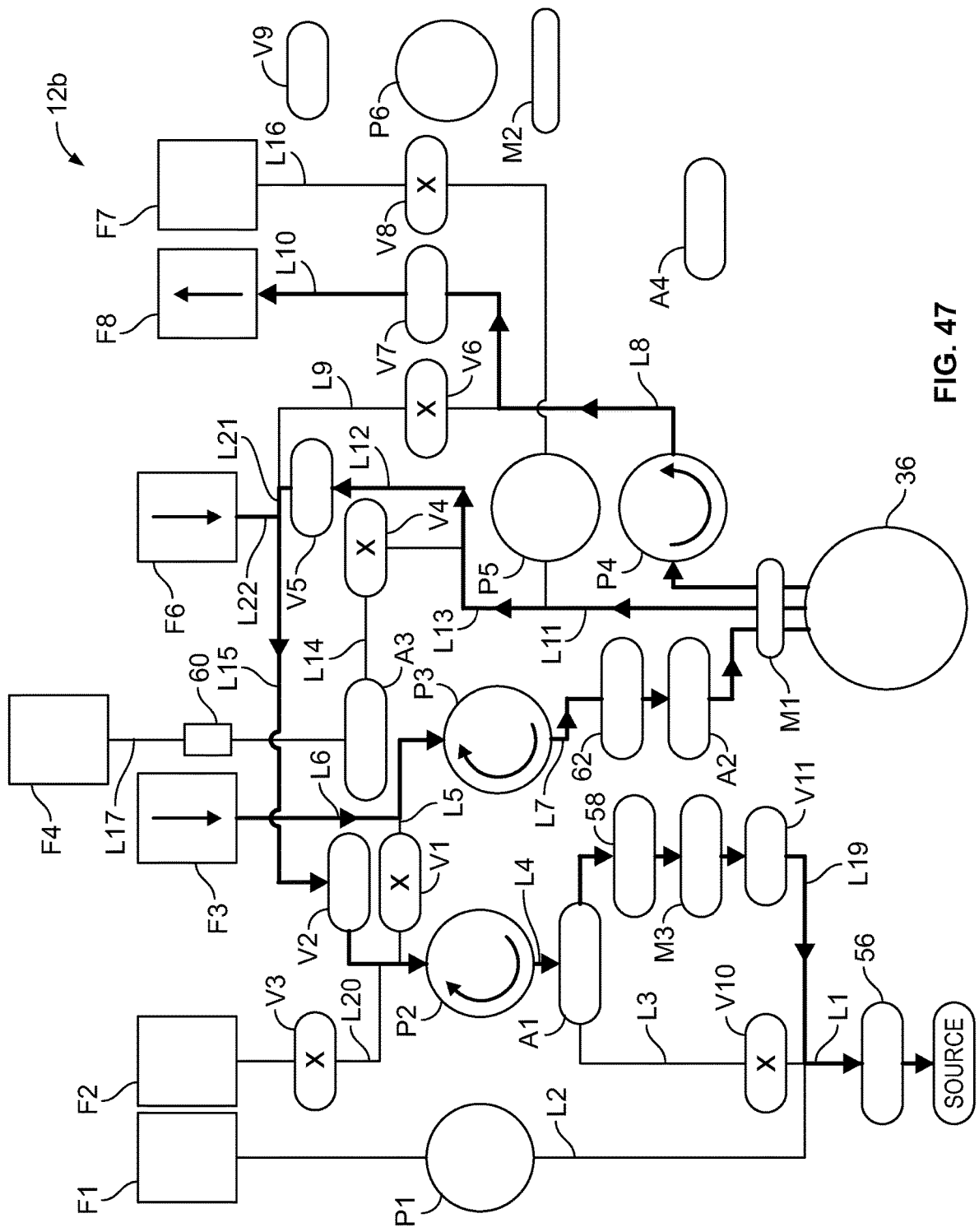

As shown in FIG. 47, due to the valve V2 associated with valve station C2 being open, the red blood cells will flow into and through lines L21 and L15 for conveyance to the recipient, along with return fluid from the return bag F6. It will be seen that the red blood cells are conveyed toward the return bag F6 at the same time that the contents of the return bag F6 are being conveyed to the recipient. The rate at which the source pump P2 operates may be greater than the rate at which the red blood cells are conveyed toward the return bag F6 to allow the return bag F6 to empty during the return phase, even as separation continues. Once the return bag F6 is empty, the system may transition back to the plasma-only draw phase (FIG. 46) and subsequently alternate between the plasma-only draw phase and return phase until enough plasma has been collected to begin red blood cell collection.

d. Draw Phase—Red Blood Cell and Plasma Collection

Figure 48:
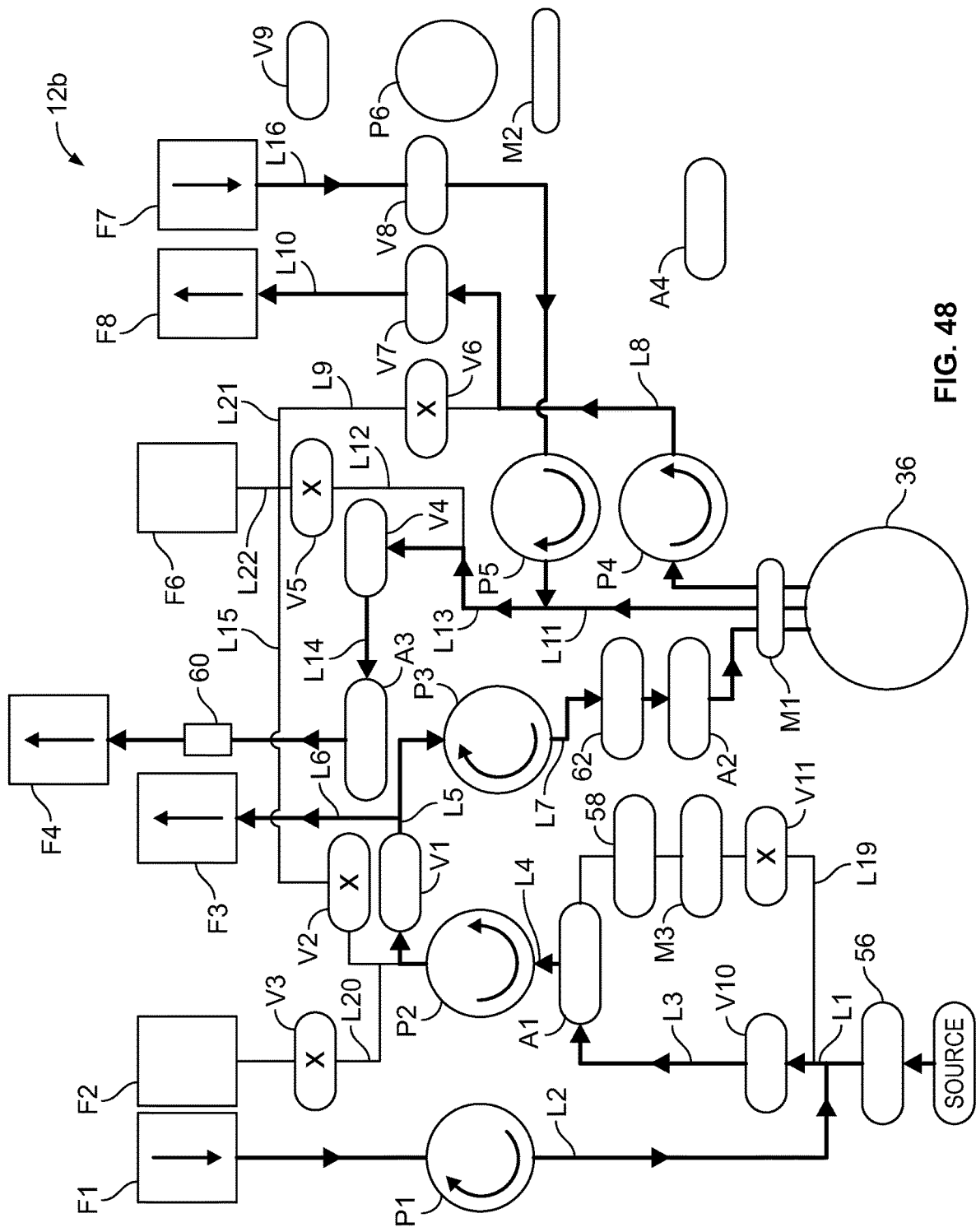

Once the plasma collection volume in plasma bag F8 is within a specific amount of the target (as explained above), the system will transition into a draw phase during which both plasma and red blood cells are collected, as shown in FIG. 48. This is the last draw phase of the procedure and will collect the red blood cell product and the remaining plasma volume. This draw phase is the same as the plasma-only draw phase until the red blood cells exit the centrifugal separation chamber 36. In this phase, the valve V5 associated with valve station C5 is closed to prevent flow through line L12 (to the return bag F6) and the valve V4 associated with valve station C4 is opened to allow the separated red blood cells to flow through line L14 toward the leukocyte removal filter 60. Pressure sensor A3 may interact with sensor station S3 of the cassette 48 to monitor the pressure of the leukocyte removal filter 60. The valve V5 associated with valve station C5 may be selectively opened to allow fluid flow through lines L12, L21, and L22 and into the return bag F6. This may be advantageous if the controller 18 determines that sufficient red blood cells have been collected and that further red blood cells may be conveyed to a recipient.

Prior to the red blood cells reaching the leukocyte removal filter 60, they may be mixed with an additive solution, such as Adsol. The additive solution may be drawn out of the additive bag F7 via line L16 (with the valve V8 associated with valve station C8 open) under action of the additive pump P5. The additive pump P5 conveys additive solution through line L16 and open valve station C8 to a junction where it is mixed with the red blood cells flowing through line L11. The additive pump P5 may operate at a rate that is based on the hematocrit of the blood entering the centrifugal separation chamber 36 (which rate may be calculated using Equation 2, for example), with additive solution being added to the red blood cells at a rate configured to produce a mixture having a predetermined or preselected hematocrit (which may be in a range of approximately 55% to approximately 75% in one exemplary embodiment and in a range of approximately 60% to approximately 65% in another exemplary embodiment).

The mixture of red blood cells and additive solution is conveyed through line L14 and the leukocyte removal filter 60, which removes the majority of the platelets and white blood cells from the mixture. The leukoreduced red blood cells are conveyed from the leukocyte removal filter 60 to the red blood cell bag F4.

As in the plasma-only draw phase, the plasma constituent is pumped out of the centrifugal separation chamber 36 under action of the plasma pump P4 and flows into the plasma bag F8.

e. Final Phase

At a point during the draw phase of FIG. 48, the source pump P2 will have pumped enough blood into the fluid flow circuit 12b to allow for the targeted red blood cell and plasma product volumes to be reached. However, a specific volume of blood in the in-process bag F3 will have yet to be processed. At this point, the source pump P2 will stop drawing blood from the blood source and the valve V10 associated with valve station C10 will close to prevent fluid flow through line L3. The blood remaining in the in-process bag F3 will then be processed by the centrifugal separation chamber 36 to complete the procedure, as shown in FIG. 49.

Figure 49:
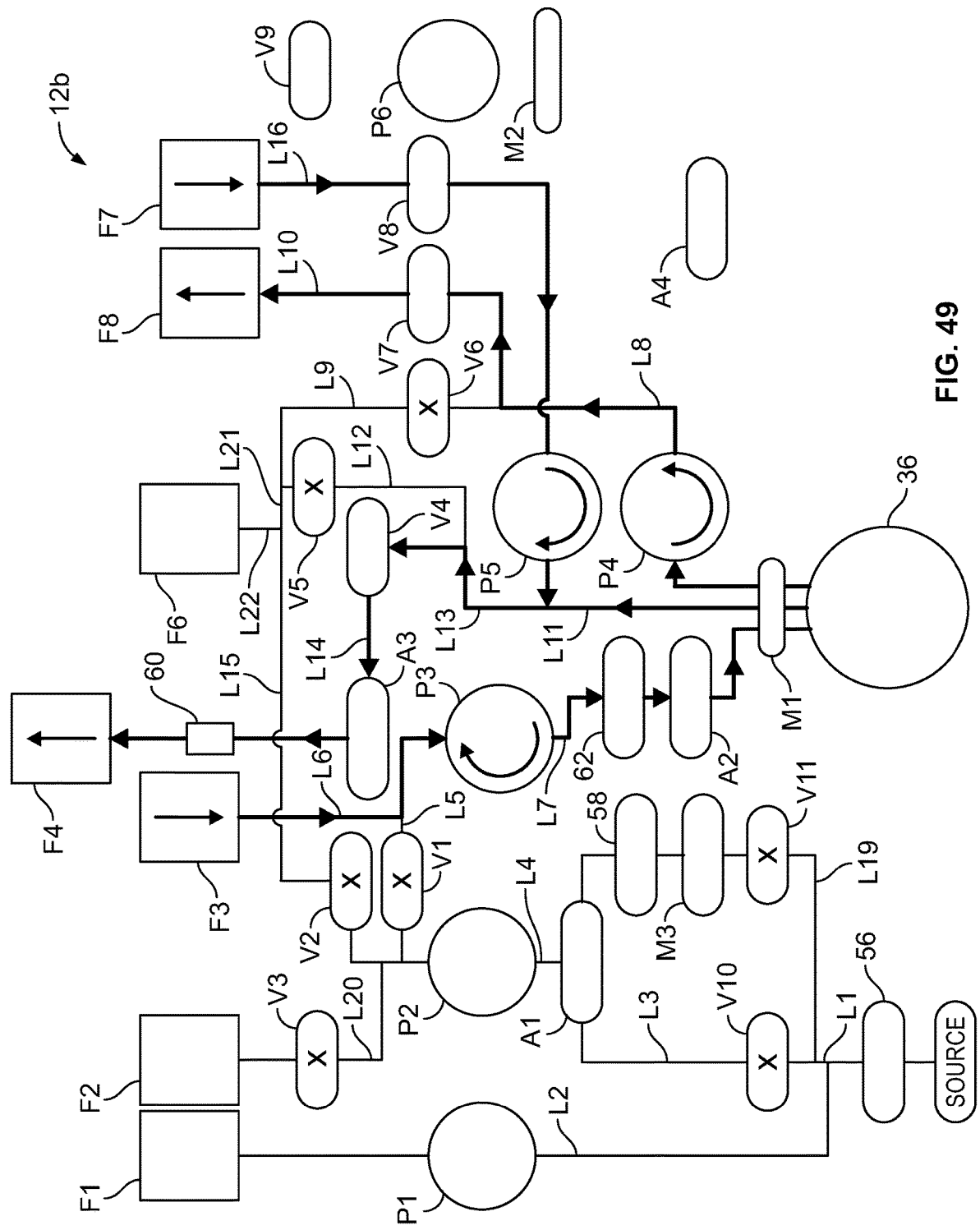

With the valve stations situated as shown in FIG. 49, the blood in the in-process bag F3 acts as the blood supply for the centrifugal separation chamber 36. Other than the blood entering the centrifugal separation chamber 36 from a different origin, this phase proceeds in the same manner as described for the final draw phase (i.e., with blood being separated into a plasma constituent and red blood cells, the plasma flowing to the plasma bag F8, and the red blood cells being diluted, filtered, and collected as leukoreduced red blood cells) until the in-process bag F3 is emptied. Upon emptying the in-process bag F3, the targeted amounts of red blood cell product and plasma product should be contained within the respective collection containers F4 and F8, which may be confirmed by the weight scales from which the containers F4 and F8 may be hung during the procedure.

2. Filtered Plasma Product Fluid Flow Circuit and Procedure a. Fluid Flow Circuit FIG. 2C is a schematic view of a fluid flow circuit 12c that is a variation of the fluid flow circuit 12b of FIG. 2B. As described above, the blood separation device 10 may be used to produce leukoreduced red blood cells and an unfiltered plasma product, such as by the procedure illustrated in FIGS. 46-49. While the plasma product produced by such a procedure will tend to include an acceptably small amount of cellular blood components, a substantially or virtually cell-free plasma product may be produced by filtering the plasma constituent prior to collection. Such filtration may be carried out using the spinning membrane separator drive unit 14 of the blood separation device 10, along with a fluid flow circuit 12c having a spinning membrane separator 26 (as shown in FIG. 2C), which results in a plasma product having a lower cell content than is achievable by any type of centrifugation. Due to similarities between the fluid flow circuit 12c of FIG. 2C and the fluid flow circuit 12b of FIG. 2B, similarly configured fluid lines will be identified with the same reference labels in FIGS. 2B and 2C, while lines that are differently configured and/or not employed in the fluid flow circuit 12b of FIG. 2B will be identified in FIG. 2C with different reference labels.

Components of the fluid flow circuit 12c interact with many of the components of the blood separation device 10, as will be described, but there are selected components of the blood separation device 10 that are not used in separating and collecting red blood cells and filtered plasma using the fluid flow circuit 12c of FIG. 2C. In particular, one of the valves V9 and one of the pumps P6 of the blood separation device 10 are not used in the procedure described herein. As noted above, and in contrast to the fluid flow circuit 12b of FIG. 2B, the fluid flow circuit 12c of FIG. 2C interacts with both the centrifugal separator 16 and the spinning membrane separator drive unit 14 of the blood separation device 10.

b. Draw Phase—Plasma Collection Only

As described above with respect to the fluid flow circuit 12b of FIG. 2B, the volume of blood required to produce typical plasma product volumes is more than the volume of blood required to produce the corresponding red blood cell product volumes and, such that there may be two draw phases.

During the first, plasma-only draw phase (FIG. 50), blood is drawn into the fluid flow circuit 12c from a blood source. If the blood source is a donor, then blood may be drawn into the fluid flow circuit 12c through a single needle that is connected to the cassette 48 by line L1. The line L1 may include a manual clamp 56 that may initially be in a closed position to prevent fluid flow through the line L1. When processing is to begin, an operator may move the manual clamp 56 from its closed position to an open position to allow fluid flow through the line L1.

The blood is drawn into the line L1 by the source pump P2 of the blood separation device 10. Anticoagulant may be drawn from the anticoagulant bag F1 by the anticoagulant pump P1, which conveys the anticoagulant through line L2 to a junction, where it is mixed with blood flowing through line L1 into the fluid flow circuit 12c.

In the illustrated embodiment, the valve V10 associated with valve station C10 is open to allow blood to flow through line L3 and a sensor station S1 associated with pressure sensor A1. If the blood source is a living body (e.g., a donor), the pressure sensor A1 may communicate with the controller 18 to monitor the pressure within the vein of the blood source.

The cassette 48 includes two valve stations C1 and C2 downstream of the source pump P2, with the valve V2 of one valve station C2 being closed and the valve V1 of the other valve station C1 being open. The blood flows through the line L5 associated with the open valve V1 to a junction, where a portion of the blood is directed through line L6 to the in-process bag F3 and the remainder is directed through line L7 toward the centrifugal separation chamber 36. The centrifuge pump P3 is associated with line L7 and controls the amount of blood that is directed to the centrifugal separation chamber 36 instead of the in-process bag F3. In particular, the flow rate of the source pump P2 is greater than the flow rate of the centrifuge pump P3, with the difference therebetween being equal to the flow rate of blood into the in-process bag F3. The flow rates may be selected such that the in-process bag F3 is partially or entirely filled with blood at the end of this draw phase.

The blood flowing through line L7 toward the centrifugal separation chamber 36 passes through an air trap 62, a sensor station S2 associated with pressure sensor A2 (which monitors the pressure of the centrifugal separation chamber 36), and a centrifugal separator sensor M1. The centrifugal separator sensor M1 may detect the hematocrit of the blood entering the centrifugal separation chamber 36.

The centrifugal separator 16 of the blood separation device 10 manipulates the centrifugal separation chamber 36 to separate red blood cells from a plasma constituent, which may be platelet-rich plasma or (more preferably) platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and a plasma constituent (as described above).

The plasma constituent is pumped out of the centrifugal separation chamber 36 via line L8 under action of the plasma pump P4. Valve V6 is closed to prevent fluid flow through associated valve station C6 and line L9, while valve V7 is open to direct fluid flow through line L23, a sensor station S4 associated with pressure sensor A4 (which monitors the pressure of the spinning membrane separator 26), and into the spinning membrane separator 26. As described above, the separated plasma passes through the spinning membrane separator 26, which filters out any remaining cellular blood components, resulting in substantially or virtually cell-free plasma. The filtered plasma exits the spinning membrane separator 26 via line L24, passing through spinner outlet sensor M2 (which may monitor the filtered plasma to determine one or more of its properties, such as whether the plasma is hemolytic and/or lipemic), the valve station C7 associated with valve V7, and into plasma bag F8.

Figure 50:
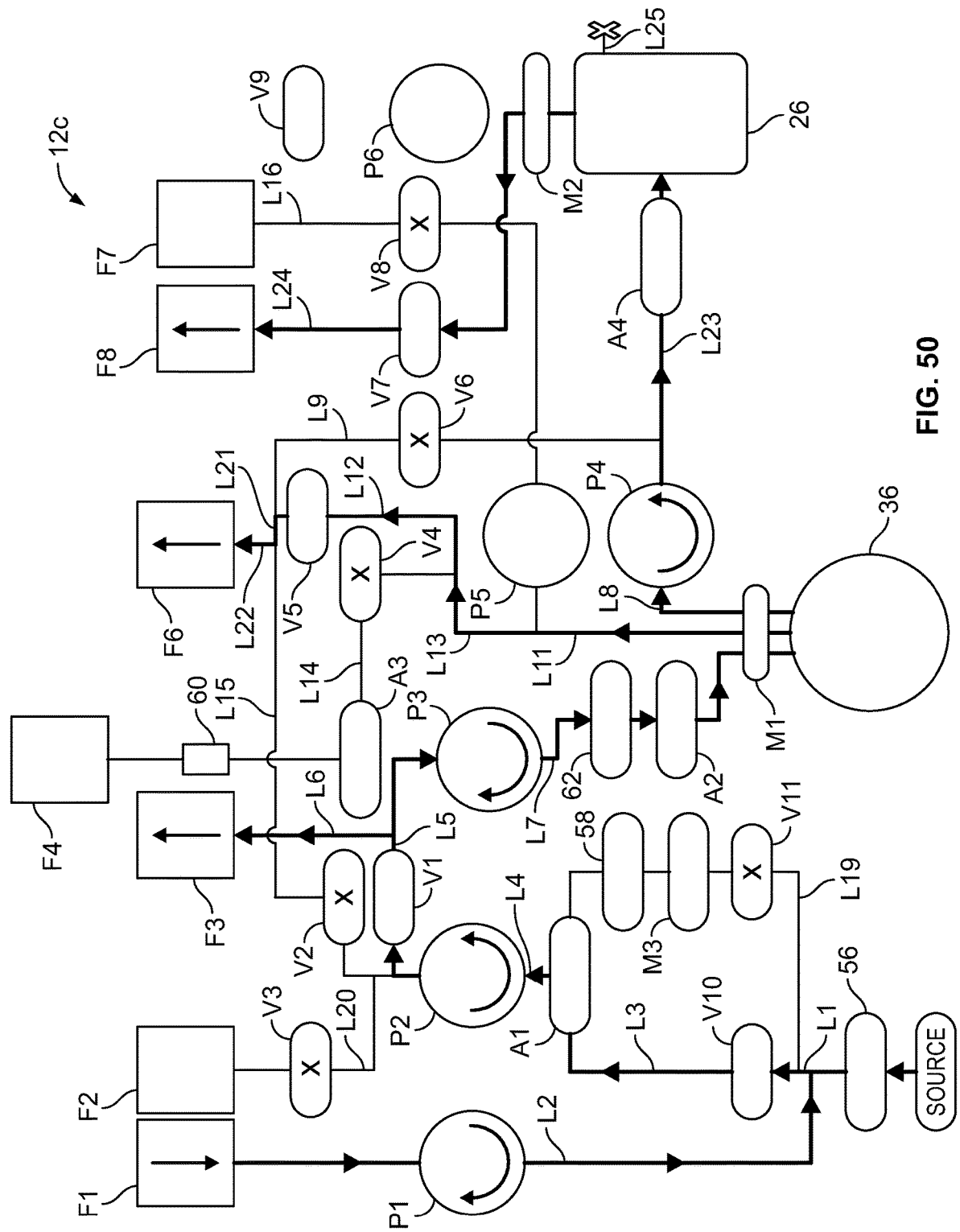

While the filtered plasma flows out of the spinning membrane separator 26, the cellular blood components remain in the gap 74 as a waste product that is eventually discarded with the spinning membrane separator 26 at the end of the procedure. As described above, this may be achieved by omitting an outlet associated with the gap 74 or otherwise preventing flow out of the gap 74. For example, if the spinning membrane separator 26 includes a fluid line L25 associated with the spinning membrane separator 26 for the outflow of fluid from the gap 74, that line L25 may be clamped or sealed or otherwise closed to fluid flow, as shown in FIG. 50. Flowing the cellular blood components out of the spinning membrane separator 26 would require some of the plasma to also flow out of the spinning membrane separator 26 via line L25, rather than exiting the spinning membrane separator 26 via line L24 as a filtered plasma product. Accordingly, "dead end" filtering the separated plasma constituent (as shown in FIG. 50) ensures that all of the plasma exits the spinning membrane separator 26 via line L24 as a filtered plasma product, thus increasing the volume of collected plasma.

The valve V6 associated with valve station C6 may be selectively opened to allow fluid flow through line L9, L21, and L22 and into the return bag F6. This may be advantageous if the controller 18 determines that a sufficient amount of plasma has been collected and that further plasma may be conveyed to a recipient.

As for the red blood cells, they flow out of the centrifugal separation chamber 36 via line L11. There is no pump associated with line L11, so instead the flow rate at which the red blood cells exit the centrifugal separation chamber 36 is equal to the difference between the flow rates of the centrifuge pump P3 and plasma pump P4. Valve V4 associated with valve station C4 and valve V8 associated with valve station C8 are closed to prevent fluid flow through associated lines L14 and L16 (respectively), while valve V5 associated with valve station C5 is open to direct the flow of red blood cells from line L11 through lines L13 and L12. As described above, valve V2 associated with valve station C2 and valve V6 associated with valve station C6 are closed, thereby directing the red blood cells through lines L21 and L22 and into the return bag F6.

As described above, the plasma-only draw phase may continue until the amount of blood drawn from the blood source reaches a target amount or the in-process bag F3 is filled to a particular level (as determined by a weight scale from which the in-process bag F3 is hung) or until some other condition is satisfied.

c. Return Phase

When the system transitions to the return phase (FIG. 51), the anticoagulant pump P1 will stop drawing anticoagulant from the anticoagulant bag F1. The valve V10 associated with valve station C10 will close to prevent fluid flow through line L3, and the valve V11 associated with valve station C11 is opened to allow fluid flow through line L19. The valve V2 associated with valve station C2 also opens to allow flow through line L15, while the valve V1 associated with valve station C1 closes to prevent flow through line L5.

With the valves so situated, the source pump P2 will reverse direction to allow the contents of the return bag F6 (typically red blood cells) to be conveyed to a recipient (which may be the same blood source) via the same needle used to draw blood into the fluid flow circuit 12c. The return fluid is pumped through lines L22 and L15, the valve station C2 associated with open valve V2, line L4, the sensor station S1 associated with pressure sensor A1, line L19, a return line filter 58, air detector M3, the valve station C11 associated with open valve V11, and line L1 on its way to the recipient. Saline or another replacement fluid may be drawn from the saline bag F2 via line L20 by the source pump P2 to a junction, where it mixes with fluid being conveyed to the recipient, although it may be more typical for replacement fluid to not be conveyed to the recipient until plasma collection is complete.

While fluid is being conveyed to the recipient, the blood in the in-process bag F3 acts as the blood supply for the centrifugal separation chamber 36. When the system transitions to the return phase, the centrifuge pump P3 remains unchanged and separation continues in the same manner as described for the plasma-only draw phase (i.e., with blood being separated into a plasma constituent and red blood cells, the red blood cells flowing out of the centrifugal separation chamber 36, and filtered plasma being collected in the plasma bag F8) until the in-process bag F3 is emptied. Therefore, the system components downstream from the centrifuge pump P3 are "blinded" as to whether the system is in the plasma-only draw phase or the return phase.

Figure 51:
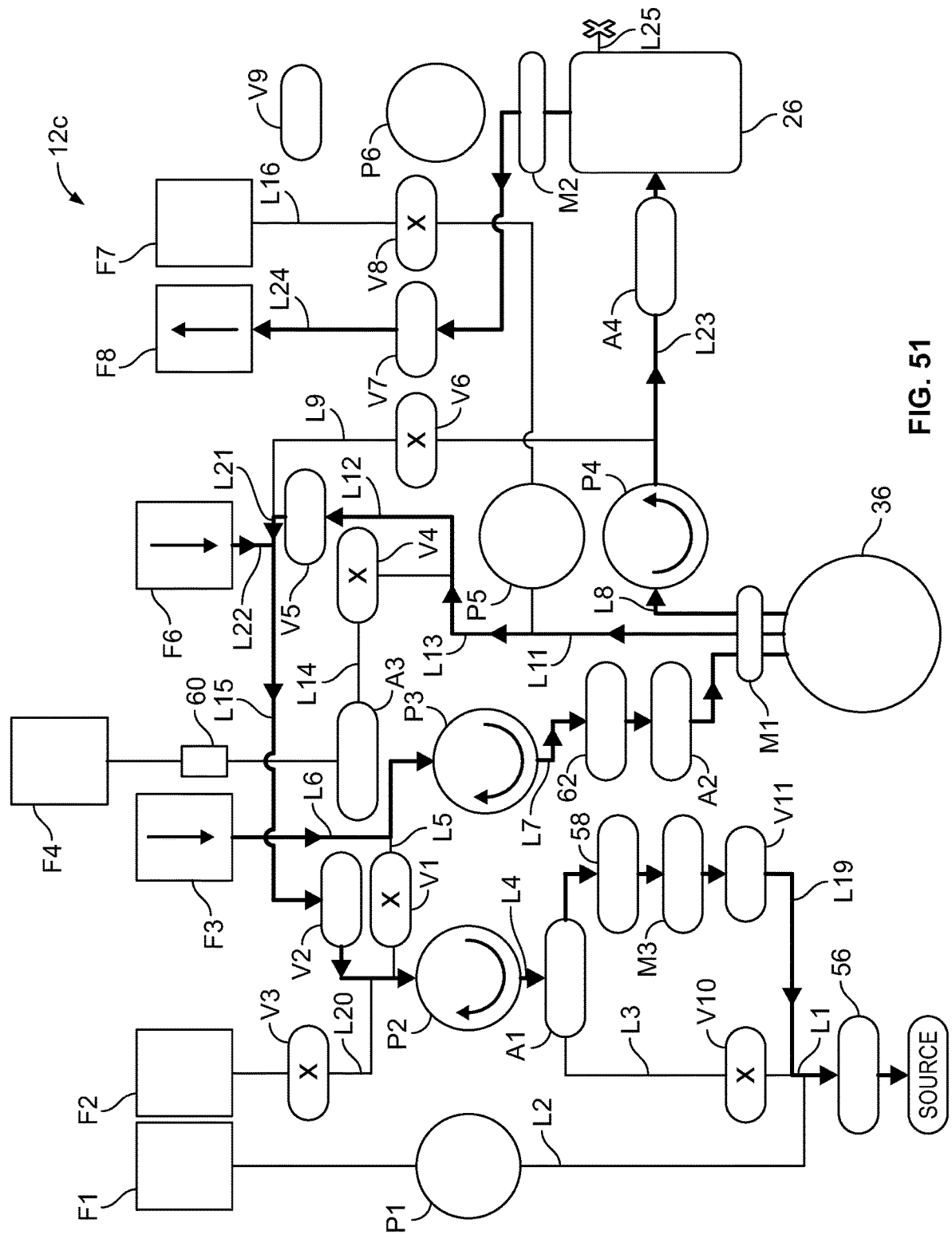

As shown in FIG. 51, due to the valve V2 associated with valve station C2 being open, the red blood cells will flow into and through lines L21 and L15 for conveyance to the recipient, along with return fluid from the return bag F6. It will be seen that the red blood cells are conveyed toward the return bag F6 at the same time that the contents of the return bag F6 are being conveyed to the recipient. The rate at which the source pump P2 operates may be greater than the rate at which the red blood cells are conveyed toward the return bag F6 to allow the return bag F6 to empty during the return phase, even as separation continues. Once the return bag F6 is empty, the system may transition back to the plasma-only draw phase (FIG. 50) and subsequently alternate between the plasma-only draw phase and return phase until enough plasma has been collected to begin red blood cell collection.

d. Draw Phase—Red Blood Cell and Plasma Collection

Figure 52:
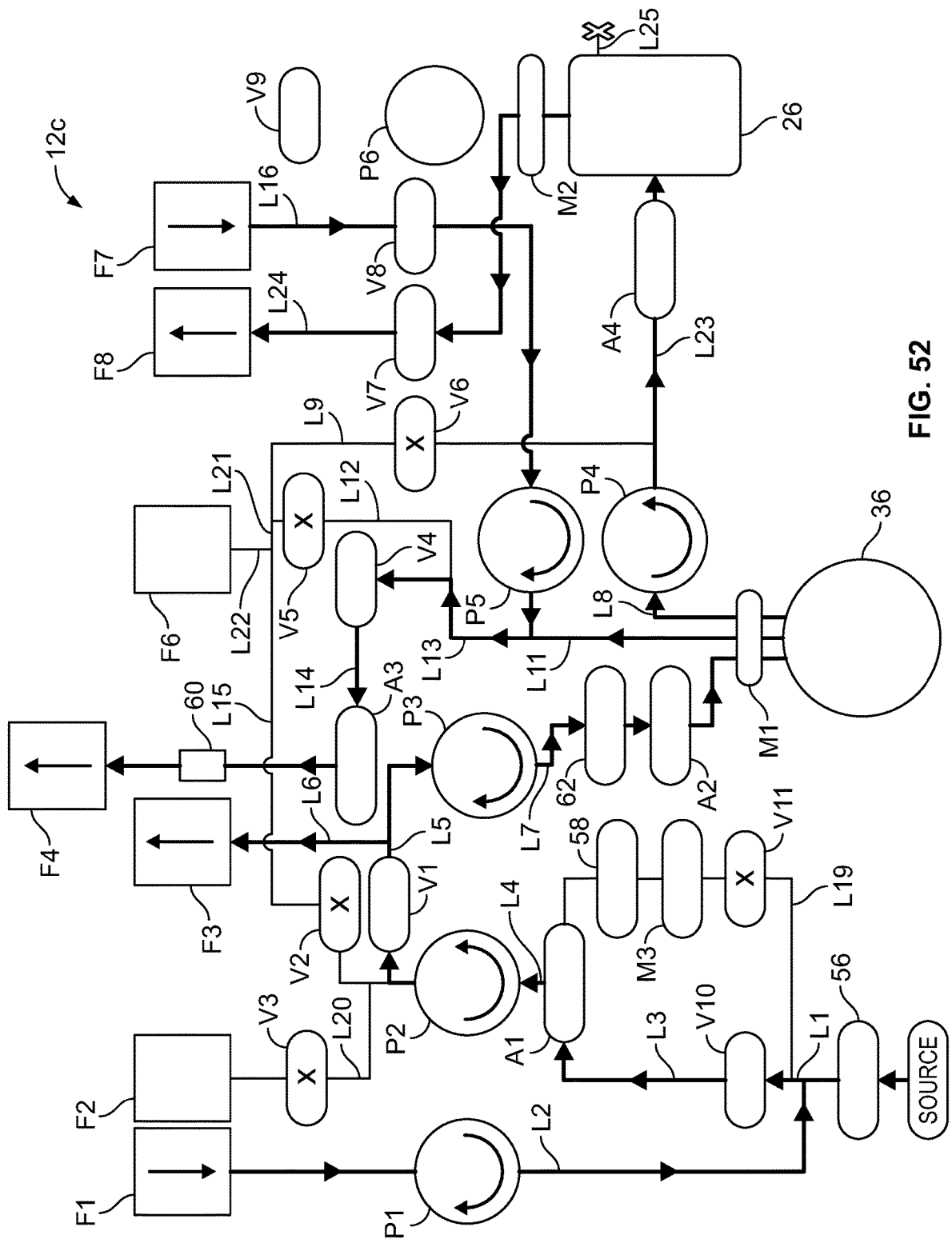

Once the plasma collection volume in plasma bag F8 is within a specific amount of the target (as explained above), the system will transition into a draw phase during which both plasma and red blood cells are collected, as shown in FIG. 52. This is the last draw phase of the procedure and will collect the red blood cell product and the remaining plasma volume. This draw phase is the same as the plasma-only draw phase until the red blood cells exit the centrifugal separation chamber 36. In this phase, the valve V5 associated with valve station C5 is closed to prevent flow through line L12 (to the return bag F6) and the valve V4 associated with valve station C4 is opened to allow the separated red blood cells to flow through line L14 toward the leukocyte removal filter 60. Pressure sensor A3 may interact with sensor station S3 of the cassette 48 to monitor the pressure of the leukocyte removal filter 60. The valve V5 associated with valve station C5 may be selectively opened to allow fluid flow through lines L12, L21, and L22 and into the return bag F6. This may be advantageous if the controller 18 determines that sufficient red blood cells have been collected and that further red blood cells may be conveyed to a recipient.

Prior to the red blood cells reaching the leukocyte removal filter 60, they may be mixed with an additive solution, such as Adsol. The additive solution may be drawn out of the additive bag F7 via line L16 (with the valve V8 associated with valve station C8 open) under action of the additive pump P5. The additive pump P5 conveys additive solution through line L16 and open valve station C8 to a junction where it is mixed with the red blood cells flowing through line L11. The additive pump P5 may operate at a rate that is based on the hematocrit of the blood entering the centrifugal separation chamber 36 (which rate may be calculated using Equation 2, for example), with additive solution being added to the red blood cells at a rate configured to produce a mixture having a predetermined or preselected hematocrit (which may be in a range of approximately 55% to approximately 75% in one exemplary embodiment and in a range of approximately 60% to approximately 65% in another exemplary embodiment).

The mixture of red blood cells and additive solution is conveyed through line L14 and the leukocyte removal filter 60, which removes the majority of the platelets and white blood cells from the mixture. The leukoreduced red blood cells are conveyed from the leukocyte removal filter 60 to the red blood cell bag F4.

As in the plasma-only draw phase, the plasma constituent is pumped out of the centrifugal separation chamber 36 under action of the plasma pump P4 and flows through the spinning membrane separator 26 and into the plasma bag F8 as a filtered plasma product.

e. Final Phase

At a point during the draw phase of FIG. 52, the source pump P2 will have pumped enough blood into the fluid flow circuit 12c to allow for the targeted red blood cell and plasma product volumes to be reached. However, a specific volume of blood in the in-process bag F3 will have yet to be processed. At this point, the source pump P2 will stop drawing blood from the blood source and the valve V10 associated with valve station C10 will close to prevent fluid flow through line L3. The blood remaining in the in-process bag F3 will then be processed by the centrifugal separation chamber 36 to complete the procedure, as shown in FIG. 53.

Figure 53:
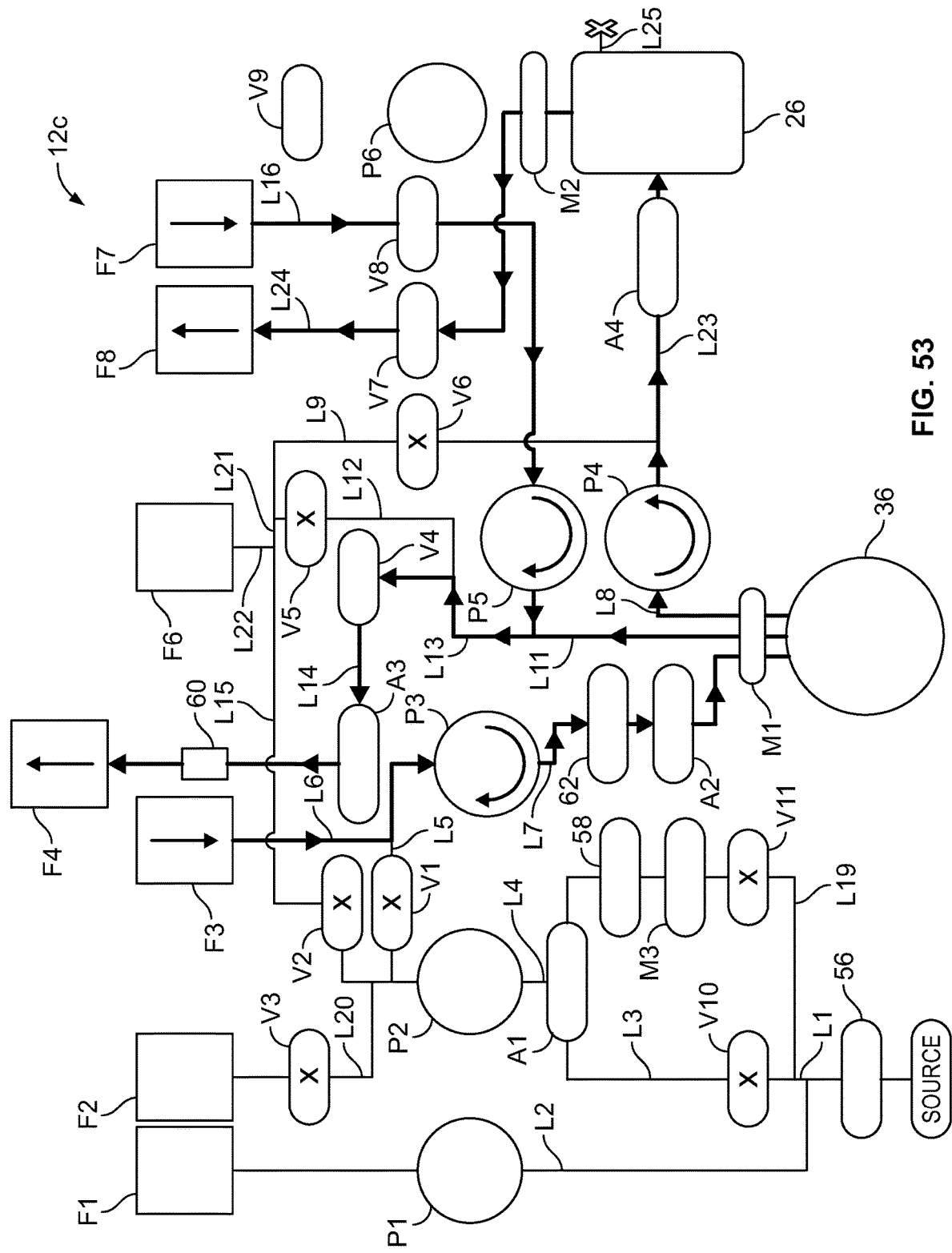
Figure 54:
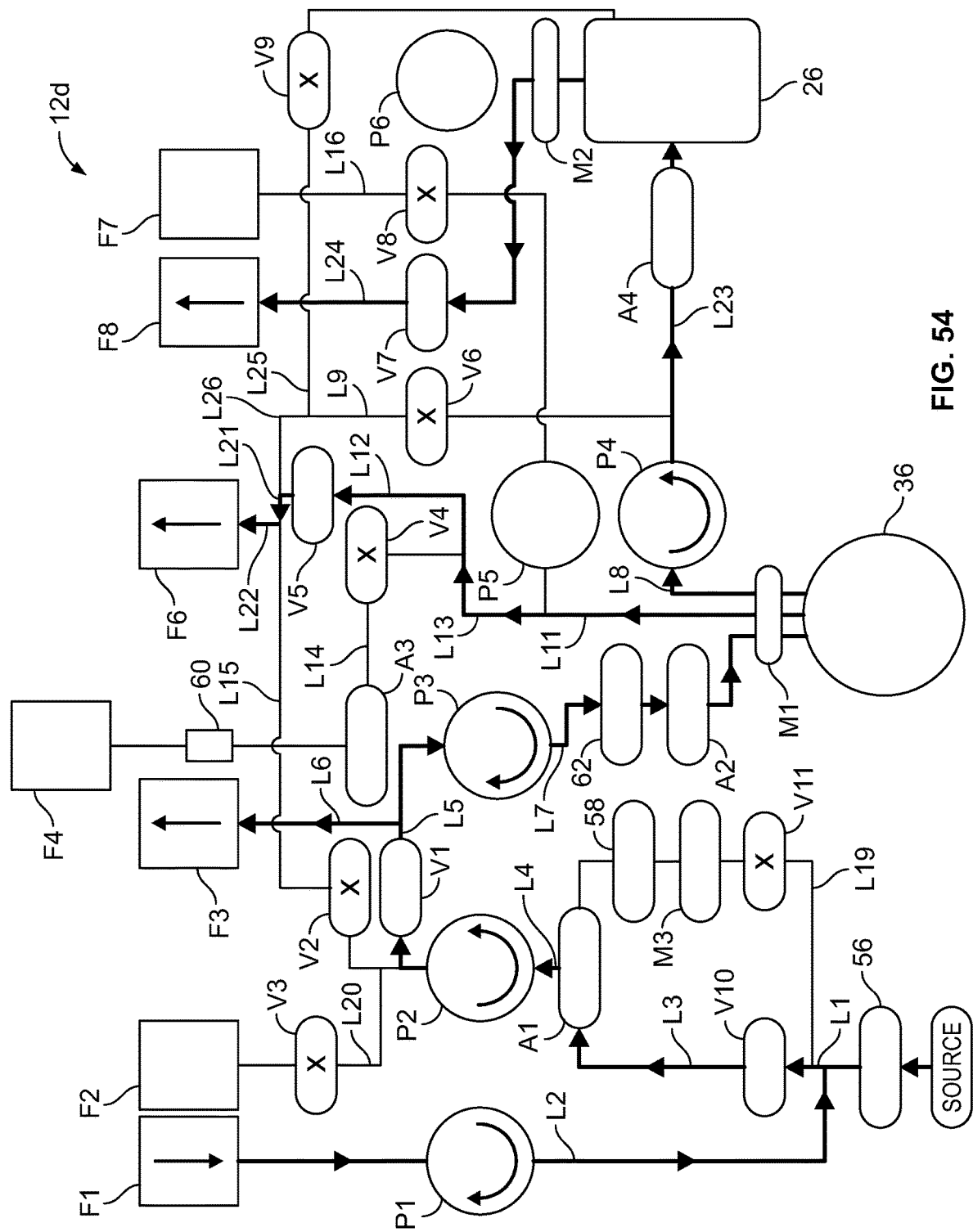
Figure 55:
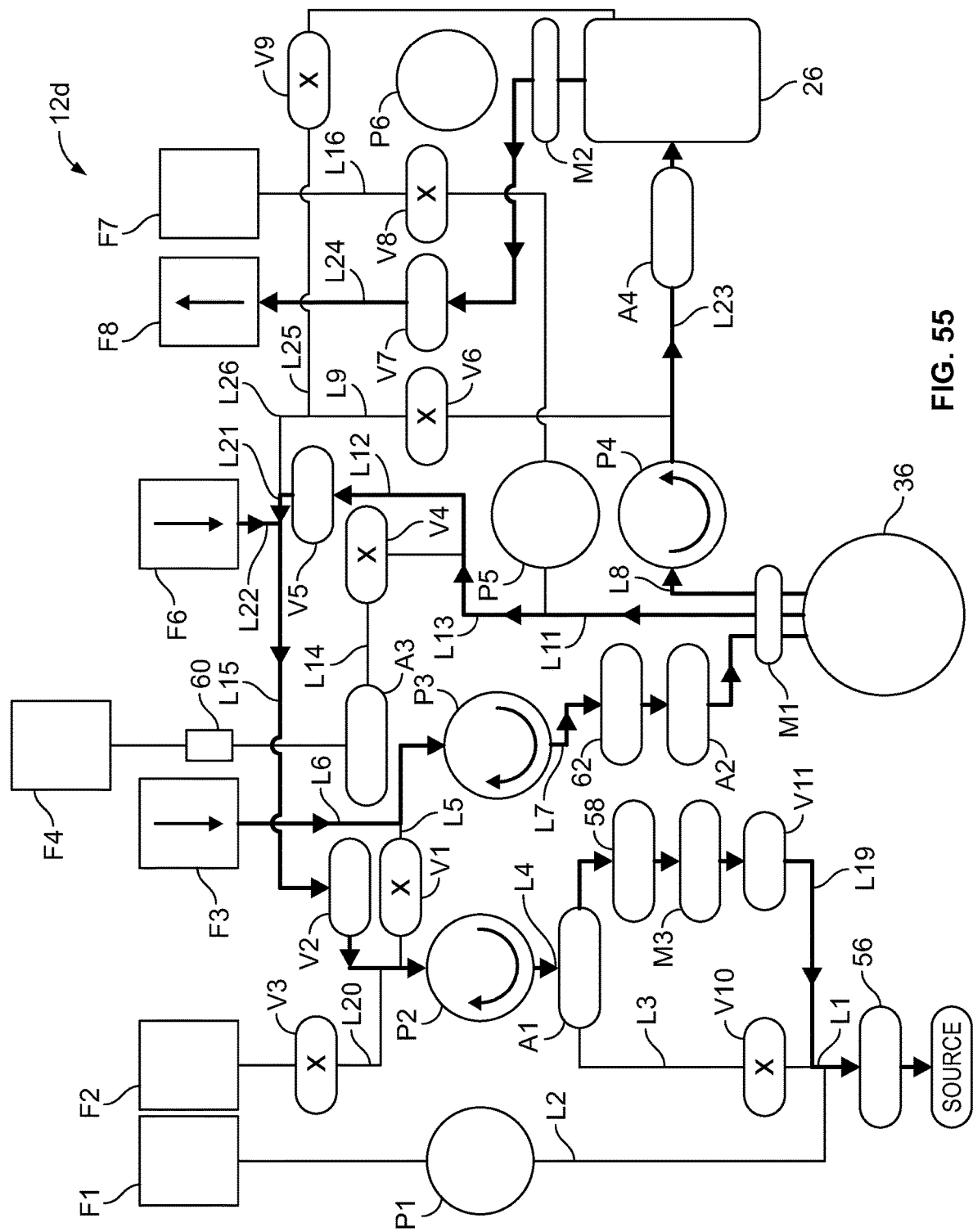

With the valve stations situated as shown in FIG. 53, the blood in the in-process bag F3 acts as the blood supply for the centrifugal separation chamber 36. Other than the blood entering the centrifugal separation chamber 36 from a different origin, this phase proceeds in the same manner as described for the final draw phase (i.e., with blood being separated into a plasma constituent and red blood cells, the plasma flowing to the plasma bag F8 as a filtered product, and the red blood cells being diluted, filtered, and collected as leukoreduced red blood cells) until the in-process bag F3 is emptied. Upon emptying the in-process bag F3, the targeted amounts of red blood cell product and plasma product should be contained within the respective collection containers F4 and F8, which may be confirmed by the weight scales from which the containers F4 and F8 may be hung during the procedure.

3. Filtered Plasma Product Fluid Flow Circuit and Procedure, with Cell Return a. Fluid Flow Circuit

FIG. 2D is a schematic view of a fluid flow circuit 12d that is a variation of the fluid flow circuit 12c of FIG. 2C. Due to similarities between the fluid flow circuit 12d of FIG. 2D and the fluid flow circuit 12c of FIG. 2C, similarly configured fluid lines will be identified with the same reference labels in FIGS. 2C and 2D, while lines that are differently configured and/or not employed in the fluid flow circuit 12*c* of FIG. 2C will be identified in FIG. 2D with different reference labels.

While FIGS. 50-53 illustrate a process in which a separated plasma constituent is "dead end" filtered, without cellular blood components ever being removed from the spinning membrane separator 26, the fluid flow circuit 12*d* of FIG. 2D is configured to allow for "dead end" filtration followed by the removal of cellular blood components from the spinning membrane separator 26 at the end of a procedure. In particular, the fluid flow circuit 12*d* differs from the fluid flow circuit 12*d* in that line L25 is not sealed or otherwise closed to flow, but rather includes an associated valve V9 that may be selectively opened and closed to allow fluid flow through an associated valve station C9 and, hence, through line L25. As will be described, valve V9 remains closed during the procedure, with the valve V9 only opening at the end of the procedure to allow the cellular blood components to be flushed from the spinning membrane separator 26 via line L25, to be conveyed to a recipient.

b. Draw Phase—Plasma Collection Only

A plasma-only draw phase (FIG. 54) proceeds as described above with regard to the plasma-only draw phase (FIG. 50) of the fluid flow circuit 12*c* of FIG. 2C. As line L25 is not sealed or otherwise closed to fluid flow, valve V9 associated with valve station C9 is closed to prevent fluid flow through line L25, thus retaining cellular blood components filtered out of the separated plasma constituent within the spinning membrane separator 26.

As described above, the plasma-only draw phase may continue until the amount of blood drawn from the blood source reaches a target amount or the in-process bag F3 is filled to a particular level (as determined by a weight scale from which the in-process bag F3 is hung) or until some other condition is satisfied.

c. Return Phase

The system transitions into a return phase (FIG. 55) as described above with regard to the return phase (FIG. 51) of the fluid flow circuit 12*c* of FIG. 2C. As in the plasma-only draw phase of FIG. 54, the valve V9 associated with valve station C9 remains closed to prevent fluid flow through line L25, thus retaining cellular blood components filtered out of the separated plasma constituent within the spinning membrane separator 26.

Once the return bag F6 is empty, the system may transition back to the plasma-only draw phase (FIG. 54) and subsequently alternate between the plasma-only draw phase and return phase until enough plasma has been collected to begin red blood cell collection.

d. Draw Phase—Red Blood Cell and Plasma Collection

Figure 56:
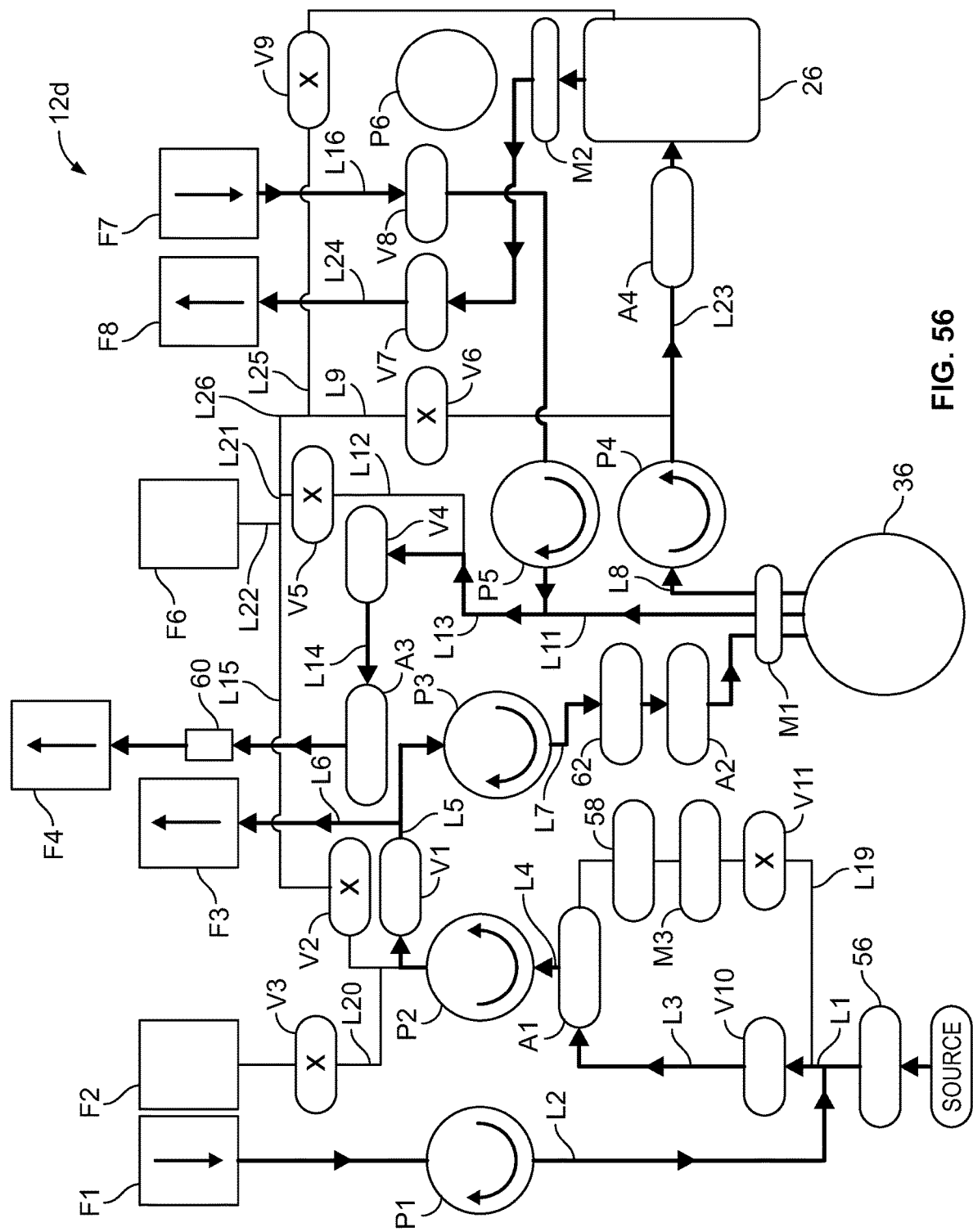

Once the plasma collection volume in plasma bag F8 is within a specific amount of the target (as explained above), the system will transition into a draw phase during which both plasma and red blood cells are collected, as shown in FIG. 56. This draw phase proceeds as described above with regard to the draw phase of the fluid flow circuit 12*c* of FIG. 2C in which both plasma and red blood cells are collected (FIG. 52). As in the preceding phases of FIGS. 54 and 55, the valve V9 associated with valve station C9 remains closed to prevent fluid flow through line L25, thus retaining cellular blood components filtered out of the separated plasma constituent within the spinning membrane separator 26.

e. Final Phase with Plasma Collection

Figure 57:
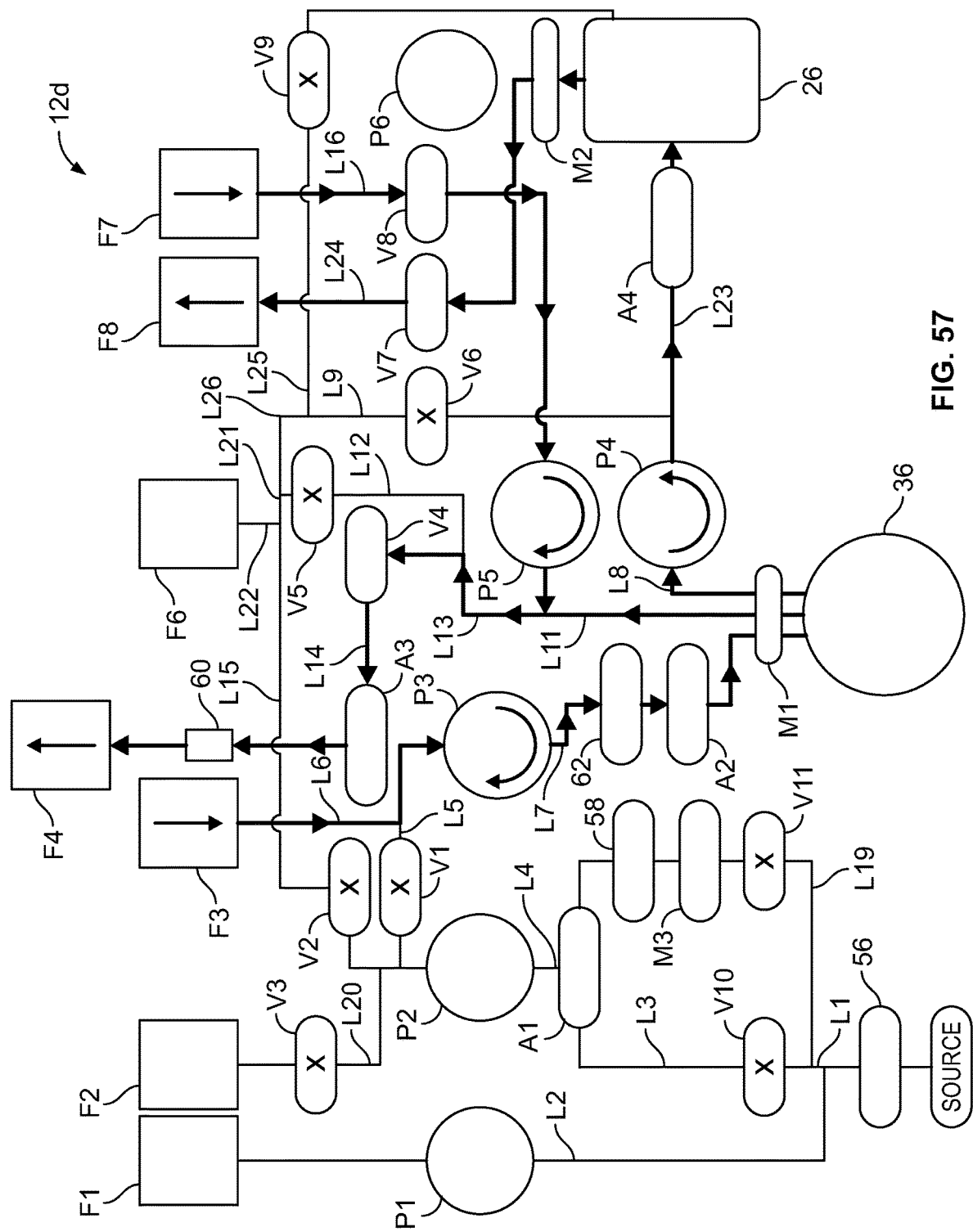

At a point during the draw phase of FIG. 56, the source pump P2 will have pumped enough blood into the fluid flow circuit 12*c* to allow for the targeted red blood cell and plasma product volumes to be reached. However, a specific volume of blood in the in-process bag F3 will have yet to be processed. At this point, the source pump P2 will stop drawing blood from the blood source and the valve V10 associated with valve station C10 will close to prevent fluid flow through line L3. The blood remaining in the in-process bag F3 will then be processed by the centrifugal separation chamber 36 to complete plasma collection, as shown in FIG. 57.

This "final phase" proceeds as described above with regard to the "final phase" (FIG. 53) of the fluid flow circuit 12*c* of FIG. 2C. As in the preceding phases of FIGS. 54-56, the valve V9 associated with valve station C9 remains closed to prevent fluid flow through line L25, thus retaining cellular blood components filtered out of the separated plasma constituent within the spinning membrane separator 26.

f. Flush Phase

Figure 58:
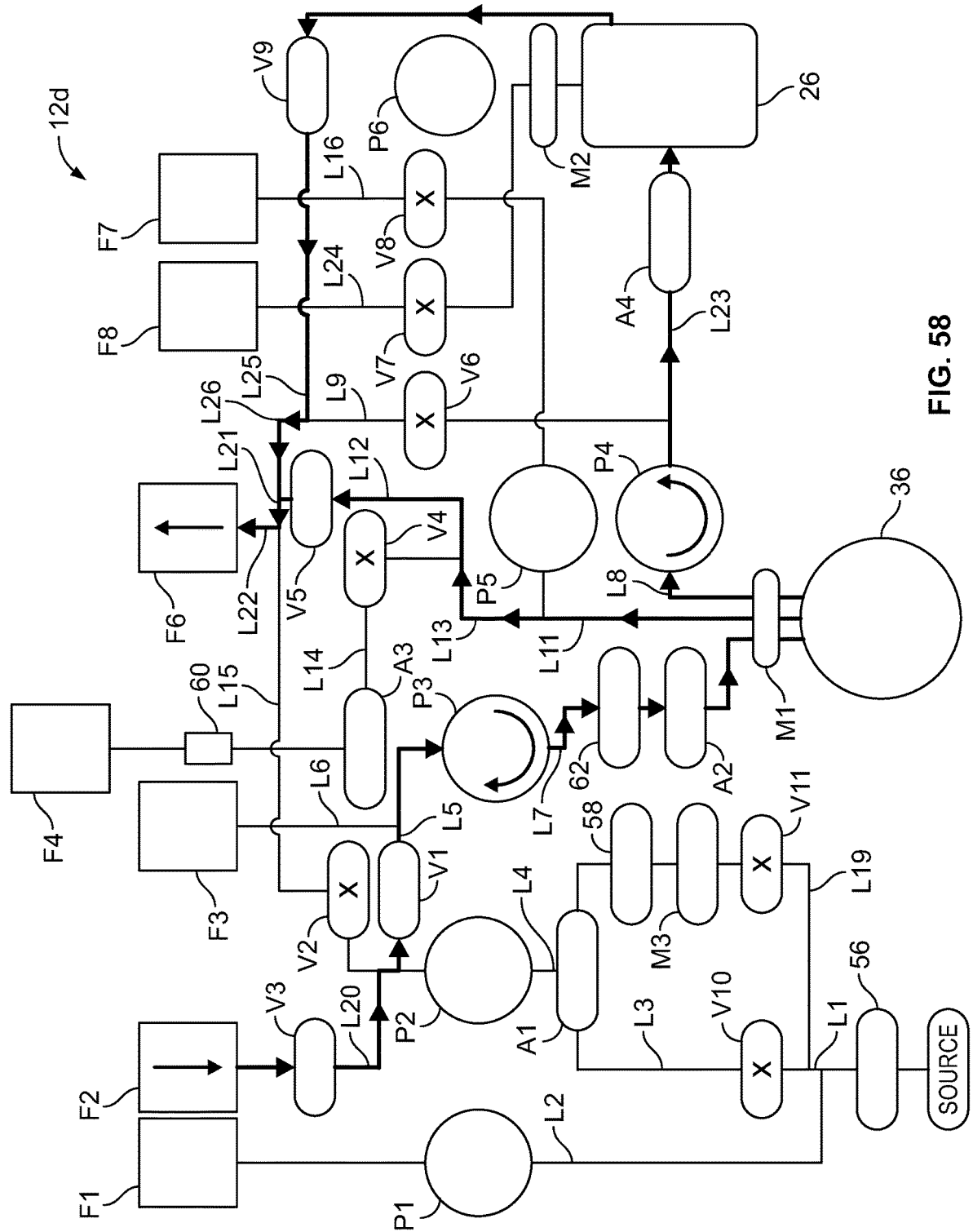
Figure 59:
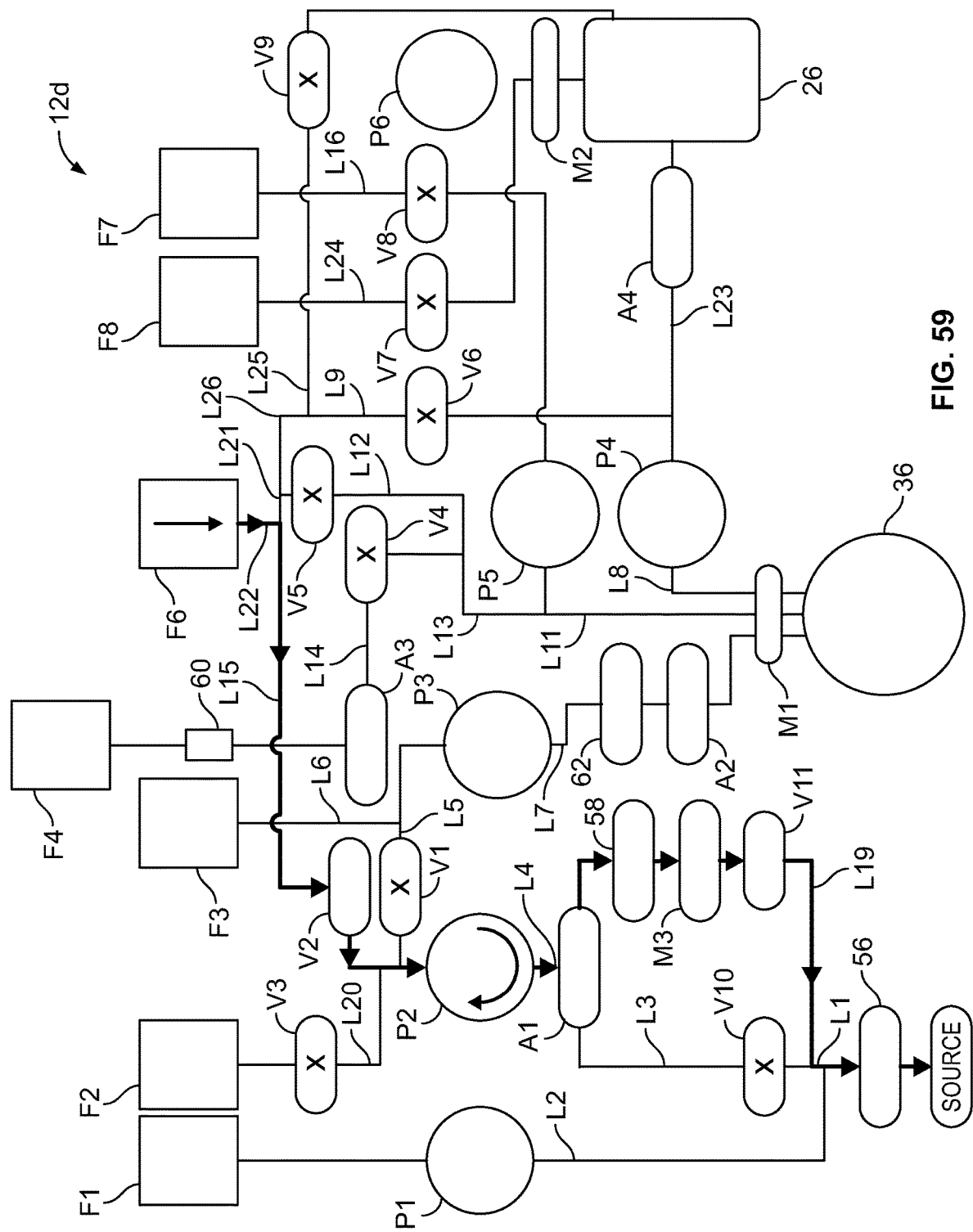

When plasma collection has been completed, the system transitions to a flush phase, which is shown in FIG. 58. In this phase, the valves V1, V3, V5, and V9 associated with valve stations C1, C3, C5, and C9 (respectively) are moved from being closed to being open, while the valves V4, V7, and V8 associated with valve stations C4, C7, and C8 (respectively) are moved from being open to being closed.

With the valve stations situated as shown in FIG. 58, saline from the saline bag F2 is drawn into the centrifugal separation chamber 36 by the centrifuge pump P3, with the saline flowing through lines L20, L5, and L7. As shown in FIG. 58, the saline will push blood components remaining in the centrifugal separation chamber 36 out of the centrifugal separation chamber 36 via line L11, with the blood components flowing through lines L13, L12, L21, and L22, before flowing into the return bag F6.

The saline exits the centrifugal separation chamber 36 via line L8 and flows into the spinning membrane separator 26 via line L23. With the valve V7 associated with valve station C7 being closed and the valve V9 associated with valve station C9 being open, the saline flushes the cellular blood components out of the spinning membrane separator 26 via line L25. The mixture of cellular blood components and saline travels through line L25 to a junction. The valve V6 associated with valve station C6 is closed, thus directing the mixture into line L26 and to another junction. The valve V5 associated with valve station C5 is open, but the flow of flushed cellular components exiting the centrifugal separation chamber 36 and flowing through line L12 prevents the mixture flowing through line L26 from flowing into line L12. Instead, the flow of cellular blood components flushed from the spinning membrane separator 26 joins the flow of blood components flushed from the centrifugal separation chamber 36 and flows through lines L21 and L22, before flowing into the return bag F6.

While saline is described and shown in FIG. 58 as being used to flush blood components from the centrifugal separation chamber 36 and the spinning membrane separator 26, it should be understood that other fluids (e.g., air or some other replacement fluid or separated plasma) may also or alternatively be used to flush blood components from the centrifugal separation chamber 36 and/or the spinning membrane separator 26.

g. Return of Flushed Fluid Phase

Once the blood components have been flushed from the centrifugal separation chamber 36 and the spinning membrane separator 26, the system transitions to a final return phase in which the contents of the return bag F6 are conveyed out of the fluid flow circuit 12d. This is done by closing the valves V1, V5, and V9 associated with valve stations C1, C5, and C9 (respectively) and opening the valves V2 and V11 associated with valve stations C2 and C11 (respectively). Depending on whether saline is to be conveyed out of the fluid flow circuit 12d with the contents of the return bag F6, the valve V3 associated with valve station C3 may be either closed or remain open.

Operation of the centrifuge pump P3 and the plasma pump P4 is ceased, while the source pump P2 is activated to draw the contents of the return bag F6 into line L22. The return fluid continues flowing into line L15 and through line L4 (with or without saline from the saline bag F2), flowing through the sensor station S1 associated with pressure sensor A1, a return line filter 58, air detector M3, the valve station C11 associated with open valve V11, and lines L19 and L1 on its way to the recipient (which may be the blood source) as a return fluid.

While the amount of cellular blood components filtered from the plasma constituent in the spinning membrane separator 26 will typically be relatively low (due to the plasma constituent exiting the centrifugal separation chamber 36 tending to have a low cell content), the fluid flow circuit 12d of FIG. 2D thus allows for those cellular blood components to be conveyed to a recipient (such as the blood source) instead of being discarded as a waste product, as is the case in a procedure using the fluid flow circuit 12c of FIG. 2C.

C. Plasma Collection

According to one aspect of the present disclosure, the blood separation device 10 may be used to separate and collect plasma from blood. A blood separation device 10 according to the present disclosure may be used in combination with a fluid flow circuit 12 having a single blood access device (e.g., a single needle that draws blood from and returns a separated blood component to the same location) or two blood access devices (e.g., one needle that draws blood from a source and a second needle that flows a separated blood component to the same source or to a different recipient) and, in either case, may produce a filtered or unfiltered plasma product. Exemplary fluid flow circuits and procedures will be described for each arrangement.

1. Single Needle Fluid Flow Circuit and Procedure—Unfiltered Plasma Product a. Fluid Flow Circuit

FIG. 2E is a schematic view of an exemplary fluid flow circuit 12e having a single blood access device (e.g., a needle) for separating and collecting plasma from blood. The fluid flow circuit 12e includes a cassette 48 of the type described above and illustrated in FIG. 4, which connects the various components of the fluid flow circuit 12e. The various connections amongst the components of the fluid flow circuit 12e are shown in FIG. 2E, which also shows the fluid flow circuit 12e mounted to the blood separation device 10. Due to similarities between the fluid flow circuit 12e of FIG. 2E and the fluid flow circuit 12b of FIG. 2B, similarly configured fluid lines will be identified with the same reference labels in FIGS. 2B and 2E, while lines that are differently configured and/or not employed in the fluid flow circuit 12b of FIG. 2B will be identified in FIG. 2E with different reference labels.

Components of the fluid flow circuit 12e interact with many of the components of the blood separation device 10, as will be described, but there are selected components of the blood separation device 10 that are not used in separating and collecting plasma using the fluid flow circuit 12e of FIG. 2E. Most notably, the spinning membrane separator drive unit 14 is not used, but only the centrifugal separator 16. There are also selected valves V4, V8, and V9, two pumps P5 and P6, two pressure sensors A3 and A4, and a spinner outlet sensor M2 of the blood separation device 10 that are not used in the procedure described herein.

b. Draw Phase

In a first phase (FIG. 60), blood is drawn into the fluid flow circuit 12e from a blood source. If the blood source is a donor, then blood may be drawn into the fluid flow circuit 12e through a single needle that is connected to the cassette 48 by line L1. The line L1 may include a manual clamp 56 that may initially be in a closed position to prevent fluid flow through the line L1. When processing is to begin, an operator may move the manual clamp 56 from its closed position to an open position to allow fluid flow through the line L1.

The blood is drawn into the line L1 by the source pump P2 of the blood separation device 10. Anticoagulant from the anticoagulant bag F1 may be drawn through line L2 under action of the anticoagulant pump P1 and added to the blood at a junction of lines L1 and L2. Valve V10 associated with valve station C10 is open to allow blood to flow through line L3 and a sensor station S1 associated with pressure sensor A1. If the blood source is a living body (e.g., a donor), the pressure sensor A1 may communicate with the controller 18 to monitor the pressure within the vein of the blood source.

The cassette 48 includes two valve stations C1 and C2 downstream of the source pump P2 and line L4, with the valve V2 associated with one of the valve stations C2 being closed and the valve V1 associated with the other valve station C1 being open. The blood flows through the line L5 associated with the open valve V5 to a junction, where a portion of the blood is directed through line L6 to the in-process bag F3, with the remainder being directed through line L7 toward the centrifugal separation chamber 36. The centrifuge pump P3 is associated with line L7 and controls the amount of blood that is directed to the centrifugal separation chamber 36 instead of the in-process bag F3. In particular, the flow rate of the source pump P2 is greater than the flow rate of the centrifuge pump P3, with the difference therebetween being equal to the flow rate of blood into the in-process bag F3. The flow rates may be selected such that the in-process bag F3 is partially or entirely filled with blood at the end of the draw phase.

The blood flowing through line L7 toward the centrifugal separation chamber 36 passes through an air trap 62, a sensor station S2 associated with pressure sensor A2 (which monitors the pressure of the centrifugal separation chamber 36), and a centrifugal separator sensor M1. The centrifugal separator sensor M1 may detect the hematocrit of the blood entering the centrifugal separation chamber 36, for example.

The centrifugal separator 16 of the blood separation device 10 manipulates the centrifugal separation chamber 36 to separate red blood cells from a plasma constituent, which may be platelet-rich plasma or (more preferably) platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and a plasma constituent (as described above).

The plasma constituent is pumped out of the centrifugal separation chamber 36 via line L8 under action of the plasma pump P4. Valve V6 is closed to prevent fluid flow through associated valve station C6 and line L9, while valve V7 is open to allow fluid flow through associated valve station C7 and line L10, thereby directing the flow of the plasma constituent through line L10 and into the plasma bag F8. The valve V6 associated with valve station C6 may be selectively opened to allow fluid flow through line L9, L21, and L22 and into the return bag F6. This may be advantageous if the controller 18 determines that a sufficient amount of plasma has been collected and that further plasma may be conveyed to a recipient.

The red blood cells flow out of the centrifugal separation chamber 36 via line L11. There is no pump associated with line L11, so instead the flow rate at which the red blood cells exit the centrifugal separation chamber 36 is equal to the difference between the flow rates of the centrifuge pump P3 and plasma pump P4. Valve V6 associated with valve station C6 and valve V2 associated with valve station C2 are closed to prevent fluid flow through associated lines L9 and L15 (respectively), while valve V5 associated with valve station C5 is open to direct the flow of red blood cells from line L11 through lines L21 and L22 and into the return bag F6.

The draw phase may continue until the amount of blood drawn from the blood source reaches a target amount or the in-process bag F3 is filled to a particular level or until some other condition is satisfied.

c. Return Phase

When the system transitions to the return phase of FIG. 61, the anticoagulant pump P1 will stop drawing anticoagulant from the anticoagulant bag F1. The valve V10 associated with valve station C10 closes to prevent fluid flow through line L3 and the valve V11 associated with valve station C11 is opened to allow fluid flow through line L19. The valve V2 associated with valve station C2 opens to allow flow through line L15, while the valve V1 associated with valve station C1 closes to prevent flow through line L5.

With the valves so situated, the source pump P2 will reverse direction to allow the contents of the return bag F6 (typically red blood cells) to be conveyed to a recipient (which may be the same blood source) via the same needle used to draw blood into the fluid flow circuit 12e. The return fluid is pumped through line L22 and L15, the valve station C2 associated with open valve V2, line L4, the sensor station S1 associated with pressure sensor A1, line L19, a return line filter 58, air detector M3, the valve station C11 associated with open valve V11, and line L1 on its way to the recipient. Saline or another replacement fluid may be drawn from the saline bag F2 via line L20 by the source pump P2 to a junction, where it mixes with fluid being conveyed to the recipient, although it may be more typical for replacement fluid to not be conveyed to the recipient until plasma collection is complete.

While fluid is being conveyed to the recipient, the blood in the in-process bag F3 acts as the blood supply for the centrifugal separation chamber 36. When the system transitions to the return phase, the centrifuge pump P3 remains unchanged and separation continues in the same manner as described for the draw phase (i.e., with blood being separated into a plasma constituent and red blood cells, the red blood cells flowing out of the centrifugal separation chamber 36, and the plasma being collected in the plasma bag F8) until the in-process bag F3 is emptied. Therefore, the system components downstream from the centrifuge pump P3 are "blinded" as to whether the system is in a draw or return phase.

As shown in FIG. 61, due to the valve V2 associated with the valve station C2 being open, the red blood cells will flow into and through lines L21 and L15 for conveyance to the recipient, along with return fluid from the return bag F6. It will be seen that the red blood cells are conveyed toward the return bag F6 at the same time that the contents of the return bag F6 are being conveyed to the recipient. The rate at which the source pump P2 operates may be greater than the rate at which the red blood cells are conveyed toward the return bag F6 to allow the return bag F6 to empty during the return phase, even as separation continues. Once the return bag F6 is empty, the system may transition back to the draw phase (FIG. 60) and subsequently alternate between the draw and return phases until the target amount of plasma has been collected.

2. Single Needle Fluid Flow Circuit and Procedure—Filtered Plasma Product a. Fluid Flow Circuit FIG. 2F is a schematic view of a fluid flow circuit 12f that is a variation of the fluid flow circuit 12e of FIG. 2E. As described above, the blood separation device 10 may be used to produce leukoreduced red blood cells and an unfiltered plasma product, such as by the procedure illustrated in FIGS. 60 and 61. While the plasma product produced by such a procedure will tend to include an acceptably small amount of cellular blood components, a substantially or virtually cell-free plasma product may be produced by filtering the plasma constituent prior to collection. Such filtration may be carried out using the spinning membrane separator drive unit 14 of the blood separation device 10, along with a fluid flow circuit 12f having a spinning membrane separator 26 (as shown in FIG. 2F), which results in a plasma product having a lower cell content than is achievable by any type of centrifugation. Due to similarities between the fluid flow circuit 12f of FIG. 2F and the fluid flow circuit 12c of FIG. 2C, similarly configured fluid lines will be identified with the same reference labels in FIGS. 2C and 2F, while lines that are differently configured and/or not employed in the fluid flow circuit 12c of FIG. 2C will be identified in FIG. 2F with different reference labels.

Components of the fluid flow circuit 12f interact with many of the components of the blood separation device 10, as will be described, but there are selected components of the blood separation device 10 that are not used in separating and collecting filtered plasma using the fluid flow circuit 12f of FIG. 2F. In particular, selected valves V4, V8, and V9, one of the pressure sensors A3, and two of the pumps P5 and P6 of the blood separation device 10 are not used in the procedure described herein. As noted above, and in contrast to the fluid flow circuit 12e of FIG. 2E, the fluid flow circuit 12f of FIG. 2F interacts with both the centrifugal separator 16 and the spinning membrane separator drive unit 14 of the blood separation device 10.

b. Draw Phase

During a draw phase (FIG. 62), blood is drawn into the fluid flow circuit 12f from a blood source. If the blood source is a donor, then blood may be drawn into the fluid flow circuit 12f through a single needle that is connected to the cassette 48 by line L1. The line L1 may include a manual clamp 56 that may initially be in a closed position to prevent fluid flow through the line L1. When processing is to begin, an operator may move the manual clamp 56 from its closed position to an open position to allow fluid flow through the line L1.

The blood is drawn into the line L1 by the source pump P2 of the blood separation device 10. Anticoagulant may be drawn from the anticoagulant bag F1 by the anticoagulant pump P1, which conveys the anticoagulant through line L2 to a junction, where it is mixed with blood flowing through line L1 into the fluid flow circuit 12f.

In the illustrated embodiment, the valve V10 associated with valve station C10 is open to allow blood to flow through line L3 and a sensor station S1 associated with pressure sensor A1. If the blood source is a living body (e.g., a donor), the pressure sensor A1 may communicate with the controller 18 to monitor the pressure within the vein of the blood source.

The cassette 48 includes two valve stations C1 and C2 downstream of the source pump P2, with the valve V2 of one valve station C2 being closed and the valve V1 of the other valve station C1 being open. The blood flows through the line L5 associated with the open valve V1 to a junction, where a portion of the blood is directed through line L6 to the in-process bag F3 and the remainder is directed through line L7 toward the centrifugal separation chamber 36. The centrifuge pump P3 is associated with line L7 and controls the amount of blood that is directed to the centrifugal separation chamber 36 instead of the in-process bag F3. In particular, the flow rate of the source pump P2 is greater than the flow rate of the centrifuge pump P3, with the difference therebetween being equal to the flow rate of blood into the in-process bag F3. The flow rates may be selected such that the in-process bag F3 is partially or entirely filled with blood at the end of this draw phase.

The blood flowing through line L7 toward the centrifugal separation chamber 36 passes through an air trap 62, a sensor station S2 associated with pressure sensor A2 (which monitors the pressure of the centrifugal separation chamber 36), and a centrifugal separator sensor M1. The centrifugal separator sensor M1 may detect the hematocrit of the blood entering the centrifugal separation chamber 36.

The centrifugal separator 16 of the blood separation device 10 manipulates the centrifugal separation chamber 36 to separate red blood cells from a plasma constituent, which may be platelet-rich plasma or (more preferably) platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and a plasma constituent (as described above).

The plasma constituent is pumped out of the centrifugal separation chamber 36 via line L8 under action of the plasma pump P4. Valve V6 is closed to prevent fluid flow through associated valve station C6 and line L9, while valve V7 is open to direct fluid flow through line L23, a sensor station S4 associated with pressure sensor A4 (which monitors the pressure of the spinning membrane separator 26), and into the spinning membrane separator 26. As described above, the separated plasma passes through the spinning membrane separator 26, which filters out any remaining cellular blood components, resulting in substantially or virtually cell-free plasma. The filtered plasma exits the spinning membrane separator 26 via line L24, passing through spinner outlet sensor M2 (which may monitor the filtered plasma to determine one or more of its properties, such as whether the plasma is hemolytic and/or lipemic), the valve station C7 associated with valve V7, and into plasma bag F8.

While the filtered plasma flows out of the spinning membrane separator 26, the cellular blood components remain in the gap 74 as a waste product that is eventually discarded with the spinning membrane separator 26 at the end of the procedure. As described above, this may be achieved by omitting an outlet associated with the gap 74 or otherwise preventing flow out of the gap 74. For example, if the spinning membrane separator 26 includes a fluid line L25 associated with the spinning membrane separator 26 for the outflow of fluid from the gap 74, that line L25 may be clamped or sealed or otherwise closed to fluid flow, as shown in FIG. 62. Flowing the cellular blood components out of the spinning membrane separator 26 would require some of the plasma to also flow out of the spinning membrane separator 26 via line L25, rather than exiting the spinning membrane separator 26 via line L24 as a filtered plasma product. Accordingly, "dead end" filtering the separated plasma constituent (as shown in FIG. 62) ensures that all of the plasma exits the spinning membrane separator 26 via line L24 as a filtered plasma product, thus increasing the volume of collected plasma.

The valve V6 associated with valve station C6 may be selectively opened to allow fluid flow through line L9, L21, and L22 and into the return bag F6. This may be advantageous if the controller 18 determines that a sufficient amount of plasma has been collected and that further plasma may be conveyed to a recipient.

As for the red blood cells, they flow out of the centrifugal separation chamber 36 via line L11. There is no pump associated with line L11, so instead the flow rate at which the red blood cells exit the centrifugal separation chamber 36 is equal to the difference between the flow rates of the centrifuge pump P3 and plasma pump P4. Valves V2 and V6 associated with valve stations C2 and C6 (respectively) are closed to prevent fluid flow through associated lines L15 and L9 (respectively), while valve V5 associated with valve station C5 is open to direct the flow of red blood cells from line L11 through lines L21 and L22 and into the return bag F6.

The draw phase may continue until the amount of blood drawn from the blood source reaches a target amount or the in-process bag F3 is filled to a particular level (as determined by a weight scale from which the in-process bag F3 is hung) or until some other condition is satisfied.

c. Return Phase

When the system transitions to the return phase (FIG. 63), the anticoagulant pump P1 will stop drawing anticoagulant from the anticoagulant bag F1. The valve V10 associated with valve station C10 will close to prevent fluid flow through line L3, and the valve V11 associated with valve station C11 is opened to allow fluid flow through line L19. The valve V2 associated with valve station C2 also opens to allow flow through line L15, while the valve V1 associated with valve station C1 closes to prevent flow through line L5.

With the valves so situated, the source pump P2 will reverse direction to allow the contents of the return bag F6 (typically red blood cells) to be conveyed to a recipient (which may be the same blood source) via the same needle used to draw blood into the fluid flow circuit 12f. The return fluid is pumped through lines L22 and L15, the valve station C2 associated with open valve V2, line L4, the sensor station S1 associated with pressure sensor A1, line L19, a return line filter 58, air detector M3, the valve station C11 associated with open valve V11, and line L1 on its way to the recipient. Saline or another replacement fluid may be drawn from the saline bag F2 via line L20 by the source pump P2 to a junction, where it mixes with fluid being conveyed to the recipient, although it may be more typical for replacement fluid to not be conveyed to the recipient until plasma collection is complete.

While fluid is being conveyed to the recipient, the blood in the in-process bag F3 acts as the blood supply for the centrifugal separation chamber 36. When the system transitions to the return phase, the centrifuge pump P3 remains unchanged and separation continues in the same manner as described for the draw phase (i.e., with blood being separated into a plasma constituent and red blood cells, the red blood cells flowing out of the centrifugal separation chamber 36, and filtered plasma being collected in the plasma bag F8) until the in-process bag F3 is emptied. Therefore, the system components downstream from the centrifuge pump P3 are "blinded" as to whether the system is in the draw phase or the return phase.

As shown in FIG. 63, due to the valve V2 associated with valve station C2 being open, the red blood cells will flow into and through lines L21 and L15 for conveyance to the recipient, along with return fluid from the return bag F6. It will be seen that the red blood cells are conveyed toward the return bag F6 at the same time that the contents of the return bag F6 are being conveyed to the recipient. The rate at which the source pump P2 operates may be greater than the rate at which the red blood cells are conveyed toward the return bag F6 to allow the return bag F6 to empty during the return phase, even as separation continues. Once the return bag F6 is empty, the system may transition back to the draw phase (FIG. 62) and subsequently alternate between the draw and return phases until a target amount of plasma has been collected.

3. Single Needle Fluid Flow Circuit and Procedure—Filtered Plasma Product, with Cell Return a. Fluid Flow Circuit

FIG. 2G is a schematic view of a fluid flow circuit 12g that is a variation of the fluid flow circuit 12f of FIG. 2F. Due to similarities between the fluid flow circuit 12g of FIG. 2G and the fluid flow circuit 12d of FIG. 2D, similarly configured fluid lines will be identified with the same reference labels in FIGS. 2D and 2G, while lines that are differently configured and/or not employed in the fluid flow circuit 12d of FIG. 2D will be identified in FIG. 2G with different reference labels.

While FIGS. 62 and 63 illustrate a process in which a separated plasma constituent is "dead end" filtered, without cellular blood components ever being removed from the spinning membrane separator 26, the fluid flow circuit 12g of FIG. 2G is configured to allow for "dead end" filtration followed by the removal of cellular blood components from the spinning membrane separator 26 at the end of a procedure. In particular, the fluid flow circuit 12g differs from the fluid flow circuit 12f in that line L25 is not sealed or otherwise closed to flow, but rather includes an associated valve V8 that may be selectively opened and closed to allow fluid flow through an associated valve station C8 and, hence, through line L25. As will be described, valve V8 remains closed during the procedure, with the valve V8 only opening at the end of the procedure to allow the cellular blood components to be flushed from the spinning membrane separator 26 via line L25, to be conveyed to a recipient.

b. Draw Phase

A draw phase (FIG. 64) proceeds as described above with regard to the draw phase (FIG. 62) of the fluid flow circuit 12f of FIG. 2F. As line L25 is not sealed or otherwise closed to fluid flow, the valve V8 associated with valve station C8 is closed to prevent fluid flow through line L25, thus retaining cellular blood components filtered out of the separated plasma constituent within the spinning membrane separator 26.

As described above, the draw phase may continue until the amount of blood drawn from the blood source reaches a target amount or the in-process bag F3 is filled to a particular level (as determined by a weight scale from which the in-process bag F3 is hung) or until some other condition is satisfied.

c. Return Phase

The system transitions into a return phase (FIG. 65) as described above with regard to the return phase (FIG. 63) of the fluid flow circuit 12f of FIG. 2F. As in the draw phase of FIG. 64, the valve V8 associated with valve station C8 remains closed to prevent fluid flow through line L25, thus retaining cellular blood components filtered out of the separated plasma constituent within the spinning membrane separator 26.

Once the return bag F6 is empty, the system may transition back to the draw phase (FIG. 64) and subsequently alternate between the draw and return phases until a target amount of plasma has been collected.

d. Flush Phase

Figure 66:
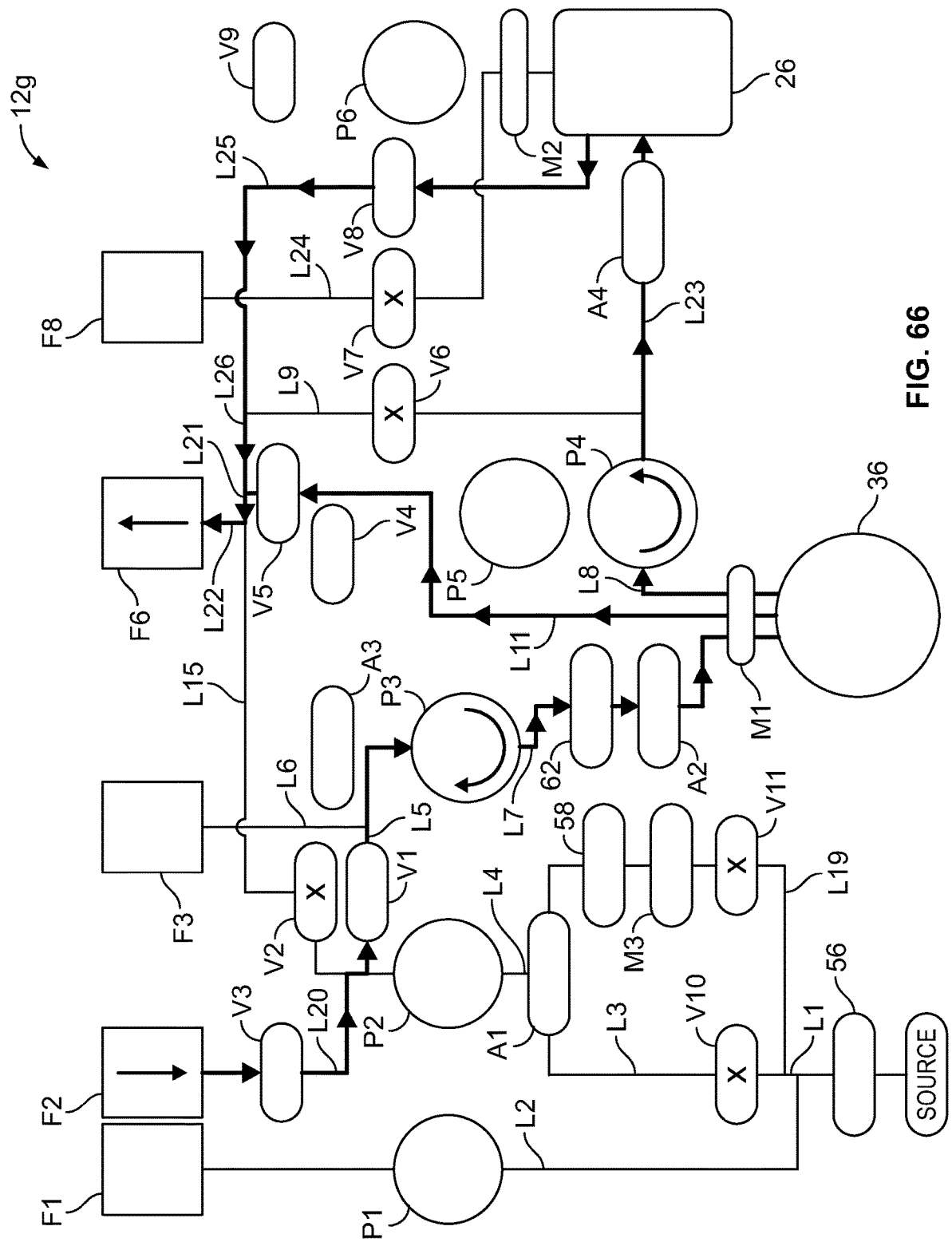
Figure 67:
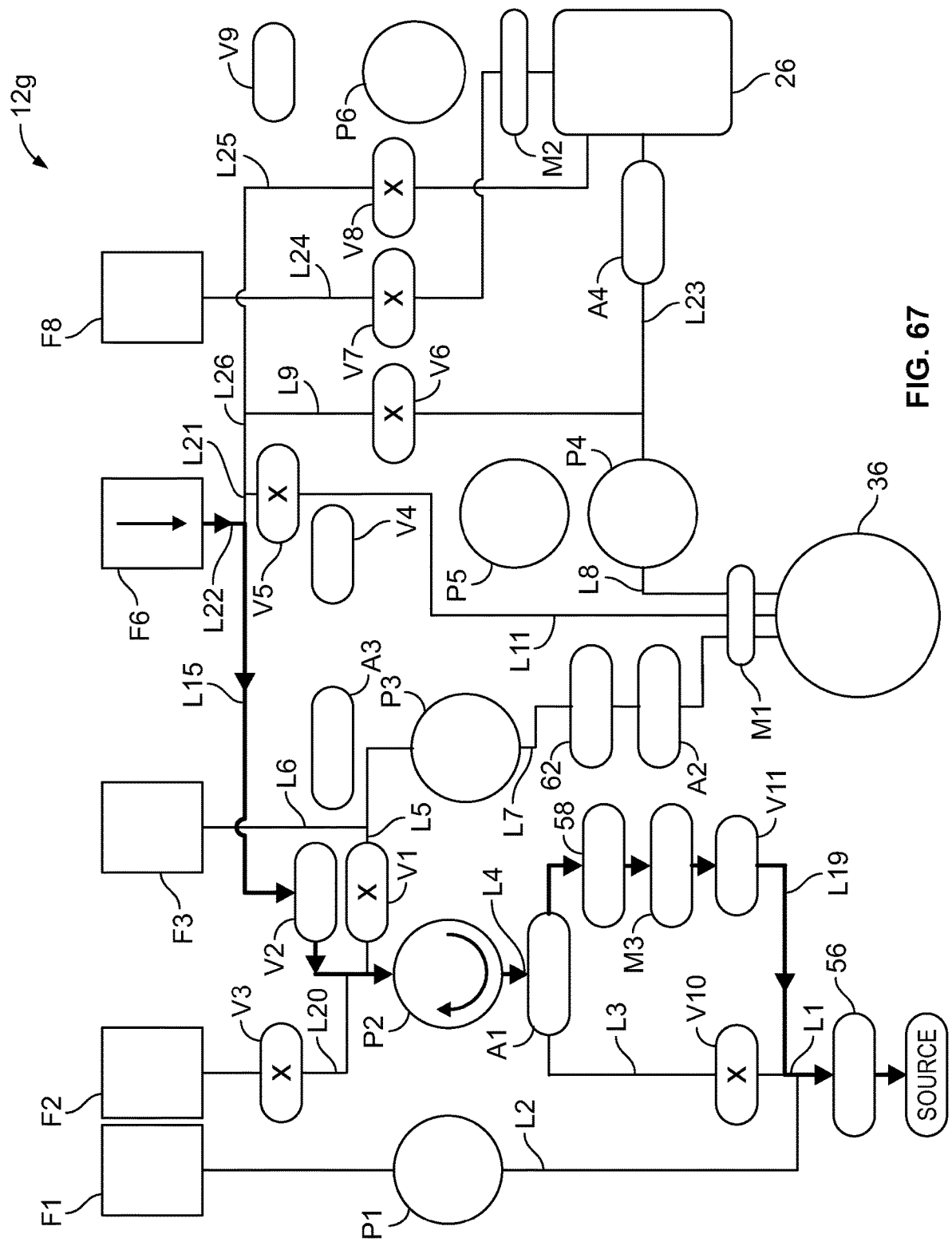

When plasma collection has been completed, the system transitions to a flush phase, which is shown in FIG. 66. In this phase, the valves V1, V3, and V8 associated with valve stations C1, C3, and C8 (respectively) are moved from being closed to being open, while the valves V2, V7, and V11 associated with valve stations C2, C7, and C11 (respectively) are moved from being open to being closed.

With the valve stations situated as shown in FIG. 66, saline from the saline bag F2 is drawn into the centrifugal separation chamber 36 by the centrifuge pump P3, with the saline flowing through lines L20, L5, and L7. As shown in FIG. 66, the saline will push blood components remaining in the centrifugal separation chamber 36 out of the centrifugal separation chamber 36 via line L11, with the blood components flowing through lines L21 and L22 before flowing into the return bag F6.

The saline exits the centrifugal separation chamber 36 via line L8 and flows into the spinning membrane separator 26 via line L23. With the valve V7 associated with valve station C7 being closed and the valve V8 associated with valve station C9 being open, the saline flushes the cellular blood components out of the spinning membrane separator 26 via line L25. The mixture of cellular blood components and saline travels through line L25 to a junction. The valve V6 associated with valve station C6 is closed, thus directing the mixture into line L26 and to another junction. The valve V5 associated with valve station C5 is open, but the flow of flushed cellular components exiting the centrifugal separation chamber 36 and flowing through line L11 prevents the mixture flowing through line L26 from flowing into line L11. Instead, the flow of cellular blood components flushed from the spinning membrane separator 26 joins the flow of blood components flushed from the centrifugal separation chamber 36 and flows through lines L21 and L22, before flowing into the return bag F6.

While saline is described and shown in FIG. 66 as being used to flush blood components from the centrifugal separation chamber 36 and the spinning membrane separator 26, it should be understood that other fluids (e.g., air or some other replacement fluid or separated plasma) may also or alternatively be used to flush blood components from the centrifugal separation chamber 36 and/or the spinning membrane separator 26.

e. Return of Flushed Fluid Phase

Once the blood components have been flushed from the centrifugal separation chamber 36 and the spinning membrane separator 26, the system transitions to a final return phase in which the contents of the return bag F6 are conveyed out of the fluid flow circuit 12g. This is done by closing the valves V1, V5, and V8 associated with valve stations C1, C5, and C8 (respectively) and opening the valves V2 and V11 associated with valve stations C2 and C11 (respectively). Depending on whether saline is to be conveyed out of the fluid flow circuit 12g with the contents of the return bag F6, the valve V3 associated with valve station C3 may be either closed or remain open.

Operation of the centrifuge pump P3 and the plasma pump P4 is ceased, while the source pump P2 is activated to draw the contents of the return bag F6 into line L22. The return fluid continues flowing into line L15 and through line L4 (with or without saline from the saline bag F2), flowing through the sensor station S1 associated with pressure sensor A1, a return line filter 58, air detector M3, the valve station C11 associated with open valve V11, and lines L19 and L1 on its way to the recipient (which may be the blood source) as a return fluid.

While the amount of cellular blood components filtered from the plasma constituent in the spinning membrane separator 26 will typically be relatively low (due to the plasma constituent exiting the centrifugal separation chamber 36 tending to have a low cell content), the fluid flow circuit 12g of FIG. 2G thus allows for those cellular blood components to be conveyed to a recipient (such as the blood source) instead of being discarded as a waste product, as is the case in a procedure using the fluid flow circuit 12f of FIG. 2F.

4. Double Needle Fluid Flow Circuit and Procedure—Unfiltered Plasma Product a. Fluid Flow Circuit FIG. 2H is a schematic view of an exemplary fluid flow circuit 12h having a pair of blood access devices (e.g., needles) for separating and collecting plasma from blood. The fluid flow circuit 12h includes a cassette 48 of the type described above and illustrated in FIG. 4, which connects the various components of the fluid flow circuit 12h. The various connections amongst the components of the fluid flow circuit 12h are shown in FIG. 2H, which also shows the fluid flow circuit 12h mounted to the blood separation device 10.

Components of the fluid flow circuit 12h interact with many of the components of the blood separation device 10, as will be described, but there are selected components of the blood separation device 10 that are not used in separating and collecting plasma using the fluid flow circuit 12h of FIG. 2H. Most notably, the spinning membrane separator drive unit 14 is not used, but only the centrifugal separator 16. There are also selected valves V4, V5, V8, and V9, two pumps P5 and P6, one pressure sensor A4, and a spinner outlet sensor M2 of the blood separation device 10 that are not used in the procedure described herein. The fluid flow circuit 12h includes a waste bag F9 and line L27 that, in the illustrated procedure of FIG. 68, is only used during the pre-processing priming phase, in which saline from the saline bag F2 is pumped through the fluid flow circuit 12H to prime it, before being conveyed to the waste bag F9 for disposal at the end of the procedure.

b. Procedure

In contrast to the separation procedure described above with respect to the fluid flow circuit 12e of FIG. 2E, the fluid flow circuit 12H of FIG. 2h allows for a single phase during which blood is simultaneous drawn and processed, with a portion of at least one separated component being conveyed to a recipient (FIG. 68). Blood is drawn into the fluid flow circuit 12h from a blood source (e.g., using a needle) via line L28. The line L28 may include a manual clamp 56 that may initially be in a closed position to prevent fluid flow through the line L28. When processing is to begin, an operator may move the manual clamp 56 from its closed position to an open position to allow fluid flow through the line L28.

The blood is drawn into the line L28 by the centrifuge pump P3, rather than pump P2 (which serves as a saline pump in this procedure). Anticoagulant from the anticoagulant bag F1 may be added to the blood via line L29 by action of the anticoagulant pump P1. The valve V10 associated with valve station C10 is open to allow flow through line L30 and through a sensor station S3 associated with pressure station A3. If the blood source is a living body (e.g., a donor), the pressure sensor A3 may communicate with the controller 18 to monitor the pressure within the vein of the blood source.

The blood flowing through line L30 passes through an air trap 62, a sensor station S2 associated with pressure sensor A2 (which monitors the pressure of the centrifugal separation chamber 36), and a centrifugal separator sensor M1, before entering the centrifugal separation chamber 36. The centrifugal separator sensor M1 may detect the hematocrit of the blood entering the centrifugal separation chamber 36, for example.

The centrifugal separator 16 of the blood separation device 10 manipulates the centrifugal separation chamber 36 to separate red blood cells from a plasma constituent, which may be platelet-rich plasma or (more preferably) platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and a plasma constituent (as described above).

The plasma constituent is pumped out of the centrifugal separation chamber 36 via line L31 under action of the plasma pump P4. Valve V6 is closed to prevent fluid flow through associated valve station C6 and line L32, while valve V7 is open to allow fluid flow through associated valve station C7 and line L33, thereby directing the flow of the plasma constituent through line L33 and into the plasma bag F8.

The red blood cells flow out of the centrifugal separation chamber 36 via line L34. There is no pump associated with line L34, so instead the flow rate at which the red blood cells exit the centrifugal separation chamber 36 is equal to the difference between the flow rates of the centrifuge pump P3 and plasma pump P4. Valve V6 associated with valve station C6 is closed to prevent fluid flow through associated line L32, thereby directing the red blood cells through line L35. The valve V2 associated with valve station C2 is closed, while the valve V1 associated with valve station C1 is open to direct the red blood cells from line L35 into line L36 and to the junction of lines L37 and L38. The saline pump P2 associated with line L37 is inactive, thus directing the red blood cells into line L38. In line L38, the red blood cells travel through the sensor station S1 associated with pressure sensor A1 (which may monitor vein pressure if the fluid recipient is a living donor), a return line filter 58, air detector M3, and the valve station C11 associated with open valve V11 on their way to the recipient (which may be the same as the blood source) via the second needle or blood access device. Saline or another replacement fluid may be drawn from the saline bag F2 via line L37 under action of the saline pump P2 to a junction, where it mixes with the red blood cells being conveyed through line L36 to the recipient, although it may be more typical for replacement fluid to not be conveyed to the recipient until plasma collection is complete.

The valve V6 associated with valve station C6 may be selectively opened, along with the valve V7 associated with valve station C7 being closed. This directs the plasma constituent flowing through line L31 to flow into line L32 (instead of line L33) and to a junction, where it mixes with the red blood cells flowing through line L34, to be conveyed out of the fluid flow circuit 12h as a return fluid. This may be advantageous if the controller 18 determines that a sufficient amount of plasma has been collected and that further plasma may be conveyed to a recipient.

This single-phase procedure continues until the target amount of plasma has been collected.

5. Double Needle Fluid Flow Circuit and Procedure—Filtered Plasma Product a. Fluid Flow Circuit

FIG. 2I is a schematic view of a fluid flow circuit 12i that is a variation of the fluid flow circuit 12h of FIG. 2H. As described above, the blood separation device 10 may be used to produce an unfiltered plasma product, such as by the procedure illustrated in FIG. 68. While the plasma product produced by such a procedure will tend to include an acceptably small amount of cellular blood components, a substantially or virtually cell-free plasma product may be produced by filtering the plasma constituent prior to collection. Such filtration may be carried out using the spinning membrane separator drive unit 14 of the blood separation device 10, along with a fluid flow circuit 12i having a spinning membrane separator 26 (as shown in FIG. 2I), which results in a plasma product having a lower cell content than is achievable by any type of centrifugation. Due to similarities between the fluid flow circuit 12i of FIG. 2I and the fluid flow circuit 12h of FIG. 2H, similarly configured fluid lines will be identified with the same reference labels in FIGS. 2H and 2I, while lines that are differently configured and/or not employed in the fluid flow circuit 12h of FIG. 2H will be identified in FIG. 2I with different reference labels.

Components of the fluid flow circuit 12i interact with many of the components of the blood separation device 10, as will be described, but there are selected components of the blood separation device 10 that are not used in separating and collecting filtered plasma using the fluid flow circuit 12i of FIG. 2I. In particular, selected valves V4, V5, V8, and V9 and two of the pumps P5 and P6 of the blood separation device 10 are not used in the procedure described herein. As noted above, and in contrast to the fluid flow circuit 12h of FIG. 2H, the fluid flow circuit 12i of FIG. 2I interacts with both the centrifugal separator 16 and the spinning membrane separator drive unit 14 of the blood separation device 10.

b. Procedure

As in the separation procedure described above with respect to the fluid flow circuit 12h of FIG. 2H, the fluid flow circuit 12i of FIG. 2I allows for a single phase during which blood is simultaneous drawn and processed, with a portion of at least one separated component being conveyed to a recipient (FIG. 69). Blood is drawn into the fluid flow circuit 12i from a blood source (e.g., using a needle) via line L28. The line L28 may include a manual clamp 56 that may initially be in a closed position to prevent fluid flow through the line L28. When processing is to begin, an operator may move the manual clamp 56 from its closed position to an open position to allow fluid flow through the line L28.

The blood is drawn into the line L28 by the centrifuge pump P3. Anticoagulant from the anticoagulant bag F1 may be added to the blood via line L29 by action of the anticoagulant pump P1. The valve V10 associated with valve station C10 is open to allow flow through line L30 and through a sensor station S3 associated with pressure station A3. If the blood source is a living body (e.g., a donor), the pressure sensor A3 may communicate with the controller 18 to monitor the pressure within the vein of the blood source.

The blood flowing through line L30 passes through an air trap 62, a sensor station S2 associated with pressure sensor A2 (which monitors the pressure of the centrifugal separation chamber 36), and a centrifugal separator sensor M1, before entering the centrifugal separation chamber 36. The centrifugal separator sensor M1 may detect the hematocrit of the blood entering the centrifugal separation chamber 36, for example.

The centrifugal separator 16 of the blood separation device 10 manipulates the centrifugal separation chamber 36 to separate red blood cells from a plasma constituent, which may be platelet-rich plasma or (more preferably) platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and a plasma constituent (as described above).

The plasma constituent is pumped out of the centrifugal separation chamber 36 via line L31 under action of the plasma pump P4. Valve V6 is closed to prevent fluid flow through associated valve station C6 and line L32, while valve V7 is open to direct fluid flow through line L39, a sensor station S4 associated with pressure sensor A4 (which monitors the pressure of the spinning membrane separator 26), and into the spinning membrane separator 26. As described above, the separated plasma passes through the spinning membrane separator 26, which filters out any remaining cellular blood components, resulting in substantially or virtually cell-free plasma. The filtered plasma exits the spinning membrane separator 26 via line L40, passing through spinner outlet sensor M2 (which may monitor the filtered plasma to determine one or more of its properties, such as whether the plasma is hemolytic and/or lipemic), the valve station C7 associated with valve V7, and into plasma bag F8.

While the filtered plasma flows out of the spinning membrane separator 26, the cellular blood components remain in the gap 74 as a waste product that is eventually discarded with the spinning membrane separator 26 at the end of the procedure. As described above, this may be achieved by omitting an outlet associated with the gap 74 or otherwise preventing flow out of the gap 74. For example, if the spinning membrane separator 26 includes a fluid line L41 associated with the spinning membrane separator 26 for the outflow of fluid from the gap 74, that line L41 may be clamped or sealed or otherwise closed to fluid flow, as shown in FIG. 69. Flowing the cellular blood components out of the spinning membrane separator 26 would require some of the plasma to also flow out of the spinning membrane separator 26 via line L41, rather than exiting the spinning membrane separator 26 via line L40 as a filtered plasma product. Accordingly, "dead end" filtering the separated plasma constituent (as shown in FIG. 69) ensures that all of the plasma exits the spinning membrane separator 26 via line L40 as a filtered plasma product, thus increasing the volume of collected plasma.

The red blood cells flow out of the centrifugal separation chamber 36 via line L34. There is no pump associated with line L34, so instead the flow rate at which the red blood cells exit the centrifugal separation chamber 36 is equal to the difference between the flow rates of the centrifuge pump P3 and plasma pump P4. Valve V6 associated with valve station C6 is closed to prevent fluid flow through associated line L32, thereby directing the red blood cells through line L35. The valve V2 associated with valve station C2 is closed, while the valve V1 associated with valve station C1 is open to direct the red blood cells from line L35 into line L36 and to the junction of lines L37 and L38. The saline pump P2 associated with line L37 is inactive, thus directing the red blood cells into line L38. In line L38, the red blood cells travel through the sensor station S1 associated with pressure sensor A1 (which may monitor vein pressure if the fluid recipient is a living donor), a return line filter 58, air detector M3, and the valve station C11 associated with open valve V11 on their way to the recipient (which may be the same as the blood source) via the second needle or blood access device. Saline or another replacement fluid may be drawn from the saline bag F2 via line L37 under action of the saline pump P2 to a junction, where it mixes with the red blood cells being conveyed through line L36 to the recipient, although it may be more typical for replacement fluid to not be conveyed to the recipient until plasma collection is complete.

The valve V6 associated with valve station C6 may be selectively opened, along with the valve V7 associated with valve station C7 being closed. This directs the plasma constituent flowing through line L31 to flow into line L32 (instead of line L39) and to a junction, where it mixes with the red blood cells flowing through line L34, to be conveyed out of the fluid flow circuit 12*i* as a return fluid. This may be advantageous if the controller 18 determines that a sufficient amount of plasma has been collected and that further plasma may be conveyed to a recipient.

This single-phase procedure continues until the target amount of filtered plasma has been collected.

6. Double Needle Fluid Flow Circuit and Procedure—Filtered Plasma Product, with Cell Return a. Fluid Flow Circuit FIG. 2J is a schematic view of a fluid flow circuit 12*j* that is a variation of the fluid flow circuit 12*i* of FIG. 2I. Due to similarities between the fluid flow circuit 12*j* of FIG. 2J and the fluid flow circuit 12*i* of FIG. 2I, similarly configured fluid lines will be identified with the same reference labels in FIGS. 2I and 2J, while lines that are differently configured and/or not employed in the fluid flow circuit 12*i* of FIG. 2I will be identified in FIG. 2J with different reference labels.

While FIG. 69 illustrates a process in which a separated plasma constituent is "dead end" filtered, without cellular blood components ever being removed from the spinning membrane separator 26, the fluid flow circuit 12*j* of FIG. 2J is configured to allow for "dead end" filtration followed by the removal of cellular blood components from the spinning membrane separator 26 at the end of a procedure. In particular, the fluid flow circuit 12*j* differs from the fluid flow circuit 12*i* in that line L41 is not sealed or otherwise closed to flow, but rather includes an associated valve V8 that may be selectively opened and closed to allow fluid flow through an associated valve station C8 and, hence, through line L41. As will be described, valve V8 remains closed during the procedure, with the valve V8 only opening at the end of the procedure to allow the cellular blood components to be flushed from the spinning membrane separator 26 via line L41, to be conveyed to a recipient.

b. Separation and Collection Phase

A separation and collection phase (FIG. 70) proceeds as described above with regard to the single phase (FIG. 69) of the fluid flow circuit 12*i* of FIG. 2I, though with the red blood cells exiting the centrifugal separation chamber 36 via line L34 additionally flowing through a valve station C4 associated with line L34 (unlike in FIG. 69). As line L41 is not sealed or otherwise closed to fluid flow, the valve V8 associated with valve station C8 is closed to prevent fluid flow through line L41, thus retaining cellular blood components filtered out of the separated plasma constituent within the spinning membrane separator 26.

The separation and collection phase of FIG. 70 may continue until the target amount of filtered plasma has been collected.

c. Flush Phase

When plasma collection has been completed, the system transitions to a flush phase, which is shown in FIG. 71. In this phase, the valves V3 and V8 associated with valve stations C3 and C8 (respectively) are moved from being closed to being open, while the valves V4, V7, V11 associated with valve stations C4, C7, and C11 (respectively) are moved from being open to being closed.

With the valve stations situated as shown in FIG. 71, saline from the saline bag F2 is drawn through line L37 by operation of the saline pump P2. The saline travels to the junction of lines L36 and L38, with the valve V1 associated with valve station C1 being open, while the valve V11 associated with valve station C11 is closed. The saline flows into line L36 and through the valve station C1 associated with open valve V1. The saline continues flowing through line L36 to the junction of lines L27 and L35. The valve V2 associated with valve station C2 and line L27 is closed, such that the saline flows into and through line L35 to the junction of lines L34 and L42. The valve V4 associated with valve station C4 and line L34 is closed, which causes the saline to flow into and through line L42 to the junction of lines L32 and L41. The valve V6 associated with valve station C6 and line L32 is closed, while the valve V8 associated with valve station C8 and line L41 is open, which directs the saline through line L41 and into the spinning membrane separator 26.

The saline travels through the spinning membrane separator 26 in the opposite direction of the flow of the plasma constituent through the spinning membrane separator 26 during separation and collection of filtered plasma (FIG. 70). The valve V7 associated with valve station C7 and line L40 is closed, such that the saline flushes the cellular blood components out of the spinning membrane separator 26 via line L39, where the mixture flows to the junction of lines L31 and L32. The valve V6 associated with valve station C6 and line L32 is closed, which causes the mixture to flow into line L31, where the plasma pump P4 (operating in reverse) conveys the mixture into the centrifugal separation chamber 36.

The valve V4 associated with valve station C4 and line L34 is closed, which causes the mixture to flush the contents of the centrifugal separation chamber 36 out of the chamber via line L30 as a return fluid. Finally, the return fluid is pumped out of the fluid flow circuit 12j by reverse operation of the centrifuge pump P3, with the return fluid flowing through lines L30 and line L28 to a recipient (such as the blood source).

While the amount of cellular blood components filtered from the plasma constituent in the spinning membrane separator 26 will typically be relatively low (due to the plasma constituent exiting the centrifugal separation chamber 36 tending to have a low cell content), the fluid flow circuit 12j of FIG. 2J thus allows for those cellular blood components to be conveyed to a recipient (such as the blood source) instead of being discarded as a waste product, as is the case in a procedure using the fluid flow circuit 12i of FIG. 2I. Additionally, while saline is described and shown in FIG. 71 as being used to flush blood components from the spinning membrane separator 26 and the centrifugal separation chamber 36, it should be understood that other fluids (e.g., air or some other replacement fluid or separated plasma) may also or alternatively be used to flush blood components from the spinning membrane separator 26 and the centrifugal separation chamber 36.

Aspects

Aspect 1. A blood separation device comprising: a centrifugal separator; a spinning membrane separator drive unit; a pump system; and a controller configured to control the pump system to convey blood into the centrifugal separator, control the centrifugal separator to separate red blood cells from the blood, and control the pump system to collect at least a portion of the separated red blood cells.

Aspect 2. The blood separation device of Aspect 1, wherein the controller is configured to control the centrifugal separator to separate red blood cells and a plasma constituent from the blood, and control the pump system to collect at least a portion of the plasma constituent.

Aspect 3. The blood separation device of Aspect 2, wherein the controller is further configured to control the pump system to convey at least a portion of the collected plasma constituent out of the blood separation device while controlling the centrifugal separator to separate red blood cells and plasma constituent from the blood.

Aspect 4. The blood separation device of any one of the preceding Aspects, wherein the controller is configured to control the pump system to convey said at least a portion of the separated red blood cells through a leukocyte removal filter while controlling the centrifugal separator to separate red blood cells from the blood.

Aspect 5. The blood separation device of Aspect 4, wherein the controller is further configured to control the pump system to mix said at least a portion of the separated red blood cells with an additive solution prior to said at least a portion of the separated red blood cells being conveyed through the leukocyte removal filter, wherein the controller is configured to control the pump system to add the additive solution to said at least a portion of the separated red blood cells at a rate configured to produce a mixture having a predetermined or preselected hematocrit.

Aspect 6. The blood separation device of Aspect 5, wherein said predetermined or preselected hematocrit is in a range of approximately 55% to approximately 75%.

Aspect 7. The blood separation device of any one of the preceding Aspects, wherein the controller is configured to control the pump system to collect a portion of the blood and to convey another portion of the blood into the centrifugal separator.

Aspect 8. The blood separation device of Aspect 7, wherein the controller is further configured to control the pump system to convey at least a portion of the collected blood into the centrifugal separator, control the centrifugal separator to separate red blood cells from said at least a portion of the collected blood, and control the pump system to collect at least a portion of the red blood cells separated from said at least a portion of the collected blood.

Aspect 9. The blood separation device of any one of the preceding Aspects, wherein the controller is configured to control the centrifugal separator to separate red blood cells and a plasma constituent from the blood, and control the pump system to convey at least a portion of the plasma constituent out of the blood separation device.

Aspect 10. The blood separation device of any one of the preceding Aspects, wherein the controller is configured to control the centrifugal separator and not the spinning membrane separator drive unit to separate red blood cells from the blood.

Aspect 11. A blood separation method comprising: mounting a fluid flow circuit to a blood separation device including a centrifugal separator and a spinning membrane separator drive unit; conveying blood through the fluid flow circuit; separating red blood cells from at least a portion of the blood in the fluid flow circuit using the centrifugal separator; and collecting at least a portion of the separated red blood cells.

Aspect 12. The method of Aspect 11, wherein said separating red blood cells from said at least a portion of the blood in the fluid flow circuit includes separating a plasma constituent from the blood and conveying at least a portion of the plasma constituent into a return container.

Aspect 13. The method of Aspect 12, further comprising conveying at least a portion of the plasma constituent in the return container out of the fluid flow circuit while separating red blood cells from blood using the centrifugal separator.

Aspect 14. The method of any one of Aspects 11-13, wherein said collecting at least a portion of the separated red blood cells includes conveying said at least a portion of the separated red blood cells through a leukocyte removal filter while separating red blood cells from blood using the centrifugal separator.

Aspect 15. The method of Aspect 14, further comprising mixing said at least a portion of the separated red blood cells with an additive solution prior to conveying said at least a portion of the separated red blood cells through the leukocyte removal filter, wherein the additive solution is added to said at least a portion of the separated red blood cells at a rate configured to produce a mixture having a predetermined or preselected hematocrit.

Aspect 16. The method of Aspect 15, wherein said predetermined or preselected hematocrit is in a range of approximately 55% to approximately 75%.

Aspect 17. The method of any one of Aspects 11-16, wherein said conveying blood through the fluid flow circuit includes conveying a portion of the blood into an in-process container and another portion of the blood into the centrifugal separator.

Aspect 18. The method of Aspect 17, further comprising conveying at least a portion of the blood in the in-process container into the centrifugal separator, separating red blood cells from said at least a portion of the blood from the in-process container using the centrifugal separator, and collecting at least a portion of the red blood cells separated from the blood from the in-process container.

Aspect 19. The method of any one of Aspects 11-18, wherein said separating red blood cells from at least a portion of the blood in the fluid flow circuit includes separating a plasma constituent from the blood and conveying at least a portion of the plasma constituent out of the fluid flow circuit.

Aspect 20. The method of any one of Aspects 11-19, wherein said separating red blood cells from said at least a portion of the blood in the fluid flow circuit using the centrifugal separator includes separating red blood cells from said at least a portion of the blood in the fluid flow circuit using the centrifugal separator and not the spinning membrane separator drive unit.

Aspect 21. A blood separation device comprising: a centrifugal separator; a spinning membrane separator drive unit; a pump system; and a controller configured to control the pump system to convey blood into the centrifugal separator, control the centrifugal separator to separate red blood cells and plasma from the blood; and control the pump system to collect at least a portion of the separated red blood cells and at least a portion of the separated plasma.

Aspect 22. The blood separation device of Aspect 21, wherein the controller is further configured to control the pump system to convey at least a portion of the collected red blood cells out of the blood separation device while controlling the centrifugal separator to separate red blood cells and plasma from the blood.

Aspect 23. The blood separation device of any one of Aspects 21-22, wherein the controller is configured to control the pump system to convey said least a portion of the separated red blood cells through a leukocyte removal filter while controlling the centrifugal separator to separate red blood cells and plasma from the blood.

Aspect 24. The blood separation device of Aspect 23, wherein the controller is further configured to control the pump system to mix said at least a portion of the separated red blood cells with an additive solution prior to said at least a portion of the separated red blood cells being conveyed through the leukocyte removal filter, wherein the controller is configured to control the pump system to add the additive solution to said at least a portion of the separated red blood cells at a rate configured to produce a mixture having a predetermined or preselected hematocrit.

Aspect 25. The blood separation device of any one of Aspects 21-24, wherein the controller is configured to control the pump system to collect a portion of the blood and to convey another portion of the blood into the centrifugal separator.

Aspect 26. The blood separation device of Aspect 25, wherein the controller is further configured to control the pump system to convey at least a portion of the collected blood into the centrifugal separator, control the centrifugal separator to separate red blood cells and plasma from said at least a portion of the collected blood, and control the pump system to collect at least a portion of the plasma separated from said at least a portion of the collected blood and to convey at least a portion of the red blood cells separated from said at least a portion of the collected blood out of the blood separation device.

Aspect 27. The blood separation device of Aspect 25, wherein the controller is further configured to control the pump system to convey at least a portion of the collected blood into the centrifugal separator, control the centrifugal separator to separate red blood cells and plasma from said at least a portion of the collected blood, and control the pump system to collect at least a portion of the red blood cells separated from said at least a portion of the collected blood and collect at least a portion of the plasma separated from said at least a portion of the collected blood.

Aspect 28. The blood separation device of any one of Aspects 21-27, wherein the controller is further configured to control the pump system to convey said at least a portion of the separated plasma into the spinning membrane separator drive unit, and control the spinning membrane separator drive unit to separate said at least a portion of the separated plasma into cellular blood components and substantially cell-free plasma.

Aspect 29. The blood separation device of Aspect 28, wherein the controller is further configured to control the pump system to convey the substantially cell-free plasma out of the spinning membrane separator drive unit for collection without conveying the cellular blood components out of the spinning membrane separator drive unit.

Aspect 30. The blood separation device of Aspect 28, wherein the controller is further configured to control the pump system to convey the substantially cell-free plasma out of the spinning membrane separator drive unit for collection, and after conveying the substantially cell-free plasma out of the spinning membrane separator drive unit for collection, convey the cellular blood components out of the spinning membrane separator drive unit.

Aspect 31. A blood separation method comprising: mounting a fluid flow circuit to a blood separation device including a centrifugal separator and a spinning membrane separator drive unit; conveying blood through the fluid flow circuit; separating red blood cells and plasma from at least a portion of the blood in the fluid flow circuit using the centrifugal separator; collecting at least a portion of the separated red blood cells; and collecting at least a portion of the separated plasma.

Aspect 32. The method of Aspect 31, wherein said separating red blood cells and plasma from said at least a portion of the blood in the fluid flow circuit includes conveying at least a portion of the red blood cells into a return container.

Aspect 33. The method of Aspect 32, further comprising conveying at least a portion of the red blood cells in the return container out of the fluid flow circuit while separating red blood cells and plasma from blood using the centrifugal separator.

Aspect 34. The method of any one of Aspects 31-33, wherein said collecting at least a portion of the separated red blood cells includes mixing said at least a portion of the separated red blood cells with an additive solution, and conveying the mixture of separated red blood cells and additive solution through a leukocyte removal filter, and the additive solution is added to said at least a portion of the separated red blood cells at a rate configured to produce a mixture having a predetermined or preselected hematocrit.

Aspect 35. The method of any one of Aspects 31-34, wherein said conveying blood through the fluid flow circuit includes conveying a portion of the blood into an in-process container and another portion of the blood into the centrifugal separator.

Aspect 36. The method of Aspect 35, further comprising conveying at least a portion of the blood in the in-process container into the centrifugal separator, separating red blood cells and plasma from said at least a portion of the blood from the in-process container using the centrifugal separator, collecting at least a portion of the plasma separated from the blood from the in-process container, and conveying at least a portion of the red blood cells separated from the blood from the in-process container out of the fluid flow circuit.

Aspect 37. The method of Aspect 35, further comprising conveying at least a portion of the blood in the in-process container into the centrifugal separator, separating red blood cells and plasma from said at least a portion of the blood from the in-process container using the centrifugal separator, and collecting at least a portion of the plasma separated from the blood from the in-process container and at least a portion of the red blood cells separated from the blood from the in-process container.

Aspect 38. The method of any one of Aspects 31-37, further comprising, conveying said at least a portion of the separated plasma into the spinning membrane separator drive unit, and separating said at least a portion of the separated plasma into cellular blood components and substantially cell-free plasma.

Aspect 39. The method of Aspect 38, further comprising conveying the substantially cell-free plasma out of the spinning membrane separator drive unit without conveying the cellular blood components out of the spinning membrane separator drive unit.

Aspect 40. The method of Aspect 38, further comprising conveying the substantially cell-free plasma out of the spinning membrane separator drive unit, and after conveying the substantially cell-free plasma out of the spinning membrane separator drive unit, conveying the cellular blood components out of the spinning membrane separator drive unit.

Aspect 41. A blood separation device comprising: a centrifugal separator; a spinning membrane separator drive unit; a pump system; and a controller configured to control the pump system to convey blood into the centrifugal separator, control the centrifugal separator to separate plasma from the blood, and control the pump system to collect at least a portion of the plasma.

Aspect 42. The blood separation device of Aspect 41, wherein the controller is programmed to control the centrifugal separator to separate the blood into plasma and red blood cells and to control the pump system to convey at least a portion of the red blood cells out of the blood separation device.

Aspect 43. The blood separation device of Aspect 42, wherein the controller is programmed to control the pump system to sequentially convey blood into the blood separation device and convey said at least a portion of the red blood cells out of the blood separation device.

Aspect 44. The blood separation device of any one of Aspects 41-43, wherein the controller is configured to control the pump system to collect a portion of the blood and to convey another portion of the blood into the centrifugal separator.

Aspect 45. The blood separation device of Aspect 44, wherein the controller is further configured to control the pump system to convey at least a portion of the collected blood into the centrifugal separator, control the centrifugal separator to separate plasma from said at least a portion of the collected blood, and control the pump system to collect at least a portion of the plasma separated from said at least a portion of the collected blood.

Aspect 46. The blood separation device of Aspect 42, wherein the controller is programmed to control the pump system to simultaneously convey blood into the blood separation device and convey said at least a portion of the red blood cells out of the blood separation device.

Aspect 47. The blood separation device of any one of Aspects 41-46, wherein the controller is configured to control the centrifugal separator to separate platelet-free plasma from the blood.

Aspect 48. The blood separation device of any one of Aspects 41-47, wherein the controller is further configured to control the pump system to convey said at least a portion of the separated plasma into the spinning membrane separator drive unit, and control the spinning membrane separator drive unit to separate said at least a portion of the separated plasma into cellular blood components and substantially cell-free plasma.

Aspect 49. The blood separation device of Aspect 48, wherein the controller is further configured to control the pump system to convey the substantially cell-free plasma out of the spinning membrane separator drive unit for collection without conveying the cellular blood components out of the spinning membrane separator drive unit.

Aspect 50. The blood separation device of Aspect 48, wherein the controller is further configured to control the pump system to convey the substantially cell-free plasma out of the spinning membrane separator drive unit for collection, and after conveying the substantially cell-free plasma out of the spinning membrane separator drive unit for collection, convey the cellular blood components out of the spinning membrane separator drive unit.

Aspect 51. A blood separation method comprising: mounting a fluid flow circuit to a blood separation device including a centrifugal separator and a spinning membrane separator drive unit; conveying blood through the fluid flow circuit; separating plasma from at least a portion of the blood in the fluid flow circuit using the centrifugal separator; and collecting at least a portion of the separated plasma.

Aspect 52. The method of Aspect 51, wherein said separating plasma from said at least a portion of the blood in the fluid flow circuit includes separating red blood cells from said at least a portion of the blood in the fluid flow circuit using the centrifugal separator, and further comprising conveying at least a portion of the red blood cells out of the fluid flow circuit.

Aspect 53. The method of Aspect 52, wherein blood is not conveyed into the fluid flow circuit at the same time as said at least a portion of the red blood cells is conveyed out of the fluid flow circuit.

Aspect 54. The method of any one of Aspects 51-53, wherein said conveying blood through the fluid flow circuit includes conveying a portion of the blood into an in-process container and another portion of the blood into the centrifugal separator.

Aspect 55. The method of Aspect 54, further comprising conveying at least a portion of the blood in the in-process container into the centrifugal separator, separating plasma from said at least a portion of the blood from the in-process container using the centrifugal separator, and collecting at least a portion of the plasma separated from the blood from the in-process container.

Aspect 56. The method of Aspect 52, wherein blood is conveyed into the fluid flow circuit at the same time as said at least a portion of the red blood cells is conveyed out of the fluid flow circuit.

Aspect 57. The method of any one of Aspects 51-56, wherein separating plasma from at least a portion of the blood in the fluid flow circuit using the centrifugal separator includes separating platelet-free plasma from said at least a portion of the blood in the fluid flow circuit.

Aspect 58. The method of any one of Aspects 51-57, further comprising, conveying said at least a portion of the separated plasma into the spinning membrane separator drive unit, and separating said at least a portion of the separated plasma into cellular blood components and substantially cell-free plasma.

Aspect 59. The method of Aspect 58, further comprising conveying the substantially cell-free plasma out of the spinning membrane separator drive unit without conveying the cellular blood components out of the spinning membrane separator drive unit.

Aspect 60. The method of Aspect 58, further comprising conveying the substantially cell-free plasma out of the spinning membrane separator drive unit, and after conveying the substantially cell-free plasma out of the spinning membrane separator drive unit, conveying the cellular blood components out of the spinning membrane separator drive unit.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood separation method comprising:
   mounting a fluid flow circuit to a blood separation device including a centrifugal separator and a spinning membrane separator drive unit;
   conveying blood through the fluid flow circuit;
   separating red blood cells and a plasma constituent from at least a portion of the blood in the fluid flow circuit using the centrifugal separator; and
   collecting a first portion of the separated red blood cells while conveying a first portion of the plasma constituent from the centrifugal separator into a container;
   collecting a second portion of the separated red blood cells while conveying said first portion of the plasma constituent from the container to a recipient along with a second portion of the plasma constituent from the centrifugal separator that is not first conveyed into the container; and
   after said first portion of the plasma constituent has been conveyed from the container to the recipient and the container has been emptied, collecting a third portion of the separated red blood cells and conveying a third portion of the plasma constituent from the centrifugal separator to the recipient without first being conveyed into the container, wherein the spinning membrane separator drive unit is not actuated when the blood is being conveyed through the fluid flow circuit, when the red blood cells and plasma constituent are being separated from said at least a portion of the blood in the fluid flow circuit, and when the separated red blood cells are being collected.

2. The method of claim 1, wherein the first portion of the plasma constituent in the container is conveyed out of the fluid flow circuit while separating red blood cells from blood using the centrifugal separator.

3. The method of claim 1, wherein the separated red blood cells are conveyed through a leukocyte removal filter while separating red blood cells from blood using the centrifugal separator.

4. The method of claim 3, further comprising mixing the separated red blood cells with an additive solution prior to conveying the separated red blood cells through the leukocyte removal filter, wherein the additive solution is added to the separated red blood cells at a rate configured to produce a mixture having a predetermined or preselected hematocrit.

5. The method of claim 4, wherein said predetermined or preselected hematocrit is in a range of approximately 55% to approximately 75%.

6. The method of claim 1, wherein said conveying blood through the fluid flow circuit includes conveying a portion of the blood into an in-process container and another portion of the blood into the centrifugal separator.

7. The method of claim 6, further comprising
   conveying at least a portion of the blood in the in-process container into the centrifugal separator,
   separating red blood cells from said at least a portion of the blood from the in-process container using the centrifugal separator, and
   collecting at least a portion of the red blood cells separated from the blood from the in-process container.

8. The method of claim 1, wherein
   the blood separation device includes a plurality of pumps, and
   one of the pumps of the blood separation device is not actuated when the blood is being conveyed through the fluid flow circuit, when the red blood cells and plasma constituent are being separated from said at least a portion of the blood in the fluid flow circuit, and when the separated red blood cells are being collected.

9. The method of claim 1, wherein
the separated red blood cells are collected in a red blood cell collection container, and
a red blood cell flow path from the centrifugal separator to the red blood cell collection container omits a pump.

10. The method of claim 9, wherein
a blood flow path from a blood source to the centrifugal separator includes a first pump,
a plasma flow path from the centrifugal separator to the container includes a second pump, and
a flow rate of the separated red blood cells through the red blood cell flow path is determined based on operational rates of the first and second pumps.

11. The method of claim 10, wherein the flow rate of the separated red blood cells through the red blood cell flow path is equal to the difference between a flow rate at which the blood is pumped into the centrifugal separator and a flow rate at which the plasma constituent is pumped out of the centrifugal separator.

12. The method of claim 4, further comprising detecting a hematocrit of the blood being conveyed into the centrifugal separator.

13. The method of claim 12, wherein
the blood separation device includes an additive pump that is configured to pump the additive solution to the separated red blood cells, and
the additive pump operates at a rate that is based at least in part on the hematocrit of the blood being conveyed into the centrifugal separator.

14. The method of claim 1, further comprising adding a replacement fluid to the plasma constituent being conveyed to the recipient.

15. The method of claim 1, further comprising temporarily preventing the plasma constituent from being conveyed to the recipient while conveying a replacement fluid to the recipient.

16. The method of claim 15, further comprising alternately conveying the plasma constituent and the replacement fluid to the recipient.

17. The method of claim 1, further comprising completing the collection of the separated red blood cells when a target volume of the separated red blood cells has been collected.

18. The method of claim 1, further comprising completing the collection of the separated red blood cells when a target volume of blood has been separated.

19. The method of claim 1, wherein the plasma constituent is platelet-rich plasma.

20. The method of claim 1, wherein the plasma constituent is platelet-poor plasma.

* * * * *